US010858405B2

(12) United States Patent
Bosse-Doenecke et al.

(10) Patent No.: US 10,858,405 B2
(45) Date of Patent: Dec. 8, 2020

(54) EGFR BINDING PROTEINS

(71) Applicant: Navigo Proteins GmbH, Halle/Saale (DE)

(72) Inventors: Eva Bosse-Doenecke, Halle/Saale (DE); Florian Settele, Halle/Saale (DE); Erik Fiedler, Halle/Saale (DE); Ulrich Haupts, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 322 days.

(21) Appl. No.: 15/548,976

(22) PCT Filed: Feb. 4, 2016

(86) PCT No.: PCT/EP2016/052408
§ 371 (c)(1),
(2) Date: Aug. 4, 2017

(87) PCT Pub. No.: WO2016/124702
PCT Pub. Date: Aug. 11, 2016

(65) Prior Publication Data
US 2018/0030098 A1 Feb. 1, 2018

(30) Foreign Application Priority Data

Feb. 6, 2015 (EP) .................................... 15154159

(51) Int. Cl.
| C07K 14/435 | (2006.01) |
| C07K 14/71 | (2006.01) |
| C07K 14/00 | (2006.01) |
| C07K 16/28 | (2006.01) |
| A61K 38/00 | (2006.01) |

(52) U.S. Cl.
CPC ............ C07K 14/435 (2013.01); C07K 14/00 (2013.01); C07K 14/71 (2013.01); C07K 16/2863 (2013.01); A61K 38/00 (2013.01); C07K 2317/24 (2013.01); C07K 2317/92 (2013.01); C07K 2319/30 (2013.01); C07K 2319/31 (2013.01); C07K 2319/95 (2013.01)

(58) Field of Classification Search
CPC .............. C07K 14/435; C07K 16/2863; C07K 2319/95; C07K 2319/31; C07K 2319/30; C07K 2317/92; C07K 2317/24; C07K 14/00; C07K 14/71; A61K 38/00
See application file for complete search history.

(56) References Cited

U.S. PATENT DOCUMENTS

| 4,873,192 | A | 10/1989 | Kunkel |
| 5,789,166 | A | 8/1998 | Bauer et al. |
| 5,958,684 | A | 9/1999 | Van Leeuwen et al. |
| 6,217,863 | B1 | 4/2001 | Godavarti et al. |
| 6,569,677 | B1 | 5/2003 | Legrand et al. |
| 6,620,587 | B1 | 9/2003 | Taussig et al. |
| 6,673,901 | B2 | 1/2004 | Koide |
| 6,799,121 | B2 | 9/2004 | Chu et al. |
| 7,250,297 | B1 | 7/2007 | Beste et al. |
| 7,273,924 | B1 | 9/2007 | Neri et al. |
| 7,393,918 | B2 | 7/2008 | Golemi-Kota et al. |
| 7,601,803 | B1 | 10/2009 | Fiedler et al. |
| 7,838,629 | B2 | 11/2010 | Fiedler et al. |
| 7,851,599 | B2 | 12/2010 | Menrad et al. |
| 8,097,254 | B2 | 1/2012 | Neri et al. |
| 8,404,814 | B2 | 3/2013 | Neri et al. |
| 8,426,357 | B2 | 4/2013 | Kraehmer et al. |
| 8,455,625 | B2 | 6/2013 | Neri et al. |
| 8,592,144 | B2 | 11/2013 | Fiedler et al. |
| 8,592,179 | B2 | 11/2013 | Schraeml et al. |
| 8,623,373 | B2 | 1/2014 | Zardi et al. |
| 8,748,351 | B2 | 6/2014 | Kunert et al. |
| 8,790,895 | B2 | 7/2014 | Fiedler et al. |
| 8,791,238 | B2 | 7/2014 | Fiedler et al. |
| 8,921,304 | B2 | 12/2014 | Steuernagel et al. |
| 9,492,572 | B2 | 11/2016 | Nerkamp et al. |
| 2003/0045681 | A1 | 3/2003 | Neri et al. |
| 2003/0073623 | A1 | 4/2003 | Drmanac et al. |
| 2004/0043386 | A1 | 3/2004 | Pray et al. |
| 2006/0058510 | A1 | 3/2006 | Skerra et al. |
| 2006/0099686 | A1 | 5/2006 | Fiedler et al. |
| 2007/0015248 | A1 | 1/2007 | Anton et al. |

(Continued)

FOREIGN PATENT DOCUMENTS

| AU | 2013318928 | 4/2015 |
| EP | 1591527 A1 | 11/2005 |

(Continued)

OTHER PUBLICATIONS

Branden et al., Introduction to Protein Structure, Garland Publishing Inc., New York, p. 247, 1991.*
Sadowski et al., Current Opinion in Structural Biology 19:357-362, 2009.*
Abedi et al. (1998) Green fluorescent protein as a scaffold for intracellular presentation of peptides. Nucleic Acids Research 26(2):623-630.
Advisory Action corresponding to U.S. Appl. No. 10/030,605 dated Oct. 13, 2006.
Advisory Action corresponding to U.S. Appl. No. 11/732,632 dated Jun. 30, 2010.

(Continued)

*Primary Examiner* — Delia M Ramirez
(74) *Attorney, Agent, or Firm* — Jenkins, Wilson, Taylor & Hunt, P.A.

(57) ABSTRACT

The present invention relates to new EGFR binding molecules based on ubiquitin muteins (Affilin®), preferably Affilin molecules having a characteristic three amino acid residue motif. The invention further refers to EGFR binding molecules that bind to different or non-overlapping epitopes than the anti-EGFR monoclonal antibody Cetuximab. The invention further relates to the use of these EGFR binding proteins in medicine, preferably for use in the diagnosis or treatment of cancer.

10 Claims, 15 Drawing Sheets

Specification includes a Sequence Listing.

(56) References Cited

U.S. PATENT DOCUMENTS

| | | |
|---|---|---|
| 2007/0111287 A1 | 5/2007 | Fiedler et al. |
| 2007/0189963 A1 | 8/2007 | Neri et al. |
| 2007/0248536 A1 | 10/2007 | Fiedler et al. |
| 2007/0286843 A1 | 12/2007 | Pfizenmaier et al. |
| 2008/0171851 A1 | 7/2008 | Fiedler et al. |
| 2010/0119446 A1 | 5/2010 | Grabulovski et al. |
| 2010/0130720 A1 | 5/2010 | Schraeml et al. |
| 2011/0162095 A1 | 6/2011 | Hill et al. |
| 2012/0244596 A1 | 9/2012 | Skerra et al. |
| 2012/0301393 A1 | 11/2012 | Steuernagel et al. |
| 2013/0011334 A1 | 1/2013 | Steuernagel et al. |
| 2013/0097737 A1 | 4/2013 | Kovalic et al. |
| 2013/0157878 A1 | 6/2013 | Kunert et al. |
| 2014/0219959 A1 | 8/2014 | Nerkamp et al. |
| 2015/0183846 A1 | 7/2015 | Lange et al. |
| 2018/0030140 A1 | 2/2018 | Bosse-Doenecke et al. |
| 2018/0194819 A1 | 7/2018 | Fiedler et al. |
| 2018/0273636 A1 | 9/2018 | Settele et al. |
| 2018/0305463 A1 | 10/2018 | Haupts |
| 2019/0117791 A1 | 4/2019 | Haupts et al. |
| 2019/0177376 A1 | 6/2019 | Knick et al. |

FOREIGN PATENT DOCUMENTS

| | | |
|---|---|---|
| EP | 2 532 672 A2 | 12/2012 |
| EP | 2727942 A1 | 5/2014 |
| EP | 2 738 180 | 6/2014 |
| EP | 2829552 A1 | 1/2015 |
| RU | 2134696 C1 | 8/1999 |
| WO | WO 2005/044845 A2 | 5/2005 |
| WO | WO 2007/054120 A1 | 5/2007 |
| WO | WO 2012/171541 A1 | 12/2012 |
| WO | WO 2013/186329 A1 | 12/2013 |
| WO | WO 2014/094799 | 6/2014 |
| WO | WO 2016/124670 A1 | 8/2016 |

OTHER PUBLICATIONS

Advisory Action corresponding to U.S. Appl. No. 12/072,959 dated May 18, 2010.
Baker et al. (1994) Protein Expression Using Cotranslational Fusion and Cleavage of Ubiquitin. The Journal of Biological Chemistry 269(41):25381-25386.
Beal et al. (1996) Surface hydrophobic residues of multiubiquitin chains essential for proteolytic targeting. PNAS 93:861-866.
Beste et al. (1999) Small antibody-like proteins with prescribed ligand specificities derived from the lipocalin fold. PNAS 96:1898-1903.
Birchler et al. (1999) Selective targeting and photocoagulation of ocular angiogenesis mediated by a phage-derived human antibody fragment. Nature Biotechnology 17:984-988.
Bird et al. (1988) Single-Chain Antigen-Binding Proteins. Science. 242:423-426.
Bofill et al. (2005) Engineering Stabilising beta-Sheet Interactions into a Conformationally Flexible Region of the Folding Transition State of Ubiquitin. Journal of Molecular Biology 353(2):373-384.
Bolton et al. (2001) Structure and Properties of a Dimeric N-terminal Fragment of Human Ubiquitin. Journal of Molecular Biology 314(4):773-787.
Borsi et al. (2003) Selective targeted delivery of TNFα to tumor blood vessels. Blood 102(13):4384-4392.
Brinkmann et al. (1993) A recombinant immunotoxin containing a disulfide-stabilized Fv-fragment. PNAS 90:7538-7542.
Brinkmann et al. (1997) Stabilization of a Recombinant Fv Fragment by Base-Loop Interconnection and VH-VL Permutation. Journal of Molecular Biology 268:107-117.
Buchberger et al. (2001) The UBX Domain: A Widespread Ubiquitin-Like Module. Journal of Molecular Biology 307(1):17-24.
Burch & Haas (1994) Site-directed mutagenesis of ubiquitin. Differential roles for arginine in the interaction with ubiquitin-activating enzyme. Biochemistry 33(23):7300-7308.
Campion et al. (1990) Biochemical Properties of Site-Directed Mutants of Human Epidermal Growth Factor: Importance of Solvent-Exposed Hydrophobic Residues of the Amino-Terminal Domain in Receptor Binding. Biochemistry 29(42):9988-9993.
Connolly (1983) Solvent-Accessible Surfaces of Proteins and Nucleic Acids. Science 221(4612):709-713.
Corrected Notice of Allowability corresponding to U.S. Appl. No. 11/656,646 dated Sep. 26, 2013.
Database Geneseq online Aug. 18, 2011 (Aug. 18, 2011)Heteromultimeric modified ubiquitin protein, SEQ ID 44., XP002756535, retreived from EBI accession No. GSP:AZJ58575 Database accession No. AZJ58575.
Database Geneseq online Dec. 4, 2014 (Dec. 4, 2014)Anti-EGFR1 antibody light chain-TGF beta RII fusion protein, SEQ: 30., XP002756536, retrieved from EBI accession No. GSP:BBP24113 Database accession No. BBP24113.
Daugherty et al. (1998) Antibody affinity maturation using bacterial surface display. Protein Engineering 11(9):825-832.
De Kruif et al. (1995) Selection and Application of Human Single Chain Fv Antibody Fragments from a Semi-synthetic Phage Antibody Display Library with Designed CDR3 Regions. Journal of Molecular Biology 248:97-105.
Decision to Grant corresponding to Russian Patent Application No. 2012115491/10(023353) dated Nov. 20, 2014.
Deed of Grant corresponding to Australian Patent No. 2010332932 dated May 2, 2013.
Deed of Grant corresponding to Australian Patent No. 2010332938 dated Apr. 4, 2013.
Dikic et al. (2009) Ubiquitin-binding domains—from structures to functions. Nature Reviews 10:659-671.
Ebersbach et al. (2007) Affilin-Novel Binding Molecules Based on Human (—B-Crystallin, an All (—Sheet Protein. Journal of Molecular Biology 372:172-185.
Ecker et al. (1987) Gene Synthesis, Expression, Structures, and Functional Activities of Site-specific Mutants of Ubiquitin. The Journal of Biological Chemistry 262(29):14213-14221.
Ermolenko et al. (2003) Noncharged amino acid residues at the solvent-exposed positions in the middle and at the C terminus of the alpha-helix have the same helical propensity. Protein Science 12(6):1169-1176.
European Search Report corresponding to European Patent Application No. 06 118 519.5-2401 dated Apr. 2, 2007.
European Search Report corresponding to European Patent Application No. 10 181 802.9-2401 dated Feb. 10, 2011.
European Search Report corresponding to European Patent Application No. 09 176 574.3-2401 dated Jan. 18, 2010.
Fiedler et al. (2006) Affilintm Molecules: Novel Ligands for Bioseparation. Food and Bioproducts Processing. 84(C1):3-8.
Finucane et al. (1999a) Core-Directed Protein Design. I. An Experimental Method for Selecting Stable Proteins from Combinatorial Libraries. Biochemistry 38:11604-11612.
Finucane et al. (1999b) Core-Directed Protein Design. II. Rescue of a Multiply Mutated and Destabilized Variant of Ubiquitin. Biochemistry 38(36):11613-11623.
Friedman et al. (2009) Engineering and characterization of a bispecific HER2 X EGFR-binding affibody molecule. Biotechnology and applied biochemistry academic press US 54(2):121-131.
Gebauer & Skerra (2009) Engineered protein scaffolds as next-generation antibody therapeutics. Current Opinion in Chemical Biology 13(3):245-255.
Grabulovski et al. (2007) A Novel, Non-immunogenic Fyn SH3-derived Binding Protein with Tumor Vascular Targeting Properties. The Journal of Biological Chemistry 282(5):3196-3204.
Guo et al. (2004) Protein tolerance to random amino acid change. PNAS 101(25):9205-9210.
Hanes & Plückthun (1997) In vitro selection and evolution of functional proteins by using ribosome display. PNAS 94(10):4937-4942.
Hanes et al. (1998) Ribosome display efficiently selects and evolves high-affinity antibodies in vitro from immune libraries. PNAS 95:14130-14135.

(56) References Cited

OTHER PUBLICATIONS

Hanes et al. (2000) Picomolar affinity antibodies from a fully synthetic naive library selected and evolved by ribosome display. Nature Biotechnology 18:1287-1292.

He & Taussig (1997) Antibody-ribosome-mRNA (ARM) complexes as efficient selection particles for in vitro display and evoluation of antibody combining sites. Nucleic Acids Research 25(24):5132-5134.

Hershko & Ciechanover (1998) The Ubiquitin System. Annu Rev Biochem 67:425-479.

Hey et al. (2005) Artificial, non-antibody binding proteins for pharmaceutical and industrial applications. Trends in Biotechnology 23(10):514-522.

Humphrey et al. (1990) Anti-synthetic peptide antibody reacting at the fusion junction of deletion-mutant epidermal growth factor receptors in human glioblastoma. Proc Natl Acad Sci. 87:4207-4211.

International Preliminary Report on Patentability (Chapter I of the Patent Cooperation Treaty) corresponding to International Patent Application No. PCT/EP2016/052345 dated Aug. 8, 2017.

International Preliminary Report on Patentability (Chapter I of the Patent Cooperation Treaty) corresponding to International Patent Application No. PCT/EP2007/062375 dated May 19, 2009.

International Preliminary Report on Patentability (Chapter I of the Patent Cooperation Treaty) corresponding to International Patent Application No. PCT/EP2010/069665 dated Jun. 19, 2012.

International Preliminary Report on Patentability corresponding to International Patent Application No. PCT/EP2004/005730 dated May 13, 2005.

International Search Report and Written Opinion corresponding to International Patent Application No. PCT/EP2016/052408 dated May 2, 2016.

International Search Report corresponding to International Patent Application No. PCT/EP2000/006698 dated Feb. 2, 2001.

International Search Report corresponding to International Patent Application No. PCT/EP2004/005730 dated Oct. 5, 2004.

International Search Report corresponding to International Patent Application No. PCT/EP2005/010932 dated Apr. 11, 2006.

International Search Report corresponding to International Patent Application No. PCT/EP2007/062375 dated Apr. 25, 2008.

International Search Report corresponding to International Patent Application No. PCT/EP2010/069665 dated Apr. 13, 2011.

International Search Report corresponding to International Patent Application No. PCT/EP2010/069674 dated Jun. 17, 2011.

International Search Report corresponding to International Patent Application No. PCT/EP2012/061455 dated Oct. 25, 2012.

International Search Report corresponding to International Patent Application No. PCT/EP2011/002962 dated Mar. 19, 2012.

International Search Report corresponding to International Patent Application No. PCT/EP2012/061459 dated Sep. 24, 2012.

International Search Report corresponding to International Patent Application No. PCT/EP2013/062310 dated Aug. 2, 2013.

Interview Summary and Corrected Notice of Allowability corresponding to U.S. Appl. No. 11/283,332 dated Jul. 1, 2014.

Interview Summary and Corrected Notice of Allowability corresponding to U.S. Appl. No. 12/072,959 dated Jun. 27, 2014.

Interview Summary correponding to U.S. Appl. No. 11/283,332 dated Dec. 13, 2013.

Jackson (2006) Ubiquitin: a small protein folding paradigm. Org Biomol Chem 4(10):1845-1853.

Khorasanizadeh et al. (1993) Folding and stability of a tryptophan-containing mutant of ubiquitin. Biochemistry 32(27):7054-7063.

Kiel & Serrano (2006) The Ubiquitin Domain Superfold: Structure-based Sequence Alignments and Characterization of Binding Epitopes. Journal of Molecular Biology 355(4):821-844.

Knappik et al. (2000) Fully Synthetic Human Combinatorial Antibody Libraries (HuCAL) Based on Modular Consensus Frameworks and CDRs Randomized with Trinucleotides. Journal of Molecular Biology 296:57-86.

Koide et al. (1998)The Fibronectin Type III Domain as a Scaffold for Novel Binding Proteins. Journal of Molecular Biology 284:1141-1151.

Kolchanov & Shindyalov (1988) Single amino acid substitutions producing instability of globular proteins. Calculation of their frequencies in the entire mutational spectra of the alpha- and beta-subunits of human hemoglobin. Journal of Molecular Evolution 27:154-162.

Krantz et al. (2004) Discerning the Structure and Energy of Multiple Transition States in Protein Folding using Ψ-Analysis. Journal of Molecular Biology 337(2):463-475.

Krippner-Heidenreich et al. (2008) Single-chain TNF, a TNF derivative with enhanced stability and antitumoral activity. Journal of Immunology 180:8176-8183.

Ku & Schultz (1995) Alternate protein frameworks for molecular recognition. PNAS 92:6552-6556.

Larsen & Wang. (2002) The Ubiquitin Superfamily: Members, Features, and Phylogenies. Journal of Proteome Research 1:411-419.

Laub et al. (1995) Localized solution structure refinement of an F45W variant of ubiquitin using stochastic boundary molecular dynamics and NMR distance restraints. Protein Science 4:973-982.

Lazar & Wang (1997) H.De novo design of the hydrophobic core of ubiquitin. Protein Science 6:1167-1178.

Lipovsek & Pluckthun (2004) In-vitro protein evolution by ribosome display and mRNA display. Journal of Immunological Methods 290:51-67.

Lo et al. (2009) Structural Basis for Recognition of Diubiquitins by NEMO. Molecular Cell 33:602-615.

Loladze et al. (2005) Both helical propensity and side-chain hydrophobicity at a partially exposed site in alpha-helix contribute to the thermodynamic stability of ubiquitin. Proteins 58(1):1-6.

Mayr et al. (1994) Domain Interactions and Connecting Peptides in Lens Crystallins. Journal of Molecular Biology 235:84-88.

McConnell & Hoess (1995) Tendamistat as a Scaffold for Conformationally Constrained Phage Peptide Libraries. The Journal of Molecular Biology 250:460-470.

Miura et al. (1999) Characterization of the Binding Interface between Ubiquitin and Class I Human Ubiquitin-conjugating Enzyme 2b by Multidimensional Heteronuclear NMR Spectroscopy in Solution Journal of Molecular Biology 290:213-228.

Müller & Skerra (1994) A.Grafting of a High-Affinity Zn(II)-Binding Site on the β-Barrel of Retional-Binding Protein Results in Enhanced Folding Stability and Enables Simplified Purification. Biochemistry 33(47):14126-14135.

Müller et al. (2001) SUMO, ubiquitin's mysterious cousin. Nat. Rev. Mol. Cell Biol 2:202-210.

Nord et al. (1997) Binding proteins selected from combinatorial libraries of an (—helical bacterial receptor domain. Nature Biotechnology 15:772-777.

Notice of Allowance corresponding to U.S. Appl. No. 10/030,605 dated Apr. 14, 2009.

Notice of Allowance corresponding to U.S. Appl. No. 11/283,332 dated Jun. 6, 2014.

Notice of Allowance corresponding to U.S. Appl. No. 11/732,632 dated Aug. 23, 2010.

Notice of Allowance corresponding to U.S. Appl. No. 11/656,646 dated Aug. 27, 2013.

Notice of Allowance corresponding to U.S. Appl. No. 12/072,959 dated Jun. 3, 2014.

Notice of Allowance corresponding to U.S. Appl. No. 12/514,550 dated Sep. 10, 2013.

Notice of Allowance corresponding to U.S. Appl. No. 13/142,195 dated Aug. 4, 2014.

Notice of Allowance corresponding to U.S. Appl. No. 13/144,809 dated Mar. 3, 2014.

Notice of Allowance corresponding to U.S. Appl. No. 14/126,358 dated Sep. 9, 2016.

Notification Concerning Transmittal of International Preliminary Report on Patentability (Chapter I of the Patent Cooperation Treaty) corresponding to International Patent Application No. PCT/EP2016/052345 dated Apr. 11, 2016.

(56) References Cited

OTHER PUBLICATIONS

Notification Concerning Transmittal of International Preliminary Report on Patentability (Chapter I of the Patent Cooperation Treaty) corresponding to International Patent Application No. PCT/EP2010/069666 dated Jun. 28, 2012.
Notification Concerning Transmittal of International Preliminary Report on Patentability (Chapter I of the Patent Cooperation Treaty) corresponding to International Patent Application No. PCT/EP2010/069674 dated Jun. 28, 2012.
Notification of Transmittal of Translation of the International Preliminary Report on Patentability (Chapter I of the Patent Cooperation Treaty) corresponding to International Patent Application No. PCT/EP2004/005730 dated Apr. 13, 2006.
Notification of Transmittal of Translation of the International Preliminary Report on Patentability (Chapter I or Chapter II of the Patent Cooperation Treaty) corresponding to International Patent Application No. PCT/EP2005/010932 dated May 3, 2007.
Nygren & Uhlen (1997) Scaffolds for engineering novel binding sites in proteins. Current Opinion in Structural Biology 7:463-469.
Office Action corresponding to Australian Patent Application No. 2012268970 dated Aug. 27, 2015.
Office Action corresponding to Canadian Patent Application No. 2,837,804 dated May 1, 2015.
Office Action corresponding to Canadian Patent Application No. 2,778,871 dated Jan. 30, 2014.
Office Action corresponding to Chinese Patent Application No. 201080056911.6 dated Jul. 31, 2013. Translation.
Office Action corresponding to European Patent Application No. 00 944 034.8-2401 dated Oct. 7, 2004.
Office action corresponding to European Patent Application No. EP 10 787 815.9-1410 dated Aug. 13, 2013.
Office Action corresponding to Japanese Patent Application No. 2012-504036 dated Aug. 26, 2013.
Office Action corresponding to Japanese Patent Application No. 2012-542583 dated Apr. 22, 2014.
Office Action corresponding to Korean Patent Application No. 10-2011-7018847 dated Jan. 30, 2013. Translation.
Office Action corresponding to Russian Patent Application No. 2012114662/10(022146) dated Sep. 8, 2014. (with Translation).
Office Action corresponding to Russian Patent Application No. 2012115491 dated Dec. 24, 2013.
Office Action corresponding to Russian Patent Application No. 2012114662/10(022146) dated Dec. 18, 2013.
Office Action corresponding to U.S. Appl. No. 12/072,959 dated Jan. 27, 2009.
Office Action corresponding to U.S. Appl. No. 10/030,605 dated Sep. 21, 2004.
Office Action corresponding to U.S. Appl. No. 10/030,605 dated Feb. 15, 2005.
Office Action corresponding to U.S. Appl. No. 10/030,605 dated Aug. 10, 2005.
Office Action corresponding to U.S. Appl. No. 10/030,605 dated Apr. 12, 2006.
Office Action corresponding to U.S. Appl. No. 10/030,605 dated Feb. 28, 2007.
Office Action corresponding to U.S. Appl. No. 10/030,605 dated Nov. 16, 2007.
Office Action corresponding to U.S. Appl. No. 11/656,646 dated Sep. 1, 2009.
Office Action corresponding to U.S. Appl. No. 11/656,646 dated May 25, 2010.
Office Action corresponding to U.S. Appl. No. 10/030,605 dated Jul. 1, 2008.
Office Action corresponding to U.S. Appl. No. 11/656,646 dated Nov. 13, 2009.
Office Action corresponding to U.S. Appl. No. 11/283,332 dated Jan. 9, 2008.
Office Action corresponding to U.S. Appl. No. 11/283,332 dated May 30, 2008.
Office Action corresponding to U.S. Appl. No. 11/283,332 dated Nov. 28, 2008.
Office Action corresponding to U.S. Appl. No. 11/283,332 dated Sep. 4, 2009.
Office Action corresponding to U.S. Appl. No. 11/283,332 dated Sep. 3, 2013.
Office Action corresponding to U.S. Appl. No. 12/072,959 dated Jul. 24, 2008.
Office Action corresponding to U.S. Appl. No. 12/072,959 dated Aug. 30, 2013.
Office Action corresponding to U.S. Appl. No. 11/283,332 dated Mar. 3, 2010.
Office Action corresponding to U.S. Appl. No. 12/072,959 dated Jan. 5, 2010.
Office Action corresponding to U.S. Appl. No. 11/732,632 dated Jun. 3, 2009.
Office Action corresponding to U.S. Appl. No. 11/732,632 dated Aug. 21, 2009.
Office Action corresponding to U.S. Appl. No. 11/732,632 dated Mar. 19, 2010.
Office Action corresponding to U.S. Appl. No. 12/514,550 dated Aug. 3, 2011.
Office Action corresponding to U.S. Appl. No. 12/514,550 dated Sep. 15, 2011.
Office Action corresponding to U.S. Appl. No. 12/514,550 dated Mar. 12, 2012.
Office Action corresponding to U.S. Appl. No. 13/142,195 dated Feb. 11, 2013.
Office Action corresponding to U.S. Appl. No. 13/142,195 dated May 29, 2013.
Office Action corresponding to U.S. Appl. No. 13/142,195 dated Feb. 4, 2014.
Office Action corresponding to U.S. Appl. No. 13/144,809 dated Oct. 18, 2013.
Office Action corresponding to U.S. Appl. No. 13/516,002 dated Jan. 26, 2015.
Office Action corresponding to U.S. Appl. No. 13/516,002 dated Apr. 6, 2015.
Office Action corresponding to U.S. Appl. No. 14/126,341 dated May 1, 2015.
Office Action corresponding to U.S. Appl. No. 14/126,341 dated Sep. 29, 2015.
Office Action corresponding to U.S. Appl. No. 14/126,358 dated Apr. 6, 2016.
Office Action corresponding to U.S. Appl. No. 14/407,213 dated May 25, 2016.
Office Action Restriction Requirement corresponding to U.S. Appl. No. 14/126,358 dated Oct. 28, 2015.
Office Action Restriction Requirement corresponding to U.S. Appl. No. 14/407,213 dated Jan. 21, 2016.
Ohashi et al. (2007) Efficient protein selection based on ribosome display system with purified components. Biochemical and Biophysical Research Communications 352:270-276.
Pack & Pluckthun (1992) A.Miniantibodies: Use of Amphipathic Helices to Produce Functional, Flexibly Linked Dimeric Fv Fragments with High Avidity in *Escherichia coli*. Biochemsitry 31(6):1579-1584.
Raasi Shahri et al. (2004) Binding of polyubiquitin chains to ubiquitin-associated (UBA) domains of HHR23A. J. Mol. Biol. 34:1367-1379.
Rahighi et al. (2009) Specific Recognition of Linear Ubiquitin Chains by NEMO Is Important for NF-κB Activation. Cell 136:1098-1109.
Search Report corresponding to Chinese Patent Application No. 201080056911.6 dated Jun. 14, 2013. Translation.
Skerra (2000) Engineered protein scaffolds for molecular recognition. Journal of Molecular Recognition 13(4):167-187.
Skerra et al. (2007) Alternative non-antibody scaffolds for molecular recognition. Current Opinion in Biotechnology 18(4):295-304.
Smith et al. (1998) Small Binding Proteins Selected from a Conbinatorial Repertoire of Knottins Displayed on Phage. Journal of Molecular Biology 277(2):317-332.

(56) References Cited

OTHER PUBLICATIONS

Susan et al. (2014) Novel Ubiquitin-derived High Affinity Binding Proteins with Tumor Targeting Properties. J of Bio Chem 289(12):8493-8507.
Ubiquitin-like Superfamily (2004) pp. 1-4.
Weidle et al. (2013) The Emerging Role of New Protein Scaffold-based Agents for Treament of Cancer. Caner Genomics & Proteomics 10(4):155-168.
Wells & Lowmann (1992).Rapid evolution of peptide and protein binding properties in vitro. Current Opinion in Biotechnology 3:355-362.
Wells (1990) Additivity of Mutational Effects in Proteins. Biochemistry 29(37):8509-8517.
Yeh et al. (2000) Ubiquitin-like proteins: new wines in new bottles. Gene 248(1-2):1-14.
Zahnd et al. (2007) Ribosome display: selecting and evolving proteins in vitro that specifically bind to a target. Nature Methods 4(3):269-279.
Zhang et al. (1997) Directed evolution of a fucosidase from a galactosidase by DNA shuffling and screening. PNAS 94:4504-4509.
Office Action (Restriction Requirement) corresponding to U.S. Appl. No. 15/549,022 dated May 3, 2018.
Office Action (Restriction Requirement) corresponding to U.S. Appl. No. 15/549,022 dated Nov. 8, 2018.
Office Action corresponding to U.S. Appl. No. 15/744,054 dated Mar. 14, 2019.
Office Action Restriction Requirement corresponding to U.S. Appl. No. 15/548,976 dated Jun. 14, 2019.
Office Action corresponding to U.S. Appl. No. 15/744,054 dated Jul. 30, 2019.
International Preliminary Report on Patentability corresponding to International Patent Application No. PCT/EP2016/067216 dated Jan. 23, 2018.
International Search Report corresponding to International Application No. PCT/EP2016/067207 dated Sep. 29, 2016.
International Search Report and Written Opinion corresponding to International Application No. PCT/EP2016/067216 dated Oct. 12, 2016.
International Search Report and Written Opinion corresponding to International Application No. PCT/EP2016/066774 dated Sep. 14, 2016.
Lorey et al. (2014) Novel ubiquitin-derived high affinity binding proteins with tumor targeting properties. Journal of Biological Chemistry. 289(12):8493-8507.

* cited by examiner

FIG. 1

| SEQ ID NO: | Affilin | Binding Cartridge | additional exchanges | Biacore (KD_hEGFR-Fc) | DSF(°C) | C-term exchanges (Pos. 62-66) |
|---|---|---|---|---|---|---|
| 8 | 139787 | (EYEPEW)GEPDI | | 150 nM | 79 | GEPDI |
| 9 | 139801 | (ESDWYT)GHPDI | | 220 nM | n.d. | GHPDI |
| 10 | 139754 | (PWRGYD)IHADI | | 537 nM | n.d. | IHADI |
| 11 | 139827 | (EEDYYN)HHPDI | | 550 nM | n.d. | HHPDI |
| 12 | 139772 | (MEQAGY)QAPDI | | 61 nM | 70 | QAPDI |
| 13 | 142277 | (EYEPEY)QHPDI | | 0,97 nM | n.d. | QHPDI |
| 14 | 139762 | (EGDQWY)QHPDI | | 184 nM | n.d. | QHPDI |
| 15 | 139755 | (ESERWY)QHPDI | | 243 nM | n.d. | QHPDI |
| 16 | 139797 | (DHEMNY)QHPDI | | 274 nM | 74 | QHPDI |
| 17 | 142304 | (EYSYMY)QNPDI | | 2 nM | 75 | QNPDI |
| 18 | 142245 | (EQDDYH)QNPDI | | 19 nM | n.d. | QNPDI |
| 19 | 142259 | (EQDGYH)QNPDI | | 33 nM | n.d. | QNPDI |
| 20 | 139811 | (QDPYRY)QNPDI | | 57 nM | n.d. | QNPDI |
| 21 | 139824 | (PPSMNW)QNPDI | | 80 nM | n.d. | QNPDI |
| 22 | 139814 | (MENYWG)QNPDI | | 86 nM | 73 | QNPDI |
| 23 | 139781 | (EPTMQH)QNPDI | | 90 nM | 72 | QNPDI |
| 24 | 139793 | (EPDRQY)QNPDI | | 127 nM | n.d. | QNPDI |
| 25 | 139817 | (EAMGWD)QNPDI | P38L | 130 nM | 74 | QNPDI |
| 26 | 139816 | (YPQREY)QNPDI | | 143 nM | n.d. | QNPDI |
| 27 | 139822 | (PQDMHQ)QNPDI | | 160 nM | n.d. | QNPDI |
| 28 | 139765 | (PNMEYH)QNPDI | | 162 nM | n.d. | QNPDI |
| 29 | 142232 | (WDPYQY)QNPDI | P3S | 169 nM | n.d. | QNPDI |
| 30 | 139830 | (PQDMHQ)QNPDI | | 174 nM | n.d. | QNPDI |
| 31 | 139784 | (QWEEYS)QNPDI | | 413 nM | 77 | QNPDI |
| 32 | 142289 | (DDKGYD)QNPDI | | 703 nM | 74 | QNPDI |
| 33 | 139808 | (QYSEDG)QQPDI | V5L,T12I | 133 nM | n.d. | QQPDI |
| 34 | 139829 | (PEQHMY)RHPDI | T12I | 60 nM | 78 | RHPDI |
| 35 | 139763 | (QETYYY)RHPDI | | 64 nM | n.d. | RHPDI |
| 36 | 142299 | (QQSEYS)RHPDI | | 91 nM | n.d. | RHPDI |
| 37 | 139773 | (EYQAPN)RHPDI | | 100 nM | 70 | RHPDI |
| 38 | 139788 | (EQSQYG)RHPDI | | 180 nM | 74 | RHPDI |
| 39 | 139819 | (YNPMRY)RNPDI | | 19 nM | 74 | RNPDI |
| 40 | 142269 | (QSDPHY)RNPDI | | 48 nM | n.d. | RNPDI |
| 41 | 139767 | (APQDMY)RNPDI | | 70 nM | n.d. | RNPDI |
| 42 | 139775 | (QMSDMR)RNPDI | | 100 nM | 65 | RNPDI |
| 43 | 139771 | (DRDMYQ)RNPDI | | 106 nM | n.d. | RNPDI |
| 44 | 139799 | (SDYYMN)RNPDI | | 126 nM | n.d. | RNPDI |
| 45 | 139832 | (DQPDWY)RNPDI | | 140 nM | n.d. | RNPDI |
| 46 | 139785 | (AGDYYN)RNPDI | | 176 nM | n.d. | RNPDI |
| 47 | 139796 | (PYEQGY)RNPDI | | 240 nM | 77 | RNPDI |
| 48 | 139760 | (EHEKWA)RNPDI | | 244 nM | n.d. | RNPDI |
| 49 | 139791 | (PWRGYD)RRVDV | | 175 nM | 76 | RRVDV |
| 50 | 139756 | (TWEPEY)SAPDI | | 66 nM | 75 | SAPDI |
| 51 | 139826 | (EHDAYG)THPDI | R74C | 110 nM | 63 | THPDI |
| 52 | 142298 | (GGDHGY)VNPDI | | 9 nM | 74 | VNPDI |
| 53 | 139895 | ATQNPDI-DHRAGQT | | 452 nM | 68 | QNPDI |
| 54 | 139901 | HDRHPDI-NFYNGMF | | 61 nM | 63 | RHPDI |

FIG. 1 (cont'd)

| 55 | 139851 | HMQHPDI-TQSREPA | | 534 nM | n.d. | QHPDI |
|---|---|---|---|---|---|---|
| 56 | 139959 | HMRNPDI-VFTQWTP | | 566 nM | 61 | RNPDI |
| 57 | 139853 | HNQSPDI-DAPEGHT | | 403 nM | 73 | QSPDI |
| 58 | 139864 | HPRNPDI-HMGAGTM | | 536 nM | 74 | RNPDI |
| 59 | 140094 | HQTSPDI-ISPRAAS | | 650 nM | 69 | TSPDI |
| 60 | 140102 | HSRHPDI-TTQPSKL | | 480 nM | n.d. | RHPDI |
| 61 | 139961 | HTRHPDI-SFVAHNM | | 450 nM | 62 | RHPDI |
| 62 | 139848 | HVRNPDI-KPPARRS | | 488 nM | 64 | RNPDI |
| 63 | 139935 | HWQHPDI-DPPEHNA | | 530 nM | 68 | QHPDI |
| 64 | 139880 | HWRHPDI-RPHRSAM | | 574 nM | 74 | RHPDI |
| 65 | 139907 | HWSHPDI-VTANRAR | | 473 nM | 70 | SHPDI |
| 66 | 140077 | HYRHPDI-HNGARTS | | 660 nM | 67 | RHPDI |
| 67 | 140123 | YNQSPDI-LDTMPPP | | 600 nM | 62 | QSPDI |
| 68 | 139882 | YNRNPDI-DYGYEPA | | 426 nM | n.d. | RNPDI |
| 69 | 138838 | YNRNPDI-HIEGERD | | 615 nM | 58 | RNPDI |
| 70 | 139923 | YPRHPDI-DYGYEPA | F4S,V5L,I13L,V17L,2. moiety: V70L | 532 nM | n.d. | RHPDI |
| 71 | 138819 | YTQNPDI-YIAQHSE | | 741 nM | 55 | QNPDI |
| 72 | 140005 | YVRNPDI-EDQKNAQ | | 440 nM | 66 | RNPDI |
| 73 | 138845 | YNRNPDI-HIGGERD | | 561 nM | 58 | RNPDI |
| 76 | 139989 | VMEWYTN-WTLHGQW | | 61 nM | 60 | EWYTN |
| 77 | 138840 | HLNFKLS-HQGWQAP | Q2V,F4W | 5,7 µM | n.d. | NFKLS |

FIG. 12
FIG. 12A. Binding of Affilin 139819 (homodimer) to CHO-K1 cells
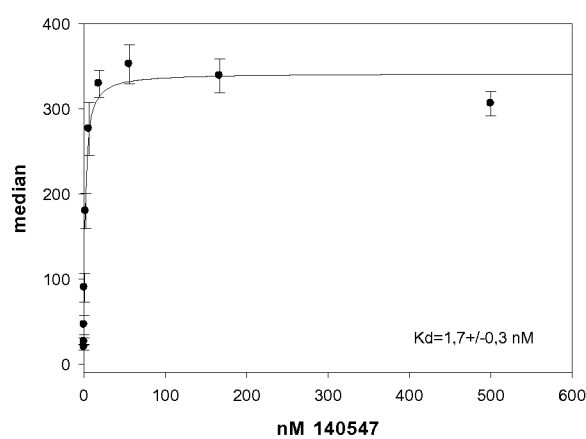
FIG. 12B. Binding of Affilin 139819 to CHO-K1 cells
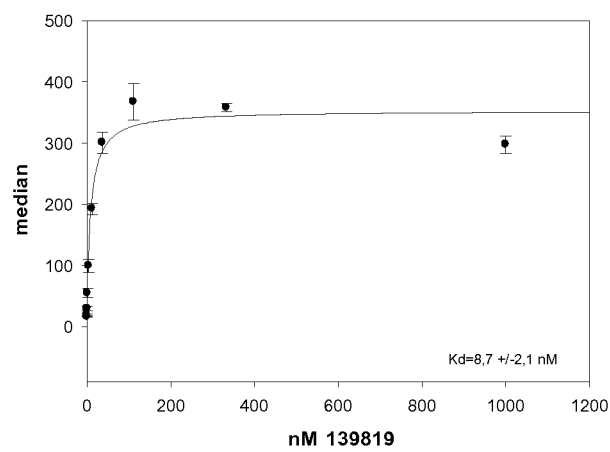

FIG. 12C. Binding of Affilin 139819 (homodimer) to A549 cells
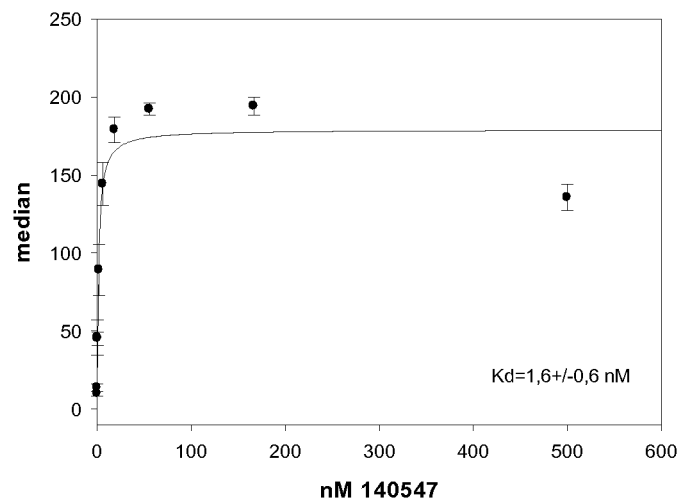
FIG. 12D. Binding of Affilin 139819 to A549 cells
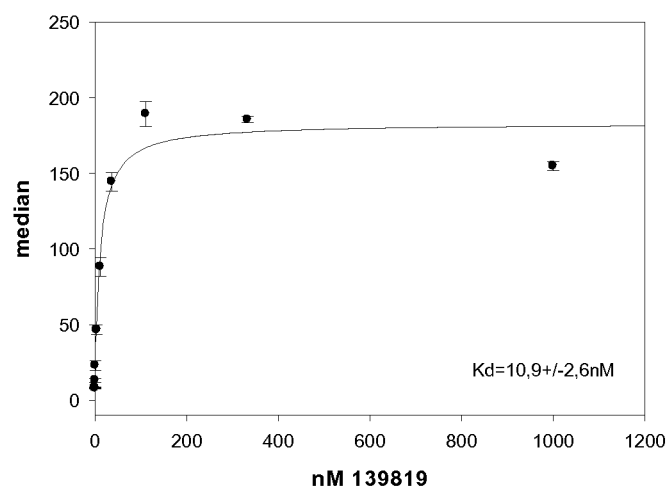

SEQUENCE LISTING

```
<160> NUMBER OF SEQ ID NOS: 114

<210> SEQ ID NO 1
<211> LENGTH: 76
<212> TYPE: PRT
<213> ORGANISM: Artificial Sequence
<220> FEATURE:
<223> OTHER INFORMATION: Artificial Ubiquitin Sequence

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 76
<212> TYPE: PRT
<213> ORGANISM: Artificial Sequence
<220> FEATURE:
<223> OTHER INFORMATION: Artificial Ubiquitin reference Sequence

<400> SEQUENCE: 2

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala
65                  70                  75

<210> SEQ ID NO 3
<211> LENGTH: 76
<212> TYPE: PRT
<213> ORGANISM: Artificial Sequence
<220> FEATURE:
<223> OTHER INFORMATION: Artificial Ubiquitin reference Sequence
<220> FEATURE:
<221> NAME/KEY: misc_feature
<222> LOCATION: (62)..(66)
<223> OTHER INFORMATION: Xaa can be any naturally occurring amino acid

<400> SEQUENCE: 3

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Xaa Xaa Xaa
    50                  55                  60

Xaa Xaa Leu His Leu Val Leu Arg Leu Arg Ala Ala
65                  70                  75

<210> SEQ ID NO 4
<211> LENGTH: 152
<212> TYPE: PRT
<213> ORGANISM: Artificial Sequence
<220> FEATURE:
<223> OTHER INFORMATION: Ubiquitin reference clone 139090 (di-ubiquitin)
      Sequence

<400> SEQUENCE: 4

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
 50                  55                  60

Ser Thr Leu His Leu Val Leu Arg Leu Arg Ala Ala Met Gln Ile Phe
 65                  70                  75                  80

Val Lys Thr Leu Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
             100                 105                 110

Pro Pro Asp Gln Gln Arg Leu Ile Phe Ala Gly Lys Gln Leu Glu Asp
         115                 120                 125

Gly Arg Thr Leu Ser Asp Tyr Asn Ile Gln Lys Glu Ser Thr Leu His
     130                 135                 140

Leu Val Leu Arg Leu Arg Ala Ala
145                 150

<210> SEQ ID NO 5
<211> LENGTH: 468
<212> TYPE: PRT
<213> ORGANISM: Artificial Sequence
<220> FEATURE:
<223> OTHER INFORMATION: Cetuximab HC Sequence

<400> SEQUENCE: 5

Met Ala Val Leu Gly Leu Leu Phe Cys Leu Val Thr Phe Pro Ser Cys
  1               5                  10                  15

Val Leu Ser Gln Val Gln Leu Lys Gln Ser Gly Pro Gly Leu Val Gln
                 20                  25                  30

Pro Ser Gln Ser Leu Ser Ile Thr Cys Thr Val Ser Gly Phe Ser Leu
             35                  40                  45

Thr Asn Tyr Gly Val His Trp Val Arg Gln Ser Pro Lys Gly Leu
 50                  55                  60

Glu Trp Leu Gly Val Ile Trp Ser Gly Gly Asn Thr Asp Tyr Asn Thr
 65                  70                  75                  80

Pro Phe Thr Ser Arg Leu Ser Ile Asn Lys Asp Asn Ser Lys Ser Gln
                 85                  90                  95

Val Phe Phe Lys Met Asn Ser Leu Gln Ser Asn Asp Thr Ala Ile Tyr
             100                 105                 110

Tyr Cys Ala Arg Ala Leu Thr Tyr Tyr Asp Tyr Glu Phe Ala Tyr Trp
         115                 120                 125

Gly Gln Gly Thr Leu Val Thr Val Ser Ala Ala Ser Thr Lys Gly Pro
     130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                 165                 170                 175

Val Ser Trp Asn Ser Gly Ala Leu Thr Ser Gly Val His Thr Phe Pro
             180                 185                 190

Ala Val Leu Gln Ser Ser Gly Leu Tyr Ser Leu Ser Ser Val Val Thr
         195                 200                 205

Val Pro Ser Ser Ser Leu Gly Thr Gln Thr Tyr Ile Cys Asn Val Asn
     210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                 245                 250                 255

```
Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 6
<211> LENGTH: 234
<212> TYPE: PRT
<213> ORGANISM: Artificial Sequence
<220> FEATURE:
<223> OTHER INFORMATION: Cetuximab LC Sequence

<400> SEQUENCE: 6

Met Val Ser Thr Pro Gln Phe Leu Val Phe Leu Leu Phe Trp Ile Pro
1               5                   10                  15

Ala Ser Arg Ser Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
            85                  90                  95

Ser Val Glu Ser Glu Asp Ile Ala Asp Tyr Tyr Cys Gln Gln Asn Asn
        100                 105                 110

Asn Trp Pro Thr Thr Phe Gly Ala Gly Thr Lys Leu Glu Leu Lys Arg
    115                 120                 125

Thr Val Ala Ala Pro Ser Val Phe Ile Phe Pro Pro Ser Asp Glu Gln
130                 135                 140
```

```
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 7
<211> LENGTH: 155
<212> TYPE: PRT
<213> ORGANISM: Artificial Sequence
<220> FEATURE:
<223> OTHER INFORMATION: Unmodified ubiquitin clone 64156 Sequence

<400> SEQUENCE: 7

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala Gly Ile Gly Met
65                  70                  75                  80

Gln Ile Phe Val Lys Thr Leu Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gln Lys Glu Ser
    130                 135                 140

Thr Leu His Leu Val Leu Arg Leu Arg Ala Ala
145                 150                 155

<210> SEQ ID NO 8
<211> LENGTH: 82
<212> TYPE: PRT
<213> ORGANISM: Artificial Sequence
<220> FEATURE:
<223> OTHER INFORMATION: Affilin 139787 Sequence

<400> SEQUENCE: 8

Met Gln Ile Phe Val Lys Thr Leu Thr Glu Tyr Glu Pro Glu Trp Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
```

Tyr Asn Ile Gly Glu Pro Asp Ile Leu His Leu Val Leu Arg Leu Arg
65                  70                  75                  80

Ala Ala

<210> SEQ ID NO 9
<211> LENGTH: 82
<212> TYPE: PRT
<213> ORGANISM: Artificial Sequence
<220> FEATURE:
<223> OTHER INFORMATION: Affilin 139801 Sequence

<400> SEQUENCE: 9

Met Gln Ile Phe Val Lys Thr Leu Thr Glu Ser Asp Trp Tyr Thr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gly His Pro Asp Ile Leu His Leu Val Leu Arg Leu Arg
65                  70                  75                  80

Ala Ala

<210> SEQ ID NO 10
<211> LENGTH: 82
<212> TYPE: PRT
<213> ORGANISM: Artificial Sequence
<220> FEATURE:
<223> OTHER INFORMATION: Affilin 139754 Sequence

<400> SEQUENCE: 10

Met Gln Ile Phe Val Lys Thr Leu Thr Pro Trp Arg Gly Tyr Asp Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Ile His Ala Asp Ile Leu His Leu Val Leu Arg Leu Arg
65                  70                  75                  80

Ala Ala

<210> SEQ ID NO 11
<211> LENGTH: 82
<212> TYPE: PRT
<213> ORGANISM: Artificial Sequence
<220> FEATURE:
<223> OTHER INFORMATION: Affilin 139827 Sequence

<400> SEQUENCE: 11

Met Gln Ile Phe Val Lys Thr Leu Thr Glu Glu Asp Tyr Tyr Asn Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

-continued

Leu Ile Trp Ala Gly Lys Gln Leu Glu Asp Gly Arg Thr Leu Ser Asp
        50                  55                  60

Tyr Asn Ile His His Pro Asp Ile Leu His Leu Val Leu Arg Leu Arg
65                  70                  75                  80

Ala Ala

<210> SEQ ID NO 12
<211> LENGTH: 82
<212> TYPE: PRT
<213> ORGANISM: Artificial Sequence
<220> FEATURE:
<223> OTHER INFORMATION: Affilin 139779 Sequence

<400> SEQUENCE: 12

Met Gln Ile Phe Val Lys Thr Leu Thr Met Glu Gln Ala Gly Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
        50                  55                  60

Tyr Asn Ile Gln Ala Pro Asp Ile Leu His Leu Val Leu Arg Leu Arg
65                  70                  75                  80

Ala Ala

<210> SEQ ID NO 13
<211> LENGTH: 82
<212> TYPE: PRT
<213> ORGANISM: Artificial Sequence
<220> FEATURE:
<223> OTHER INFORMATION: Affilin 142277 Sequence

<400> SEQUENCE: 13

Met Gln Ile Phe Val Lys Thr Leu Thr Glu Tyr Glu Pro Glu Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
        50                  55                  60

Tyr Asn Ile Gln His Pro Asp Ile Leu His Leu Val Leu Arg Leu Arg
65                  70                  75                  80

Ala Ala

<210> SEQ ID NO 14
<211> LENGTH: 82
<212> TYPE: PRT
<213> ORGANISM: Artificial Sequence
<220> FEATURE:
<223> OTHER INFORMATION: Affilin 139755 Sequence

<400> SEQUENCE: 14

Met Gln Ile Phe Val Lys Thr Leu Thr Glu Ser Glu Arg Trp Tyr Gly
1               5                   10                  15

Lys Thr Ile Thr Leu Glu Val Glu Pro Ser Asp Thr Ile Glu Asn Val
            20                  25                  30

-continued

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
 50                  55                  60

Tyr Asn Ile Gln His Pro Asp Ile Leu His Leu Val Leu Arg Leu Arg
 65                  70                  75                  80

Ala Ala

<210> SEQ ID NO 15
<211> LENGTH: 82
<212> TYPE: PRT
<213> ORGANISM: Artificial Sequence
<220> FEATURE:
<223> OTHER INFORMATION: Affilin 139797 Sequence

<400> SEQUENCE: 15

Met Gln Ile Phe Val Lys Thr Leu Thr Asp His Glu Met Asn Tyr Gly
 1               5                  10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
 50                  55                  60

Tyr Asn Ile Gln His Pro Asp Ile Leu His Leu Val Leu Arg Leu Arg
 65                  70                  75                  80

Ala Ala

<210> SEQ ID NO 16
<211> LENGTH: 82
<212> TYPE: PRT
<213> ORGANISM: Artificial Sequence
<220> FEATURE:
<223> OTHER INFORMATION: 139831 Sequence

<400> SEQUENCE: 16

Met Gln Ile Phe Val Lys Thr Leu Thr Glu Gly Asp Gln Trp Tyr Gly
 1               5                  10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
 50                  55                  60

Tyr Asn Ile Gln His Pro Asp Ile Leu His Leu Val Leu Arg Leu Arg
 65                  70                  75                  80

Ala Ala

<210> SEQ ID NO 17
<211> LENGTH: 82
<212> TYPE: PRT
<213> ORGANISM: Artificial Sequence
<220> FEATURE:
<223> OTHER INFORMATION: Affilin 142304 Sequence

<400> SEQUENCE: 17

Met Gln Ile Phe Val Lys Thr Leu Thr Glu Tyr Ser Tyr Met Tyr Gly
 1               5                  10                  15

Lys Thr Ile Thr Leu Glu Val Glu Pro Ser Asp Thr Ile Glu Asn Val

```
                    20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 18
<211> LENGTH: 82
<212> TYPE: PRT
<213> ORGANISM: Artificial Sequence
<220> FEATURE:
<223> OTHER INFORMATION: Affilin 142245 Sequence

<400> SEQUENCE: 18

Met Gln Ile Phe Val Lys Thr Leu Thr Glu Gln Asp Asp Tyr His Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 19
<211> LENGTH: 82
<212> TYPE: PRT
<213> ORGANISM: Artificial Sequence
<220> FEATURE:
<223> OTHER INFORMATION: Affilin 142259 Sequence

<400> SEQUENCE: 19

Met Gln Ile Phe Val Lys Thr Leu Thr Glu Gln Asp Gly Tyr His Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 20
<211> LENGTH: 82
<212> TYPE: PRT
<213> ORGANISM: Artificial Sequence
<220> FEATURE:
<223> OTHER INFORMATION: Affilin 139811 Sequence

<400> SEQUENCE: 20

Met Gln Ile Phe Val Lys Thr Leu Thr Gln Asp Pro Tyr Arg Tyr Gly
1               5                   10                  15
```

-continued

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 21
<211> LENGTH: 82
<212> TYPE: PRT
<213> ORGANISM: Artificial Sequence
<220> FEATURE:
<223> OTHER INFORMATION: Affilin 139824 Sequence

<400> SEQUENCE: 21

Met Gln Ile Phe Val Lys Thr Leu Thr Pro Pro Ser Met Asn Trp Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 22
<211> LENGTH: 82
<212> TYPE: PRT
<213> ORGANISM: Artificial Sequence
<220> FEATURE:
<223> OTHER INFORMATION: Affilin 139828 Sequence

<400> SEQUENCE: 22

Met Gln Ile Phe Val Lys Thr Leu Thr Met Glu Asn Tyr Trp Gly Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 23
<211> LENGTH: 82
<212> TYPE: PRT
<213> ORGANISM: Artificial Sequence
<220> FEATURE:
<223> OTHER INFORMATION: Affilin 139781 Sequence

<400> SEQUENCE: 23

```
Met Gln Ile Phe Val Lys Thr Leu Thr Glu Pro Thr Met Gln His Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala
```

<210> SEQ ID NO 24
<211> LENGTH: 82
<212> TYPE: PRT
<213> ORGANISM: Artificial Sequence
<220> FEATURE:
<223> OTHER INFORMATION: Affilin 139793 Sequence

<400> SEQUENCE: 24

```
Met Gln Ile Phe Val Lys Thr Leu Thr Glu Pro Asp Arg Gln Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala
```

<210> SEQ ID NO 25
<211> LENGTH: 82
<212> TYPE: PRT
<213> ORGANISM: Artificial Sequence
<220> FEATURE:
<223> OTHER INFORMATION: Affilin 139817 Sequence

<400> SEQUENCE: 25

```
Met Gln Ile Phe Val Lys Thr Leu Thr Glu Ala Met Gly Trp Asp Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Leu Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala
```

<210> SEQ ID NO 26
<211> LENGTH: 82
<212> TYPE: PRT
<213> ORGANISM: Artificial Sequence
<220> FEATURE:
<223> OTHER INFORMATION: Affilin 139816 Sequence

```
<400> SEQUENCE: 26

Met Gln Ile Phe Val Lys Thr Leu Thr Tyr Pro Gln Arg Glu Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 27
<211> LENGTH: 82
<212> TYPE: PRT
<213> ORGANISM: Artificial Sequence
<220> FEATURE:
<223> OTHER INFORMATION: Affilin 139822 Sequence

<400> SEQUENCE: 27

Met Gln Ile Phe Val Lys Thr Leu Thr Pro Gln Asp Met His Gln Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 28
<211> LENGTH: 82
<212> TYPE: PRT
<213> ORGANISM: Artificial Sequence
<220> FEATURE:
<223> OTHER INFORMATION: Affilin 139765 Sequence

<400> SEQUENCE: 28

Met Gln Ile Phe Val Lys Thr Leu Thr Pro Asn Met Glu Tyr His Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 29
<211> LENGTH: 82
<212> TYPE: PRT
<213> ORGANISM: Artificial Sequence
<220> FEATURE:
```

-continued

<223> OTHER INFORMATION: Affilin 142232 Sequence

<400> SEQUENCE: 29

Met Gln Ile Phe Val Lys Thr Leu Thr Trp Asp Pro Tyr Gln Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Ser Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 30
<211> LENGTH: 82
<212> TYPE: PRT
<213> ORGANISM: Artificial Sequence
<220> FEATURE:
<223> OTHER INFORMATION: Affilin 139830 Sequence

<400> SEQUENCE: 30

Met Gln Ile Phe Val Lys Thr Leu Thr Pro Gln Asp Met His Gln Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 31
<211> LENGTH: 82
<212> TYPE: PRT
<213> ORGANISM: Artificial Sequence
<220> FEATURE:
<223> OTHER INFORMATION: Affilin 139784 Sequence

<400> SEQUENCE: 31

Met Gln Ile Phe Val Lys Thr Leu Thr Gln Trp Glu Glu Tyr Ser Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala

<210> SEQ ID NO 32
<211> LENGTH: 82
<212> TYPE: PRT

<213> ORGANISM: Artificial Sequence
<220> FEATURE:
<223> OTHER INFORMATION: Affilin 142289 Sequence

<400> SEQUENCE: 32

```
Met Gln Ile Phe Val Lys Thr Leu Thr Asp Asp Lys Gly Tyr Asp Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Ile Leu His Leu Val Leu Arg Leu Arg
65                  70                  75                  80

Ala Ala
```

<210> SEQ ID NO 33
<211> LENGTH: 82
<212> TYPE: PRT
<213> ORGANISM: Artificial Sequence
<220> FEATURE:
<223> OTHER INFORMATION: Affilin 139808 Sequence

<400> SEQUENCE: 33

```
Met Gln Ile Phe Leu Lys Thr Leu Thr Gln Tyr Ser Glu Asp Gly Gly
1               5                   10                  15

Lys Ile Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Gln Pro Asp Ile Leu His Leu Val Leu Arg Leu Arg
65                  70                  75                  80

Ala Ala
```

<210> SEQ ID NO 34
<211> LENGTH: 82
<212> TYPE: PRT
<213> ORGANISM: Artificial Sequence
<220> FEATURE:
<223> OTHER INFORMATION: Affilin 139829 Sequence

<400> SEQUENCE: 34

```
Met Gln Ile Phe Val Lys Thr Leu Thr Pro Glu Gln His Met Tyr Gly
1               5                   10                  15

Lys Ile Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg His Pro Asp Ile Leu His Leu Val Leu Arg Leu Arg
65                  70                  75                  80

Ala Ala
```

<210> SEQ ID NO 35

```
<211> LENGTH: 82
<212> TYPE: PRT
<213> ORGANISM: Artificial Sequence
<220> FEATURE:
<223> OTHER INFORMATION: Affilin 139763 Sequence

<400> SEQUENCE: 35

Met Gln Ile Phe Val Lys Thr Leu Thr Gln Glu Thr Tyr Tyr Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg His Pro Asp Ile Leu His Leu Val Leu Arg Leu Arg
65                  70                  75                  80

Ala Ala

<210> SEQ ID NO 36
<211> LENGTH: 82
<212> TYPE: PRT
<213> ORGANISM: Artificial Sequence
<220> FEATURE:
<223> OTHER INFORMATION: Affilin 142299 Sequence

<400> SEQUENCE: 36

Met Gln Ile Phe Val Lys Thr Leu Thr Gln Gln Ser Glu Tyr Ser Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg His Pro Asp Ile Leu His Leu Val Leu Arg Leu Arg
65                  70                  75                  80

Ala Ala

<210> SEQ ID NO 37
<211> LENGTH: 82
<212> TYPE: PRT
<213> ORGANISM: Artificial Sequence
<220> FEATURE:
<223> OTHER INFORMATION: Affilin 139773 Sequence

<400> SEQUENCE: 37

Met Gln Ile Phe Val Lys Thr Leu Thr Glu Tyr Gln Ala Pro Asn Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg His Pro Asp Ile Leu His Leu Val Leu Arg Leu Arg
65                  70                  75                  80

Ala Ala
```

<210> SEQ ID NO 38
<211> LENGTH: 82
<212> TYPE: PRT
<213> ORGANISM: Artificial Sequence
<220> FEATURE:
<223> OTHER INFORMATION: Affilin 139788 Sequence

<400> SEQUENCE: 38

```
Met Gln Ile Phe Val Lys Thr Leu Thr Glu Gln Ser Gln Tyr Gly Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg His Pro Asp Ile Leu His Leu Val Leu Arg Leu Arg
65                  70                  75                  80

Ala Ala
```

<210> SEQ ID NO 39
<211> LENGTH: 82
<212> TYPE: PRT
<213> ORGANISM: Artificial Sequence
<220> FEATURE:
<223> OTHER INFORMATION: Affilin 139819 Sequence

<400> SEQUENCE: 39

```
Met Gln Ile Phe Val Lys Thr Leu Thr Tyr Asn Pro Met Arg Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg Asn Pro Asp Ile Leu His Leu Val Leu Arg Leu Arg
65                  70                  75                  80

Ala Ala
```

<210> SEQ ID NO 40
<211> LENGTH: 82
<212> TYPE: PRT
<213> ORGANISM: Artificial Sequence
<220> FEATURE:
<223> OTHER INFORMATION: Affilin 142269 Sequence

<400> SEQUENCE: 40

```
Met Gln Ile Phe Val Lys Thr Leu Thr Gln Ser Asp Pro His Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg Asn Pro Asp Ile Leu His Leu Val Leu Arg Leu Arg
65                  70                  75                  80
```

Ala Ala

<210> SEQ ID NO 41
<211> LENGTH: 82
<212> TYPE: PRT
<213> ORGANISM: Artificial Sequence
<220> FEATURE:
<223> OTHER INFORMATION: Affilin 139767 Sequence

<400> SEQUENCE: 41

```
Met Gln Ile Phe Val Lys Thr Leu Thr Ala Pro Gln Asp Met Tyr Gly
1               5                   10                  15
Lys Thr Ile Thr Leu Glu Val Glu Pro Ser Asp Thr Ile Glu Asn Val
            20                  25                  30
Lys Ala Lys Ile Gln Asp Lys Glu Gly Ile Pro Pro Asp Gln Gln Arg
        35                  40                  45
Leu Ile Trp Ala Gly Lys Gln Leu Glu Asp Gly Arg Thr Leu Ser Asp
    50                  55                  60
Tyr Asn Ile Arg Asn Pro Asp Ile Leu His Leu Val Leu Arg Leu Arg
65                  70                  75                  80
Ala Ala
```

<210> SEQ ID NO 42
<211> LENGTH: 82
<212> TYPE: PRT
<213> ORGANISM: Artificial Sequence
<220> FEATURE:
<223> OTHER INFORMATION: Affilin 139775 Sequence

<400> SEQUENCE: 42

```
Met Gln Ile Phe Val Lys Thr Leu Thr Gln Met Ser Asp Met Arg Gly
1               5                   10                  15
Lys Thr Ile Thr Leu Glu Val Glu Pro Ser Asp Thr Ile Glu Asn Val
            20                  25                  30
Lys Ala Lys Ile Gln Asp Lys Glu Gly Ile Pro Pro Asp Gln Gln Arg
        35                  40                  45
Leu Ile Trp Ala Gly Lys Gln Leu Glu Asp Gly Arg Thr Leu Ser Asp
    50                  55                  60
Tyr Asn Ile Arg Asn Pro Asp Ile Leu His Leu Val Leu Arg Leu Arg
65                  70                  75                  80
Ala Ala
```

<210> SEQ ID NO 43
<211> LENGTH: 82
<212> TYPE: PRT
<213> ORGANISM: Artificial Sequence
<220> FEATURE:
<223> OTHER INFORMATION: Affilin 139771 Sequence

<400> SEQUENCE: 43

```
Met Gln Ile Phe Val Lys Thr Leu Thr Asp Arg Asp Met Tyr Gln Gly
1               5                   10                  15
Lys Thr Ile Thr Leu Glu Val Glu Pro Ser Asp Thr Ile Glu Asn Val
            20                  25                  30
Lys Ala Lys Ile Gln Asp Lys Glu Gly Ile Pro Pro Asp Gln Gln Arg
        35                  40                  45
Leu Ile Trp Ala Gly Lys Gln Leu Glu Asp Gly Arg Thr Leu Ser Asp
    50                  55                  60
Tyr Asn Ile Arg Asn Pro Asp Ile Leu His Leu Val Leu Arg Leu Arg
```

65                   70                 75                 80

Ala Ala

<210> SEQ ID NO 44
<211> LENGTH: 82
<212> TYPE: PRT
<213> ORGANISM: Artificial Sequence
<220> FEATURE:
<223> OTHER INFORMATION: Affilin 139799 Sequence

<400> SEQUENCE: 44

Met Gln Ile Phe Val Lys Thr Leu Thr Ser Asp Tyr Tyr Met Asn Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg Asn Pro Asp Ile Leu His Leu Val Leu Arg Leu Arg
65                  70                  75                  80

Ala Ala

<210> SEQ ID NO 45
<211> LENGTH: 82
<212> TYPE: PRT
<213> ORGANISM: Artificial Sequence
<220> FEATURE:
<223> OTHER INFORMATION: Affilin 139832 Sequence

<400> SEQUENCE: 45

Met Gln Ile Phe Val Lys Thr Leu Thr Asp Gln Pro Asp Trp Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg Asn Pro Asp Ile Leu His Leu Val Leu Arg Leu Arg
65                  70                  75                  80

Ala Ala

<210> SEQ ID NO 46
<211> LENGTH: 82
<212> TYPE: PRT
<213> ORGANISM: Artificial Sequence
<220> FEATURE:
<223> OTHER INFORMATION: Affilin 139785 Sequence

<400> SEQUENCE: 46

Met Gln Ile Phe Val Lys Thr Leu Thr Ala Gly Asp Tyr Tyr Asn Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

-continued

Tyr Asn Ile Arg Asn Pro Asp Ile Leu His Leu Val Leu Arg Leu Arg
65                  70                  75                  80

Ala Ala

<210> SEQ ID NO 47
<211> LENGTH: 82
<212> TYPE: PRT
<213> ORGANISM: Artificial Sequence
<220> FEATURE:
<223> OTHER INFORMATION: Affilin 139796 Sequence

<400> SEQUENCE: 47

Met Gln Ile Phe Val Lys Thr Leu Thr Pro Tyr Glu Gln Gly Tyr Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
        50                  55                  60

Tyr Asn Ile Arg Asn Pro Asp Ile Leu His Leu Val Leu Arg Leu Arg
65                  70                  75                  80

Ala Ala

<210> SEQ ID NO 48
<211> LENGTH: 82
<212> TYPE: PRT
<213> ORGANISM: Artificial Sequence
<220> FEATURE:
<223> OTHER INFORMATION: Affilin 139760 Sequence

<400> SEQUENCE: 48

Met Gln Ile Phe Val Lys Thr Leu Thr Glu His Glu Lys Trp Ala Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
        50                  55                  60

Tyr Asn Ile Arg Asn Pro Asp Ile Leu His Leu Val Leu Arg Leu Arg
65                  70                  75                  80

Ala Ala

<210> SEQ ID NO 49
<211> LENGTH: 82
<212> TYPE: PRT
<213> ORGANISM: Artificial Sequence
<220> FEATURE:
<223> OTHER INFORMATION: Affilin 139791 Sequence

<400> SEQUENCE: 49

Met Gln Ile Phe Val Lys Thr Leu Thr Pro Trp Arg Gly Tyr Asp Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
50                  55                  60

Tyr Asn Ile Arg Arg Val Asp Val Leu His Leu Val Leu Arg Leu Arg
65                  70                  75                  80

Ala Ala

<210> SEQ ID NO 50
<211> LENGTH: 82
<212> TYPE: PRT
<213> ORGANISM: Artificial Sequence
<220> FEATURE:
<223> OTHER INFORMATION: Affilin 139756 Sequence

<400> SEQUENCE: 50

Met Gln Ile Phe Val Lys Thr Leu Thr Thr Trp Glu Pro Glu Tyr Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
50                  55                  60

Tyr Asn Ile Ser Ala Pro Asp Ile Leu His Leu Val Leu Arg Leu Arg
65                  70                  75                  80

Ala Ala

<210> SEQ ID NO 51
<211> LENGTH: 82
<212> TYPE: PRT
<213> ORGANISM: Artificial Sequence
<220> FEATURE:
<223> OTHER INFORMATION: Affilin 139826 Sequence

<400> SEQUENCE: 51

Met Gln Ile Phe Val Lys Thr Leu Thr Glu His Asp Ala Tyr Gly Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
50                  55                  60

Tyr Asn Ile Thr His Pro Asp Ile Leu His Leu Val Leu Arg Leu Cys
65                  70                  75                  80

Ala Ala

<210> SEQ ID NO 52
<211> LENGTH: 82
<212> TYPE: PRT
<213> ORGANISM: Artificial Sequence
<220> FEATURE:
<223> OTHER INFORMATION: Affilin 142298 Sequence

<400> SEQUENCE: 52

Met Gln Ile Phe Val Lys Thr Leu Thr Gly Gly Asp His Gly Tyr Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg

```
                35                  40                  45
Leu Ile Trp Ala Gly Lys Gln Leu Glu Asp Gly Arg Thr Leu Ser Asp
 50                  55                  60
Tyr Asn Ile Val Asn Pro Asp Ile Leu His Leu Val Leu Arg Leu Arg
 65                  70                  75                  80
Ala Ala

<210> SEQ ID NO 53
<211> LENGTH: 155
<212> TYPE: PRT
<213> ORGANISM: Artificial Sequence
<220> FEATURE:
<223> OTHER INFORMATION: Affilin 139895 Sequence

<400> SEQUENCE: 53

Met Gln Ile Phe Val Ala Thr Thr Thr Gly Lys Thr Ile Thr Leu Glu
 1               5                  10                  15
Val Glu Pro Ser Asp Thr Ile Glu Asn Val Lys Ala Lys Ile Gln Asp
                20                  25                  30
Lys Glu Gly Ile Pro Pro Asp Gln Gln Arg Leu Ile Trp Ala Gly Lys
                35                  40                  45
Gln Leu Glu Asp Gly Arg Thr Leu Ser Asp Tyr Asn Ile Gln Asn Pro
 50                  55                  60
Asp Ile Leu His Leu Val Leu Arg Leu Arg Ala Ala Gly Ile Gly Met
 65                  70                  75                  80
Gln Ile Phe Val Asp Thr His Thr Gly Lys Thr Ile Thr Leu Glu Val
                85                  90                  95
Glu Pro Ser Asp Thr Ile Glu Asn Val Lys Ala Lys Ile Gln Asp Lys
               100                 105                 110
Glu Gly Ile Pro Pro Asp Gln Gln Arg Leu Ile Trp Ala Gly Lys Gln
               115                 120                 125
Leu Glu Asp Gly Arg Thr Leu Ser Asp Tyr Asn Ile Arg Ala Gly Gln
               130                 135                 140
Thr Leu His Leu Val Leu Arg Leu Arg Ala Ala
145                 150                 155

<210> SEQ ID NO 54
<211> LENGTH: 155
<212> TYPE: PRT
<213> ORGANISM: Artificial Sequence
<220> FEATURE:
<223> OTHER INFORMATION: Affilin 139901 Sequence

<400> SEQUENCE: 54

Met Gln Ile Phe Val His Thr Asp Thr Gly Lys Thr Ile Thr Leu Glu
 1               5                  10                  15
Val Glu Pro Ser Asp Thr Ile Glu Asn Val Lys Ala Lys Ile Gln Asp
                20                  25                  30
Lys Glu Gly Ile Pro Pro Asp Gln Gln Arg Leu Ile Trp Ala Gly Lys
                35                  40                  45
Gln Leu Glu Asp Gly Arg Thr Leu Ser Asp Tyr Asn Ile Arg His Pro
 50                  55                  60
Asp Ile Leu His Leu Val Leu Arg Leu Arg Ala Ala Gly Ile Gly Met
 65                  70                  75                  80
Gln Ile Phe Val Asn Thr Phe Thr Gly Lys Thr Ile Thr Leu Glu Val
                85                  90                  95
Glu Pro Ser Asp Thr Ile Glu Asn Val Lys Ala Lys Ile Gln Asp Lys
```

100                 105                 110
Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Tyr Asn Gly Met
        130                 135                 140

Phe Leu His Leu Val Leu Arg Leu Arg Ala Ala
145                 150                 155

<210> SEQ ID NO 55
<211> LENGTH: 155
<212> TYPE: PRT
<213> ORGANISM: Artificial Sequence
<220> FEATURE:
<223> OTHER INFORMATION: Affilin 139851 Sequence

<400> SEQUENCE: 55

Met Gln Ile Phe Val His Thr Met Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln His Pro
    50                  55                  60

Asp Ile Leu His Leu Val Leu Arg Leu Arg Ala Ala Gly Ile Gly Met
65                  70                  75                  80

Gln Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Ser Arg Glu Pro
    130                 135                 140

Ala Leu His Leu Val Leu Arg Leu Arg Ala Ala
145                 150                 155

<210> SEQ ID NO 56
<211> LENGTH: 155
<212> TYPE: PRT
<213> ORGANISM: Artificial Sequence
<220> FEATURE:
<223> OTHER INFORMATION: Affilin 139959 Sequence

<400> SEQUENCE: 56

Met Gln Ile Phe Val His Thr Met Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg Asn Pro
    50                  55                  60

Asp Ile Leu His Leu Val Leu Arg Leu Arg Ala Ala Gly Ile Gly Met
65                  70                  75                  80

Gln Ile Phe Val Val Thr Phe Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Thr Gln Trp Thr
    130                 135                 140

Pro Leu His Leu Val Leu Arg Leu Arg Ala Ala
145                 150                 155

<210> SEQ ID NO 57
<211> LENGTH: 155
<212> TYPE: PRT
<213> ORGANISM: Artificial Sequence
<220> FEATURE:
<223> OTHER INFORMATION: Affilin 139853 Sequence

<400> SEQUENCE: 57

Met Gln Ile Phe Val His Thr Asn Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Ser Pro
50                  55                  60

Asp Ile Leu His Leu Val Leu Arg Leu Arg Ala Ala Gly Ile Gly Met
65                  70                  75                  80

Gln Ile Phe Val Asp Thr Ala Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Pro Glu Gly His
    130                 135                 140

Thr Leu His Leu Val Leu Arg Leu Arg Ala Ala
145                 150                 155

<210> SEQ ID NO 58
<211> LENGTH: 155
<212> TYPE: PRT
<213> ORGANISM: Artificial Sequence
<220> FEATURE:
<223> OTHER INFORMATION: Affilin 139864 Sequence

<400> SEQUENCE: 58

Met Gln Ile Phe Val His Thr Pro Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg Asn Pro
50                  55                  60

Asp Ile Leu His Leu Val Leu Arg Leu Arg Ala Ala Gly Ile Gly Met
65                  70                  75                  80

Gln Ile Phe Val His Thr Met Thr Gly Lys Thr Ile Thr Leu Glu Val
                85                  90                  95

```
Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Gly Ala Gly Thr
        130                 135                 140

Met Leu His Leu Val Leu Arg Leu Arg Ala Ala
145                 150                 155

<210> SEQ ID NO 59
<211> LENGTH: 155
<212> TYPE: PRT
<213> ORGANISM: Artificial Sequence
<220> FEATURE:
<223> OTHER INFORMATION: Affilin 140094 Sequence

<400> SEQUENCE: 59

Met Gln Ile Phe Val His Thr Gln Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Thr Ser Pro
    50                  55                  60

Asp Ile Leu His Leu Val Leu Arg Leu Arg Ala Ala Gly Ile Gly Met
65                  70                  75                  80

Gln Ile Phe Val Ile Thr Ser Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Pro Arg Ala Ala
        130                 135                 140

Ser Leu His Leu Val Leu Arg Leu Arg Ala Ala
145                 150                 155

<210> SEQ ID NO 60
<211> LENGTH: 155
<212> TYPE: PRT
<213> ORGANISM: Artificial Sequence
<220> FEATURE:
<223> OTHER INFORMATION: Affilin 140102 Sequence

<400> SEQUENCE: 60

Met Gln Ile Phe Val His Thr Ser Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg His Pro
    50                  55                  60

Asp Ile Leu His Leu Val Leu Arg Leu Arg Ala Ala Gly Ile Gly Met
65                  70                  75                  80

Gln Ile Phe Val Thr Thr Thr Thr Gly Lys Thr Ile Thr Leu Glu Val
```

```
                    85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gln Pro Ser Lys
    130                 135                 140

Leu Leu His Leu Val Leu Arg Leu Arg Ala Ala
145                 150                 155

<210> SEQ ID NO 61
<211> LENGTH: 155
<212> TYPE: PRT
<213> ORGANISM: Artificial Sequence
<220> FEATURE:
<223> OTHER INFORMATION: Affilin 139961 Sequence

<400> SEQUENCE: 61

Met Gln Ile Phe Val His Thr Thr Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg His Pro
    50                  55                  60

Asp Ile Leu His Leu Val Leu Arg Leu Arg Ala Ala Gly Ile Gly Met
65                  70                  75                  80

Gln Ile Phe Val Ser Thr Phe Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Val Ala His Asn
    130                 135                 140

Met Leu His Leu Val Leu Arg Leu Arg Ala Ala
145                 150                 155

<210> SEQ ID NO 62
<211> LENGTH: 155
<212> TYPE: PRT
<213> ORGANISM: Artificial Sequence
<220> FEATURE:
<223> OTHER INFORMATION: Affilin 139848 Sequence

<400> SEQUENCE: 62

Met Gln Ile Phe Val His Thr Val Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg Asn Pro
    50                  55                  60

Asp Ile Leu His Leu Val Leu Arg Leu Arg Ala Ala Gly Ile Gly Met
65                  70                  75                  80
```

```
Gln Ile Phe Val Lys Thr Pro Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Pro Ala Arg Arg
    130                 135                 140

Ser Leu His Leu Val Leu Arg Leu Arg Ala Ala
145                 150                 155

<210> SEQ ID NO 63
<211> LENGTH: 155
<212> TYPE: PRT
<213> ORGANISM: Artificial Sequence
<220> FEATURE:
<223> OTHER INFORMATION: Affilin 139935 Sequence

<400> SEQUENCE: 63

Met Gln Ile Phe Val His Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln His Pro
    50                  55                  60

Asp Ile Leu His Leu Val Leu Arg Leu Arg Ala Ala Gly Ile Gly Met
65                  70                  75                  80

Gln Ile Phe Val Asp Thr Pro Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Pro Glu His Asn
    130                 135                 140

Ala Leu His Leu Val Leu Arg Leu Arg Ala Ala
145                 150                 155

<210> SEQ ID NO 64
<211> LENGTH: 155
<212> TYPE: PRT
<213> ORGANISM: Artificial Sequence
<220> FEATURE:
<223> OTHER INFORMATION: Affilin 139880 Sequence

<400> SEQUENCE: 64

Met Gln Ile Phe Val His Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg His Pro
    50                  55                  60

Asp Ile Leu His Leu Val Leu Arg Leu Arg Ala Ala Gly Ile Gly Met
65                  70                  75                  80
```

```
Gln Ile Phe Val Arg Thr Pro Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile His Arg Ser Ala
        130                 135                 140

Met Leu His Leu Val Leu Arg Leu Arg Ala Ala
145                 150                 155

<210> SEQ ID NO 65
<211> LENGTH: 155
<212> TYPE: PRT
<213> ORGANISM: Artificial Sequence
<220> FEATURE:
<223> OTHER INFORMATION: Affilin 139907 Sequence

<400> SEQUENCE: 65

Met Gln Ile Phe Val His Thr Trp Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Ser His Pro
        50                  55                  60

Asp Ile Leu His Leu Val Leu Arg Leu Arg Ala Ala Gly Ile Gly Met
65                  70                  75                  80

Gln Ile Phe Val Val Thr Thr Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Ala Asn Arg Ala
        130                 135                 140

Arg Leu His Leu Val Leu Arg Leu Arg Ala Ala
145                 150                 155

<210> SEQ ID NO 66
<211> LENGTH: 155
<212> TYPE: PRT
<213> ORGANISM: Artificial Sequence
<220> FEATURE:
<223> OTHER INFORMATION: Affilin 140077 Sequence

<400> SEQUENCE: 66

Met Gln Ile Phe Val His Thr Tyr Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Arg His Pro
        50                  55                  60

Asp Ile Leu His Leu Val Leu Arg Leu Arg Ala Ala Gly Ile Gly Met
```

```
                65                  70                  75                  80
Gln Ile Phe Val His Thr Asn Thr Gly Lys Thr Ile Thr Leu Glu Val
                    85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Gly Ala Arg Thr
        130                 135                 140

Ser Leu His Leu Val Leu Arg Leu Arg Ala Ala
145                 150                 155

<210> SEQ ID NO 67
<211> LENGTH: 155
<212> TYPE: PRT
<213> ORGANISM: Artificial Sequence
<220> FEATURE:
<223> OTHER INFORMATION: Affilin 140123 Sequence

<400> SEQUENCE: 67

Met Gln Ile Phe Val Tyr Thr Asn Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Gln Ser Pro
        50                  55                  60

Asp Ile Leu His Leu Val Leu Arg Leu Arg Ala Ala Gly Ile Gly Met
65                  70                  75                  80

Gln Ile Phe Val Leu Thr Asp Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Thr Met Pro Pro
        130                 135                 140

Pro Leu His Leu Val Leu Arg Leu Arg Ala Ala
145                 150                 155

<210> SEQ ID NO 68
<211> LENGTH: 155
<212> TYPE: PRT
<213> ORGANISM: Artificial Sequence
<220> FEATURE:
<223> OTHER INFORMATION: Affilin 139882 Sequence

<400> SEQUENCE: 68

Met Gln Ile Phe Val Tyr Thr Asn Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Arg Asn Pro
        50                  55                  60
```

```
Asp Ile Leu His Leu Val Leu Arg Leu Arg Ala Ala Gly Ile Gly Met
 65                  70                  75                  80

Gln Ile Phe Val Asp Thr Tyr Thr Gly Lys Thr Ile Thr Leu Glu Val
                 85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Tyr Glu Pro
    130                 135                 140

Ala Leu His Leu Val Leu Arg Leu Arg Ala Ala
145                 150                 155

<210> SEQ ID NO 69
<211> LENGTH: 155
<212> TYPE: PRT
<213> ORGANISM: Artificial Sequence
<220> FEATURE:
<223> OTHER INFORMATION: Affilin 138838 Sequence

<400> SEQUENCE: 69

Met Gln Ile Phe Val Tyr Thr Asn Thr Gly Lys Thr Ile Thr Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Arg Leu Ile Trp Ala Gly Lys
         35                  40                  45

Gln Leu Glu Asp Gly Arg Thr Leu Ser Asp Tyr Asn Ile Arg Asn Pro
     50                  55                  60

Asp Ile Leu His Leu Val Leu Arg Leu Arg Ala Ala Gly Ile Gly Met
 65                  70                  75                  80

Gln Ile Phe Val His Thr Ile Thr Gly Lys Thr Ile Thr Leu Glu Val
                 85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Glu Gly Glu Arg
    130                 135                 140

Asp Leu His Leu Val Leu Arg Leu Arg Ala Ala
145                 150                 155

<210> SEQ ID NO 70
<211> LENGTH: 155
<212> TYPE: PRT
<213> ORGANISM: Artificial Sequence
<220> FEATURE:
<223> OTHER INFORMATION: Affilin 139923 Sequence

<400> SEQUENCE: 70

Met Gln Ile Ser Leu Tyr Thr Pro Thr Gly Lys Thr Leu Thr Leu Glu
  1               5                  10                  15

Leu Glu Pro Ser Asp Thr Ile Glu Asn Val Lys Ala Lys Ile Gln Asp
             20                  25                  30

Lys Glu Gly Ile Pro Pro Asp Gln Gln Arg Leu Ile Trp Ala Gly Lys
         35                  40                  45

Gln Leu Glu Asp Gly Arg Thr Leu Ser Asp Tyr Asn Ile Arg His Pro
     50                  55                  60
```

Asp Ile Leu His Leu Val Leu Arg Leu Arg Ala Ala Gly Ile Gly Met
65                  70                  75                  80

Gln Ile Phe Val Asp Thr Tyr Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Tyr Glu Pro
    130                 135                 140

Ala Leu His Leu Leu Arg Leu Arg Ala Ala
145                 150                 155

<210> SEQ ID NO 71
<211> LENGTH: 155
<212> TYPE: PRT
<213> ORGANISM: Artificial Sequence
<220> FEATURE:
<223> OTHER INFORMATION: Affilin 138819 Sequence

<400> SEQUENCE: 71

Met Gln Ile Phe Val Tyr Thr Thr Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Asn Pro
    50                  55                  60

Asp Ile Leu His Leu Val Leu Arg Leu Arg Ala Ala Gly Ile Gly Met
65                  70                  75                  80

Gln Ile Phe Val Tyr Thr Ile Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Ala Gln His Ser
    130                 135                 140

Glu Leu His Leu Val Leu Arg Leu Arg Ala Ala
145                 150                 155

<210> SEQ ID NO 72
<211> LENGTH: 155
<212> TYPE: PRT
<213> ORGANISM: Artificial Sequence
<220> FEATURE:
<223> OTHER INFORMATION: Affilin 140005 Sequence

<400> SEQUENCE: 72

Met Gln Ile Phe Val Tyr Thr Val Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg Asn Pro

Asp Ile Leu His Leu Val Leu Arg Leu Arg Ala Ala Gly Ile Gly Met
65                  70                  75                  80

Gln Ile Phe Val Glu Thr Asp Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gln Lys Asn Ala
    130                 135                 140

Gln Leu His Leu Val Leu Arg Leu Arg Ala Ala
145                 150                 155

<210> SEQ ID NO 73
<211> LENGTH: 155
<212> TYPE: PRT
<213> ORGANISM: Artificial Sequence
<220> FEATURE:
<223> OTHER INFORMATION: Affilin 138845 Sequence

<400> SEQUENCE: 73

Met Gln Ile Phe Val Tyr Thr Asn Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg Asn Pro
    50                  55                  60

Asp Ile Leu His Leu Val Leu Arg Leu Arg Ala Ala Gly Ile Gly Met
65                  70                  75                  80

Gln Ile Phe Val His Thr Ile Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Gly Glu Arg
    130                 135                 140

Asp Leu His Leu Val Leu Arg Leu Arg Ala Ala
145                 150                 155

<210> SEQ ID NO 74
<211> LENGTH: 82
<212> TYPE: PRT
<213> ORGANISM: Artificial Sequence
<220> FEATURE:
<223> OTHER INFORMATION: Affilin 141748 Sequence

<400> SEQUENCE: 74

Met Gln Ile Phe Val Lys Thr Leu Thr Arg Ser Trp Tyr Tyr Trp Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

```
Leu Ile Trp Ala Gly Lys Gln Leu Glu Asp Gly Arg Thr Leu Ser Asp
 50                  55                  60

Tyr Asn Ile Lys Glu His Arg Trp Leu His Leu Val Leu Arg Leu Arg
 65                  70                  75                  80

Ala Ala

<210> SEQ ID NO 75
<211> LENGTH: 152
<212> TYPE: PRT
<213> ORGANISM: Artificial Sequence
<220> FEATURE:
<223> OTHER INFORMATION: Affilin 142265 Sequence

<400> SEQUENCE: 75

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Glu Leu Thr Phe Ala Gly Lys
             35                  40                  45

Gln Leu Glu Asp Gly Arg Thr Leu Ser Asp Tyr Asn Ile Gln Lys Glu
 50                  55                  60

Ser Thr Leu Trp Leu Glu Leu Tyr Ala Lys Ala Met Gln Ile Phe
 65                  70                  75                  80

Val Gln Thr Ile Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Thr Arg Leu Val Trp Leu His
        130                 135                 140

Leu Val Leu Arg Leu Arg Ala Ala
145                 150

<210> SEQ ID NO 76
<211> LENGTH: 155
<212> TYPE: PRT
<213> ORGANISM: Artificial Sequence
<220> FEATURE:
<223> OTHER INFORMATION: Affilin 139989 Sequence

<400> SEQUENCE: 76

Met Gln Ile Phe Val Val Thr Met Thr Gly Lys Thr Ile Thr Leu Glu
 1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Arg Leu Ile Trp Ala Gly Lys
             35                  40                  45

Gln Leu Glu Asp Gly Arg Thr Leu Ser Asp Tyr Asn Ile Glu Trp Tyr
 50                  55                  60

Thr Asn Leu His Leu Val Leu Arg Leu Arg Ala Ala Gly Ile Gly Met
 65                  70                  75                  80

Gln Ile Phe Val Trp Thr Thr Gly Lys Thr Ile Thr Leu Glu Val
                 85                  90                  95

Glu Pro Ser Asp Thr Ile Glu Asn Val Lys Ala Lys Ile Gln Asp Lys
            100                 105                 110
```

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Leu His Gly Gln
    130                 135                 140

Trp Leu His Leu Val Leu Arg Leu Arg Ala Ala
145                 150                 155

<210> SEQ ID NO 77
<211> LENGTH: 155
<212> TYPE: PRT
<213> ORGANISM: Artificial Sequence
<220> FEATURE:
<223> OTHER INFORMATION: Affilin 138840 Sequence

<400> SEQUENCE: 77

Met Val Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Phe Lys
    50                  55                  60

Leu Ser Leu His Leu Val Leu Arg Leu Arg Ala Ala Gly Ile Gly Met
65                  70                  75                  80

Gln Ile Phe Val His Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gly Trp Gln Ala
    130                 135                 140

Pro Leu His Leu Val Leu Arg Leu Arg Ala Ala
145                 150                 155

<210> SEQ ID NO 78
<211> LENGTH: 15
<212> TYPE: PRT
<213> ORGANISM: Artificial Sequence
<220> FEATURE:
<223> OTHER INFORMATION: Artificial Linker

<400> SEQUENCE: 78

Gly Gly Gly Gly Ser Gly Gly Gly Ser Gly Gly Gly Gly Ser
1               5                   10                  15

<210> SEQ ID NO 79
<211> LENGTH: 10
<212> TYPE: PRT
<213> ORGANISM: Artificial Sequence
<220> FEATURE:
<223> OTHER INFORMATION: Artificial Linker

<400> SEQUENCE: 79

Ser Gly Gly Gly Gly Ser Gly Gly Gly Gly
1               5                   10

<210> SEQ ID NO 80
<211> LENGTH: 12
<212> TYPE: PRT

```
<213> ORGANISM: Artificial Sequence
<220> FEATURE:
<223> OTHER INFORMATION: Artificial Linker

<400> SEQUENCE: 80

Gly Gly Gly Ser Gly Gly Gly Ser Gly Gly Gly Ser
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Artificial Linker

<400> SEQUENCE: 81

Ser Gly Gly Gly Gly Ile Gly
1               5

<210> SEQ ID NO 82
<211> LENGTH: 8
<212> TYPE: PRT
<213> ORGANISM: Artificial Sequence
<220> FEATURE:
<223> OTHER INFORMATION: Artificial Linker

<400> SEQUENCE: 82

Gly Ile Gly Ser Gly Gly Gly Gly
1               5

<210> SEQ ID NO 83
<211> LENGTH: 6
<212> TYPE: PRT
<213> ORGANISM: Artificial Sequence
<220> FEATURE:
<223> OTHER INFORMATION: Artificial Linker

<400> SEQUENCE: 83

Gly Gly Gly Gly Ile Gly
1               5

<210> SEQ ID NO 84
<211> LENGTH: 12
<212> TYPE: PRT
<213> ORGANISM: Artificial Sequence
<220> FEATURE:
<223> OTHER INFORMATION: Artificial Linker

<400> SEQUENCE: 84

Ser Gly Gly Gly Gly Ser Gly Gly Gly Gly Ile Gly
1               5                   10

<210> SEQ ID NO 85
<211> LENGTH: 4
<212> TYPE: PRT
<213> ORGANISM: Artificial Sequence
<220> FEATURE:
<223> OTHER INFORMATION: Artificial Linker

<400> SEQUENCE: 85

Gly Ile Gly Gly
1

<210> SEQ ID NO 86
<211> LENGTH: 331
<212> TYPE: PRT
<213> ORGANISM: Artificial Sequence
```

<220> FEATURE:
<223> OTHER INFORMATION: Fusion protein NL 139819 Sequence

<400> SEQUENCE: 86

```
Met Val Ser Thr Pro Gln Phe Leu Val Phe Leu Leu Phe Trp Ile Pro
1               5                   10                  15

Ala Ser Arg Ser Met Gln Ile Phe Val Lys Thr Leu Thr Tyr Asn Pro
            20                  25                  30

Met Arg Tyr Gly Lys Thr Ile Thr Leu Glu Val Glu Pro Ser Asp Thr
        35                  40                  45

Ile Glu Asn Val Lys Ala Lys Ile Gln Asp Lys Glu Gly Ile Pro Pro
50                  55                  60

Asp Gln Gln Arg Leu Ile Trp Ala Gly Lys Gln Leu Glu Asp Gly Arg
65                  70                  75                  80

Thr Leu Ser Asp Tyr Asn Ile Arg Asn Pro Asp Ile Leu His Leu Val
                85                  90                  95

Leu Arg Leu Arg Ala Ala Gly Gly Gly Ser Gly Gly Gly Gly Ser
            100                 105                 110

Gly Gly Gly Gly Ser Asp Ile Leu Leu Thr Gln Ser Pro Val Ile Leu
            115                 120                 125

Ser Val Ser Pro Gly Glu Arg Val Ser Phe Ser Cys Arg Ala Ser Gln
130                 135                 140

Ser Ile Gly Thr Asn Ile His Trp Tyr Gln Gln Arg Thr Asn Gly Ser
145                 150                 155                 160

Pro Arg Leu Leu Ile Lys Tyr Ala Ser Glu Ser Ile Ser Gly Ile Pro
                165                 170                 175

Ser Arg Phe Ser Gly Ser Gly Ser Gly Thr Asp Phe Thr Leu Ser Ile
            180                 185                 190

Asn Ser Val Glu Ser Glu Asp Ile Ala Asp Tyr Tyr Cys Gln Gln Asn
            195                 200                 205

Asn Asn Trp Pro Thr Thr Phe Gly Ala Gly Thr Lys Leu Glu Leu Lys
210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
            275                 280                 285

Thr Tyr Ser Leu Ser Ser Thr Leu Thr Leu Ser Lys Ala Asp Tyr Glu
290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330
```

<210> SEQ ID NO 87
<211> LENGTH: 331
<212> TYPE: PRT
<213> ORGANISM: Artificial Sequence
<220> FEATURE:
<223> OTHER INFORMATION: Fusion protein CL 139819 Sequence

<400> SEQUENCE: 87

Met Val Ser Thr Pro Gln Phe Leu Val Phe Leu Leu Phe Trp Ile Pro

```
            1               5                  10                 15
        Ala Ser Arg Ser Asp Ile Leu Leu Thr Gln Ser Pro Val Ile Leu Ser
                     20                  25                 30

Val Ser Pro Gly Glu Arg Val Ser Phe Ser Cys Arg Ala Ser Gln Ser
                     35                  40                 45

Ile Gly Thr Asn Ile His Trp Tyr Gln Gln Arg Thr Asn Gly Ser Pro
                     50                  55                 60

Arg Leu Leu Ile Lys Tyr Ala Ser Glu Ser Ile Ser Gly Ile Pro Ser
        65                   70                  75                 80

Arg Phe Ser Gly Ser Gly Ser Gly Thr Asp Phe Thr Leu Ser Ile Asn
                     85                  90                 95

Ser Val Glu Ser Glu Asp Ile Ala Asp Tyr Tyr Cys Gln Gln Asn Asn
                     100                 105                110

Asn Trp Pro Thr Thr Phe Gly Ala Gly Thr Lys Leu Glu Leu Lys Arg
                     115                 120                125

Thr Val Ala Ala Pro Ser Val Phe Ile Phe Pro Pro Ser Asp Glu Gln
                     130                 135                140

Leu Lys Ser Gly Thr Ala Ser Val Val Cys Leu Leu Asn Asn Phe Tyr
        145                  150                 155                160

Pro Arg Glu Ala Lys Val Gln Trp Lys Val Asp Asn Ala Leu Gln Ser
                     165                 170                175

Gly Asn Ser Gln Glu Ser Val Thr Glu Gln Asp Ser Lys Asp Ser Thr
                     180                 185                190

Tyr Ser Leu Ser Ser Thr Leu Thr Leu Ser Lys Ala Asp Tyr Glu Lys
                     195                 200                205

His Lys Val Tyr Ala Cys Glu Val Thr His Gln Gly Leu Ser Ser Pro
        210                  215                 220

Val Thr Lys Ser Phe Asn Arg Gly Glu Cys Gly Gly Gly Gly Ser Gly
        225                  230                 235                240

Gly Gly Gly Ser Gly Gly Gly Ser Met Gln Ile Phe Val Lys Thr
                     245                 250                255

Leu Thr Tyr Asn Pro Met Arg Tyr Gly Lys Thr Ile Thr Leu Glu Val
                     260                 265                270

Glu Pro Ser Asp Thr Ile Glu Asn Val Lys Ala Lys Ile Gln Asp Lys
                     275                 280                285

Glu Gly Ile Pro Pro Asp Gln Gln Arg Leu Ile Trp Ala Gly Lys Gln
                     290                 295                300

Leu Glu Asp Gly Arg Thr Leu Ser Asp Tyr Asn Ile Arg Asn Pro Asp
        305                  310                 315                320

Ile Leu His Leu Val Leu Arg Leu Arg Ala Ala
                     325                 330

<210> SEQ ID NO 88
<211> LENGTH: 325
<212> TYPE: PRT
<213> ORGANISM: Artificial Sequence
<220> FEATURE:
<223> OTHER INFORMATION: Fusion protein CL ubiquitin Sequence

<400> SEQUENCE: 88

Met Val Ser Thr Pro Gln Phe Leu Val Phe Leu Leu Phe Trp Ile Pro
1               5                  10                 15

Ala Ser Arg Ser Asp Ile Leu Leu Thr Gln Ser Pro Val Ile Leu Ser
             20                  25                 30

Val Ser Pro Gly Glu Arg Val Ser Phe Ser Cys Arg Ala Ser Gln Ser
```

-continued

```
                35                  40                  45
Ile Gly Thr Asn Ile His Trp Tyr Gln Gln Arg Thr Asn Gly Ser Pro
 50                  55                  60

Arg Leu Leu Ile Lys Tyr Ala Ser Glu Ser Ile Ser Gly Ile Pro Ser
 65                  70                  75                  80

Arg Phe Ser Gly Ser Gly Ser Gly Thr Asp Phe Thr Leu Ser Ile Asn
                 85                  90                  95

Ser Val Glu Ser Glu Asp Ile Ala Asp Tyr Tyr Cys Gln Gln Asn Asn
                100                 105                 110

Asn Trp Pro Thr Thr Phe Gly Ala Gly Thr Lys Leu Glu Leu Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys Gly Gly Gly Ser Gly Gly
225                 230                 235                 240

Gly Gly Ser Gly Gly Gly Ser Met Gln Ile Phe Val Lys Thr
                245                 250                 255

Leu Thr Gly Lys Thr Ile Thr Leu Glu Val Glu Pro Ser Asp Thr Ile
            260                 265                 270

Glu Asn Val Lys Ala Lys Ile Gln Asp Lys Glu Gly Ile Pro Pro Asp
        275                 280                 285

Gln Gln Arg Leu Ile Trp Ala Gly Lys Gln Leu Glu Asp Gly Arg Thr
    290                 295                 300

Leu Ser Asp Tyr Asn Ile Gln Lys Glu Ser Thr Leu His Leu Val Leu
305                 310                 315                 320

Arg Leu Arg Ala Ala
            325

<210> SEQ ID NO 89
<211> LENGTH: 325
<212> TYPE: PRT
<213> ORGANISM: Artificial Sequence
<220> FEATURE:
<223> OTHER INFORMATION: Fusion protein NL ubiquitin Sequence

<400> SEQUENCE: 89

Met Val Ser Thr Pro Gln Phe Leu Val Phe Leu Leu Phe Trp Ile Pro
 1               5                  10                  15

Ala Ser Arg Ser Met Gln Ile Phe Val Lys Thr Leu Thr Gly Lys Thr
                20                  25                  30

Ile Thr Leu Glu Val Glu Pro Ser Asp Thr Ile Glu Asn Val Lys Ala
            35                  40                  45

Lys Ile Gln Asp Lys Glu Gly Ile Pro Pro Asp Gln Gln Arg Leu Ile
        50                  55                  60

Trp Ala Gly Lys Gln Leu Glu Asp Gly Arg Thr Leu Ser Asp Tyr Asn
```

```
                65                  70                  75                  80
Ile Gln Lys Glu Ser Thr Leu His Leu Val Leu Arg Leu Arg Ala Ala
                    85                  90                  95

Gly Gly Gly Gly Ser Gly Gly Gly Ser Gly Gly Gly Ser Asp
            100                 105                 110

Ile Leu Leu Thr Gln Ser Pro Val Ile Leu Ser Val Ser Pro Gly Glu
            115                 120                 125

Arg Val Ser Phe Ser Cys Arg Ala Ser Gln Ser Ile Gly Thr Asn Ile
            130                 135                 140

His Trp Tyr Gln Gln Arg Thr Asn Gly Ser Pro Arg Leu Leu Ile Lys
145                 150                 155                 160

Tyr Ala Ser Glu Ser Ile Ser Gly Ile Pro Ser Arg Phe Ser Gly Ser
                165                 170                 175

Gly Ser Gly Thr Asp Phe Thr Leu Ser Ile Asn Ser Val Glu Ser Glu
            180                 185                 190

Asp Ile Ala Asp Tyr Tyr Cys Gln Gln Asn Asn Asn Trp Pro Thr Thr
            195                 200                 205

Phe Gly Ala Gly Thr Lys Leu Glu Leu Lys Arg Thr Val Ala Ala Pro
            210                 215                 220

Ser Val Phe Ile Phe Pro Pro Ser Asp Glu Gln Leu Lys Ser Gly Thr
225                 230                 235                 240

Ala Ser Val Val Cys Leu Leu Asn Asn Phe Tyr Pro Arg Glu Ala Lys
                245                 250                 255

Val Gln Trp Lys Val Asp Asn Ala Leu Gln Ser Gly Asn Ser Gln Glu
            260                 265                 270

Ser Val Thr Glu Gln Asp Ser Lys Asp Ser Thr Tyr Ser Leu Ser Ser
            275                 280                 285

Thr Leu Thr Leu Ser Lys Ala Asp Tyr Glu Lys His Lys Val Tyr Ala
            290                 295                 300

Cys Glu Val Thr His Gln Gly Leu Ser Ser Pro Val Thr Lys Ser Phe
305                 310                 315                 320

Asn Arg Gly Glu Cys
            325

<210> SEQ ID NO 90
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 90

Arg Asn Pro Asp Ile
1               5

<210> SEQ ID NO 91
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 91

Gln Asn Pro Asp Ile
1               5

<210> SEQ ID NO 92
<211> LENGTH: 5
```

```
<212> TYPE: PRT
<213> ORGANISM: Artificial Sequence
<220> FEATURE:
<223> OTHER INFORMATION: Artificial Binding Cassette

<400> SEQUENCE: 92

Arg His Pro Asp Ile
1               5

<210> SEQ ID NO 93
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 93

Gln His Pro Asp Ile
1               5

<210> SEQ ID NO 94
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 94

Gly Glu Pro Asp Ile
1               5

<210> SEQ ID NO 95
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 95

Gly His Pro Asp Ile
1               5

<210> SEQ ID NO 96
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 96

Ile His Ala Asp Ile
1               5

<210> SEQ ID NO 97
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 97

His His Pro Asp Ile
1               5

<210> SEQ ID NO 98
<211> LENGTH: 5
<212> TYPE: PRT
```

```
<213> ORGANISM: Artificial Sequence
<220> FEATURE:
<223> OTHER INFORMATION: Artificial Binding Cassette

<400> SEQUENCE: 98

Gln Ala Pro Asp Ile
1               5

<210> SEQ ID NO 99
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 99

Gln Gln Pro Asp Ile
1               5

<210> SEQ ID NO 100
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 100

Arg Arg Val Asp Val
1               5

<210> SEQ ID NO 101
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 101

Ser Ala Pro Asp Ile
1               5

<210> SEQ ID NO 102
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 102

Thr His Pro Asp Ile
1               5

<210> SEQ ID NO 103
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 103

Val Asn Pro Asp Ile
1               5

<210> SEQ ID NO 104
<211> LENGTH: 5
<212> TYPE: PRT
<213> ORGANISM: Artificial Sequence
```

```
<220> FEATURE:
<223> OTHER INFORMATION: Artificial Binding Cassette

<400> SEQUENCE: 104

Gln Ser Pro Asp Ile
1               5

<210> SEQ ID NO 105
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 105

Thr Ser Pro Asp Ile
1               5

<210> SEQ ID NO 106
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 106

Ser His Pro Asp Ile
1               5

<210> SEQ ID NO 107
<211> LENGTH: 559
<212> TYPE: PRT
<213> ORGANISM: Artificial Sequence
<220> FEATURE:
<223> OTHER INFORMATION: Fusion protein CH ubiquitin Sequence

<400> SEQUENCE: 107

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190
```

```
Ala Val Leu Gln Ser Ser Gly Leu Tyr Ser Leu Ser Val Val Thr
            195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys Gly Gly Gly Ser Gly Gly Gly Ser Gly Gly Ser Gly
465                 470                 475                 480

Gly Gly Ser Met Gln Ile Phe Val Lys Thr Leu Thr Gly Lys Thr Ile
                485                 490                 495

Thr Leu Glu Val Glu Pro Ser Asp Thr Ile Glu Asn Val Lys Ala Lys
            500                 505                 510

Ile Gln Asp Lys Glu Gly Ile Pro Pro Asp Gln Gln Arg Leu Ile Trp
        515                 520                 525

Ala Gly Lys Gln Leu Glu Asp Gly Arg Thr Leu Ser Asp Tyr Asn Ile
    530                 535                 540

Gln Lys Glu Ser Thr Leu His Leu Val Leu Arg Leu Arg Ala Ala
545                 550                 555

<210> SEQ ID NO 108
<211> LENGTH: 565
<212> TYPE: PRT
<213> ORGANISM: Artificial Sequence
<220> FEATURE:
<223> OTHER INFORMATION: Fusion protein CH 139819 Sequence

<400> SEQUENCE: 108
```

```
Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
            35                  40                  45

Thr Asn Tyr Gly Val His Trp Val Arg Gln Ser Pro Gly Lys Gly Leu
        50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
                100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415
```

Pro Val Leu Asp Ser Asp Gly Ser Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys Gly Gly Gly Ser Gly Gly Gly Ser Gly Gly Gly Gly
465                 470                 475                 480

Gly Gly Ser Met Gln Ile Phe Val Lys Thr Leu Thr Tyr Asn Pro Met
            485                 490                 495

Arg Tyr Gly Lys Thr Ile Thr Leu Glu Val Glu Pro Ser Asp Thr Ile
            500                 505                 510

Glu Asn Val Lys Ala Lys Ile Gln Asp Lys Glu Gly Ile Pro Pro Asp
            515                 520                 525

Gln Gln Arg Leu Ile Trp Ala Gly Lys Gln Leu Glu Asp Gly Arg Thr
            530                 535                 540

Leu Ser Asp Tyr Asn Ile Arg Asn Pro Asp Ile Leu His Leu Val Leu
545                 550                 555                 560

Arg Leu Arg Ala Ala
            565

<210> SEQ ID NO 109
<211> LENGTH: 559
<212> TYPE: PRT
<213> ORGANISM: Artificial Sequence
<220> FEATURE:
<223> OTHER INFORMATION: Fusion protein NH ubiquitin Sequence

<400> SEQUENCE: 109

Met Ala Val Leu Gly Leu Leu Phe Cys Leu Val Thr Phe Pro Ser Cys
1               5                   10                  15

Val Leu Ser Met Gln Ile Phe Val Lys Thr Leu Thr Gly Lys Thr Ile
            20                  25                  30

Thr Leu Glu Val Glu Pro Ser Asp Thr Ile Glu Asn Val Lys Ala Lys
            35                  40                  45

Ile Gln Asp Lys Glu Gly Ile Pro Pro Asp Gln Gln Arg Leu Ile Trp
        50                  55                  60

Ala Gly Lys Gln Leu Glu Asp Gly Arg Thr Leu Ser Asp Tyr Asn Ile
65                  70                  75                  80

Gln Lys Glu Ser Thr Leu His Leu Val Leu Arg Leu Arg Ala Ala Gly
                85                  90                  95

Gly Gly Gly Ser Gly Gly Gly Ser Gly Gly Gly Ser Gly Gln Val
            100                 105                 110

Gln Leu Lys Gln Ser Gly Pro Gly Leu Val Gln Pro Ser Gln Ser Leu
            115                 120                 125

Ser Ile Thr Cys Thr Val Ser Gly Phe Ser Leu Thr Asn Tyr Gly Val
130                 135                 140

His Trp Val Arg Gln Ser Pro Gly Lys Gly Leu Glu Trp Leu Gly Val
145                 150                 155                 160

Ile Trp Ser Gly Gly Asn Thr Asp Tyr Asn Thr Pro Phe Thr Ser Arg
            165                 170                 175

Leu Ser Ile Asn Lys Asp Asn Ser Lys Ser Gln Val Phe Phe Lys Met
            180                 185                 190

Asn Ser Leu Gln Ser Asn Asp Thr Ala Ile Tyr Tyr Cys Ala Arg Ala
            195                 200                 205

Leu Thr Tyr Tyr Asp Tyr Glu Phe Ala Tyr Trp Gly Gln Gly Thr Leu
210             215                 220

Val Thr Val Ser Ala Ala Ser Thr Lys Gly Pro Ser Val Phe Pro Leu
225             230                 235                 240

Ala Pro Ser Ser Lys Ser Thr Ser Gly Gly Thr Ala Ala Leu Gly Cys
                245                 250                 255

Leu Val Lys Asp Tyr Phe Pro Glu Pro Val Thr Val Ser Trp Asn Ser
                260                 265                 270

Gly Ala Leu Thr Ser Gly Val His Thr Phe Pro Ala Val Leu Gln Ser
            275                 280                 285

Ser Gly Leu Tyr Ser Leu Ser Ser Val Val Thr Val Pro Ser Ser Ser
        290                 295                 300

Leu Gly Thr Gln Thr Tyr Ile Cys Asn Val Asn His Lys Pro Ser Asn
305                 310                 315                 320

Thr Lys Val Asp Lys Arg Val Glu Pro Lys Ser Cys Asp Lys Thr His
                325                 330                 335

Thr Cys Pro Pro Cys Pro Ala Pro Glu Leu Leu Gly Gly Pro Ser Val
                340                 345                 350

Phe Leu Phe Pro Pro Lys Pro Lys Asp Thr Leu Met Ile Ser Arg Thr
            355                 360                 365

Pro Glu Val Thr Cys Val Val Val Asp Val Ser His Glu Asp Pro Glu
370                 375                 380

Val Lys Phe Asn Trp Tyr Val Asp Gly Val Glu Val His Asn Ala Lys
385                 390                 395                 400

Thr Lys Pro Arg Glu Glu Gln Tyr Asn Ser Thr Tyr Arg Val Val Ser
                405                 410                 415

Val Leu Thr Val Leu His Gln Asp Trp Leu Asn Gly Lys Glu Tyr Lys
                420                 425                 430

Cys Lys Val Ser Asn Lys Ala Leu Pro Ala Pro Ile Glu Lys Thr Ile
            435                 440                 445

Ser Lys Ala Lys Gly Gln Pro Arg Glu Pro Gln Val Tyr Thr Leu Pro
        450                 455                 460

Pro Ser Arg Glu Glu Met Thr Lys Asn Gln Val Ser Leu Thr Cys Leu
465                 470                 475                 480

Val Lys Gly Phe Tyr Pro Ser Asp Ile Ala Val Glu Trp Glu Ser Asn
                485                 490                 495

Gly Gln Pro Glu Asn Asn Tyr Lys Thr Thr Pro Pro Val Leu Asp Ser
                500                 505                 510

Asp Gly Ser Phe Phe Leu Tyr Ser Lys Leu Thr Val Asp Lys Ser Arg
            515                 520                 525

Trp Gln Gln Gly Asn Val Phe Ser Cys Ser Val Met His Glu Ala Leu
530                 535                 540

His Asn His Tyr Thr Gln Lys Ser Leu Ser Leu Ser Pro Gly Lys
545                 550                 555

<210> SEQ ID NO 110
<211> LENGTH: 565
<212> TYPE: PRT
<213> ORGANISM: Artificial Sequence
<220> FEATURE:
<223> OTHER INFORMATION: Fusion protein NH 139819 Sequence

<400> SEQUENCE: 110

Met Ala Val Leu Gly Leu Leu Phe Cys Leu Val Thr Phe Pro Ser Cys
1               5                   10                  15

```
Val Leu Ser Met Gln Ile Phe Val Lys Thr Leu Thr Tyr Asn Pro Met
            20                  25                  30

Arg Tyr Gly Lys Thr Ile Thr Leu Glu Val Glu Pro Ser Asp Thr Ile
                35                  40                  45

Glu Asn Val Lys Ala Lys Ile Gln Asp Lys Glu Gly Ile Pro Pro Asp
        50                  55                  60

Gln Gln Arg Leu Ile Trp Ala Gly Lys Gln Leu Glu Asp Gly Arg Thr
65                  70                  75                  80

Leu Ser Asp Tyr Asn Ile Arg Asn Pro Asp Ile Leu His Leu Val Leu
                85                  90                  95

Arg Leu Arg Ala Ala Gly Gly Gly Ser Gly Gly Gly Ser Gly
            100                 105                 110

Gly Gly Gly Ser Gln Val Gln Leu Lys Gln Ser Gly Pro Gly Leu Val
        115                 120                 125

Gln Pro Ser Gln Ser Leu Ser Ile Thr Cys Thr Val Ser Gly Phe Ser
130                 135                 140

Leu Thr Asn Tyr Gly Val His Trp Val Arg Gln Ser Pro Gly Lys Gly
145                 150                 155                 160

Leu Glu Trp Leu Gly Val Ile Trp Ser Gly Gly Asn Thr Asp Tyr Asn
                165                 170                 175

Thr Pro Phe Thr Ser Arg Leu Ser Ile Asn Lys Asp Asn Ser Lys Ser
            180                 185                 190

Gln Val Phe Phe Lys Met Asn Ser Leu Gln Ser Asn Asp Thr Ala Ile
        195                 200                 205

Tyr Tyr Cys Ala Arg Ala Leu Thr Tyr Tyr Asp Tyr Glu Phe Ala Tyr
210                 215                 220

Trp Gly Gln Gly Thr Leu Val Thr Val Ser Ala Ala Ser Thr Lys Gly
225                 230                 235                 240

Pro Ser Val Phe Pro Leu Ala Pro Ser Ser Lys Ser Thr Ser Gly Gly
                245                 250                 255

Thr Ala Ala Leu Gly Cys Leu Val Lys Asp Tyr Phe Pro Glu Pro Val
            260                 265                 270

Thr Val Ser Trp Asn Ser Gly Ala Leu Thr Ser Gly Val His Thr Phe
        275                 280                 285

Pro Ala Val Leu Gln Ser Ser Gly Leu Tyr Ser Leu Ser Ser Val Val
290                 295                 300

Thr Val Pro Ser Ser Ser Leu Gly Thr Gln Thr Tyr Ile Cys Asn Val
305                 310                 315                 320

Asn His Lys Pro Ser Asn Thr Lys Val Asp Lys Arg Val Glu Pro Lys
                325                 330                 335

Ser Cys Asp Lys Thr His Thr Cys Pro Pro Cys Pro Ala Pro Glu Leu
            340                 345                 350

Leu Gly Gly Pro Ser Val Phe Leu Phe Pro Pro Lys Pro Lys Asp Thr
        355                 360                 365

Leu Met Ile Ser Arg Thr Pro Glu Val Thr Cys Val Val Val Asp Val
370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
```

```
                435                 440                 445
Pro Ile Glu Lys Thr Ile Ser Lys Ala Lys Gly Gln Pro Arg Glu Pro
        450                 455                 460

Gln Val Tyr Thr Leu Pro Pro Ser Arg Glu Glu Met Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
530                 535                 540

Val Met His Glu Ala Leu His Asn His Tyr Thr Gln Lys Ser Leu Ser
545                 550                 555                 560

Leu Ser Pro Gly Lys
                565

<210> SEQ ID NO 111
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 111

Thr Thr Val Asp Ile
1               5

<210> SEQ ID NO 112
<211> LENGTH: 5
<212> TYPE: PRT
<213> ORGANISM: Artificial Sequence
<220> FEATURE:
<223> OTHER INFORMATION: Artificial Binding Cassette

<400> SEQUENCE: 112

Gln Asn Pro Asp Val
1               5

<210> SEQ ID NO 113
<211> LENGTH: 82
<212> TYPE: PRT
<213> ORGANISM: Artificial Sequence
<220> FEATURE:
<223> OTHER INFORMATION: Affilin 139820 Sequence

<400> SEQUENCE: 113

Met Gln Ile Phe Val Lys Thr Leu Thr Pro Trp Tyr Gly Tyr Asp Gly
1               5                   10                  15

Lys Thr Ile Thr Leu Glu Val Glu Pro Ser Asp Thr Thr Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Thr Thr Val Asp Ile Leu His Leu Val Leu Arg Leu Arg
65                  70                  75                  80

Ala Ala
```

```
<210> SEQ ID NO 114
<211> LENGTH: 82
<212> TYPE: PRT
<213> ORGANISM: Artificial Sequence
<220> FEATURE:
<223> OTHER INFORMATION: Affilin 144747 Sequence

<400> SEQUENCE: 114

Met Gln Ile Phe Val Asn Thr Leu Thr Asp Asp Lys Gly Tyr Asp Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Gln Asn Pro Asp Val Leu His Leu Val Leu Arg Leu Arg
65                  70                  75                  80

Ala Ala
```

EGFR BINDING PROTEINS

FIELD OF THE INVENTION

The present invention relates to new EGFR binding molecules based on ubiquitin muteins (Affilin®), preferably Affilin molecules having a characteristic three amino acid residue motif. The invention further refers to EGFR binding molecules that bind to different epitopes than the anti-EGFR monoclonal antibody Cetuximab. The invention refers to EGFR binding proteins optionally fused or conjugated to a pharmacokinetic moiety modulating serum half-life or to a therapeutically or diagnostically active component. The invention further relates to the use of these EGFR binding proteins in medicine, preferably for use in the diagnosis or treatment of cancer.

BACKGROUND OF THE INVENTION

Non-immunoglobulin based binding agents can be beneficially used in the medical fields of diagnosis, prophylaxis and treatment of diseases. A solution to the disadvantages resulting from antibodies in diagnosis, prophylaxis and treatment of diseases is to provide polypeptides with comparable or even better affinity and specificity towards the specific targets combined with smaller molecular size enabling an improved tissue penetration and having thus better biodistribution properties.

Among non-immunoglobulin-derived small proteins, molecules based on modified ubiquitin are particularly interesting because these molecules promise alternative therapeutic and diagnostic possibilities compared to antibodies. Ubiquitin is a highly conserved, small, single domain protein present in all known eukaryotic cells and is 100% conserved amongst all vertebrates. In addition, ubiquitin naturally occurs in serum lowering the immunogenic potential. This facilitates preclinical development in different species required for toxicological and efficacy studies. Ubiquitin muteins specific for target antigens are described in the prior art. Such ubiquitin muteins are known as Affilin® (registered trademark of Scil Proteins GmbH) molecules. Ubiquitin muteins and methods for producing these muteins were described in several patents, for example, EP1626985B1, EP2379581B1, EP2094845B1, and WO2012/172055. Affilin proteins are engineered to generate de novo binding affinity towards desired targets making them ideal for different applications.

A key feature of the Affilin platform is its flexibility and modularity allowing multiple functional moieties to be combined by genetic or chemical modifications enabling tailoring of the biological, physiological and functional properties of the resulting Affilin molecules. Affilin molecules (ubiquitin muteins) are designed for optimal functionality and developability including characteristics such as high stability, affinity and specificity. These unique features make Affilin molecules a compelling choice for applications where antibodies have limitations, thus broadening the utilization of biotherapeutics.

EGFR is a receptor tyrosine kinase mediating cell proliferation and differentiation. Increased expression of the human epidermal growth factor receptor (EGFR) is observed for many tumors, in particular in malignant tumors. EGFR is known for being involved in lung cancer, head and neck cancer and colorectal cancer amongst others. EGFR has three characteristic domains: an extracellular ligand binding domain, a transmembrane domain, and an intracellular tyrosine kinase domain. Upon binding of a ligand to the extracellular ligand binding domain, EGFR dimerizes which activates the intracellular tyrosine kinase domain and induces cellular processes such as proliferation, differentiation, migration, or apoptosis. Modulating the function of EGFR is an important approach for the development of cancer therapeutics, and meanwhile, therapeutic anti-EGFR antibodies binding to EGFR and thereby modulating the function of this receptor are available for treatments of cancer, for example colorectal cancer. One example for a monoclonal antibody binding to EGFR is Cetuximab.

However, antibodies have major disadvantages including a complex molecular structure, a large size and challenging production methods. Furthermore, treatment of diseases with currently available EGFR—binding molecules is not effective in all patients and may have severe side effects. Another major disadvantage is the development of resistances of certain tumors to Cetuximab treatment.

Cancer represents one of the leading causes for death worldwide. Needless to say that there is a strong medical need to effectively treat cancer with improved novel agents, in particular for efficient tumor targeted therapeutics and diagnostics. There is an ongoing need to substitute antibodies by smaller, less complex molecules such as non-immunoglobulin based binding agents which can be beneficially used in the medical fields of diagnosis, prophylaxis and treatment of diseases. A solution to the disadvantages resulting from antibodies in diagnosis, prophylaxis and treatment of diseases is to provide polypeptides with comparable affinity and specificity towards the specific targets, for example EGFR, combined with a less complex and smaller structure enabling a simplified molecular engineering as well as an improved tissue penetration and having thus better biodistribution properties.

Further solution to the disadvantage of the development of resistances of certain tumors to Cetuximab treatment is to provide EGFR binding molecules that bind to a different or non-overlapping epitope than Cetuximab. Novel EGFR binding molecules suitable for diagnostic and therapeutic applications should be functional and developable and should include characteristics such as high stability, affinity and specificity. Small, monovalent binders would also enable improved biophysical studies. Such small binders could also be useful for in vivo imaging in diagnostic approaches to study EGFR localization and trafficking, in addition to therapeutic approaches. It is thus an objective of the present invention to provide novel molecules for new and improved strategies in the treatment and diagnosis of various diseases, such as cancer. In particular, it is an objective to provide novel stable non-immunoglobulin proteins which have high affinity and specificity to EGFR. The invention provides small binding proteins (Affilin) which are advantageous compared to antibodies by their small size, simple molecular structure (one chain compared to four chains of an antibody), and in that no posttranslational modifications are required for full functionality. These factors contribute to an easy handling of the molecules including simple genetic engineering as well as easy production and purification methods.

A major advantage of the EGFR binding molecules of the invention is that they bind to a different (non-overlapping) epitope of the EGFR receptor than established antibodies such as Cetuximab. A positive effect of the different binding site is that these novel EGFR binding molecules may overcome the resistance of certain tumor cells to Cetuximab. Further, the binding of the EGFR binding molecules of the invention to a different epitope than Cetuximab may induce different biological responses.

The present invention meets the needs presented above by providing examples for specific EGFR binding proteins. The above-described objectives and advantages are achieved by the subject-matters of the enclosed independent claims. Preferred embodiments of the invention are included in the dependent claims as well as in the following description, examples and figures. The above overview does not necessarily describe all problems solved by the present invention.

SUMMARY OF THE INVENTION

In a first aspect of the invention, the EGFR binding protein is comprising or consisting of a ubiquitin mutein (Affilin) with binding affinity ($K_D$) of less than 700 nM for epidermal growth factor receptor (EGFR) wherein the ubiquitin mutein comprises an amino acid sequence motif wherein the amino acid in position 64 of ubiquitin is selected from P, V, and A, the amino acid in position 65 of ubiquitin is selected from D and E, and the amino acid in position 66 of ubiquitin is selected from I, V, A, M, F, Y, W, and L, and wherein the ubiquitin mutein has 80% to 93% identity to ubiquitin (SEQ ID NO: 1) or di-ubiquitin SEQ ID NO: 4. Accordingly, in a first aspect the present invention relates to an EGFR binding protein comprising a ubiquitin mutein that comprises an amino acid sequence wherein three amino acids selected from amino acids 62-66 corresponding to $X_{62}$, $X_{63}$, $X_{64}$, $X_{65}$, and $X_{66}$ of SEQ ID NO: 3 are substituted compared to the amino acid sequence QKEST and wherein the ubiquitin mutein has at least 90% sequence identity to SEQ ID NO: 3.

In a second aspect the present invention relates to an EGFR binding ubiquitin wherein the amino acid sequence in positions 64, 65, and 66 is selected from amino acids P, D, and I or amino acids V, D, and I, or amino acids A, D, and I, or amino acids V, D, and V, or amino acids P, D, and V ("PDI motif"; including amino acid sequences PDI, VDI, VDV, PDV, or ADI). In one aspect of the invention, the EGFR binding protein comprises an ubiquitin mutein wherein the amino acids in positions 62 and 63 may be any amino acid, preferably wherein the amino acid in position 62 is selected from R, Q, H, K, G, S, T, N, V, I, and W, and wherein the amino acid in position 63 is selected from N, H, A, S, R, E, T, Q, and K.

In a third aspect the present invention relates to an EGFR binding protein that binds to a different or non-overlapping EGFR epitope than anti-EGFR monoclonal antibody Cetuximab.

A further aspect of the present invention relates to an EGFR binding protein comprising or consisting of at least two ubiquitin muteins of the same (e.g., homo-dimer) or a different (e.g. hetero-dimer) target specificity and/or binding to the same (overlapping) or a different (non-overlapping) epitope of EGFR.

A further aspect of the invention relates to an EGFR binding protein comprising or consisting of a ubiquitin mutein comprising an amino acid sequence selected from at least one member of the group consisting of SEQ ID NOs: 8-73 and 90-106 and 111-112 or an amino acid sequence that exhibits at least 80% sequence identity to one or more of the amino acid sequences of SEQ ID NOs: 8-73 and 90-106 and 111-112.

Another aspect the present invention relates to an EGFR binding ubiquitin mutein further comprising at least one additional molecule, preferably selected from at least one member of the groups (i), (ii) and (iii) consisting of (i) a pharmacokinetic moiety modulating serum half-life selected for example from a polyethylene glycol, a human serum albumin (HSA), anti-human serum albumin binding protein, albumin-binding peptides, a polymer sequence forming a random coil, an immunoglobulin or immunoglobulin fragments, or a polysaccharide, and, (ii) a therapeutically active component, optionally selected for example from a monoclonal antibody or a fragment thereof with the binding specificity of said monoclonal antibody, a cytokine, a chemokine, a cytotoxic compound, an enzyme, or derivatives thereof, or a radionuclide, and (iii) a diagnostic component, optionally selected for example from a fluorescent compound, a photosensitizer, or a radionuclide.

The present invention also provides, in further aspects, a nucleic acid or nucleic acids encoding the EGFR binding protein comprising or consisting of a ubiquitin mutein of the present invention, as well as a vector or vectors comprising said nucleic acid or nucleic acids, and a host cell or host cells comprising said vector or vectors. Another aspect relates to an EGFR binding protein comprising or consisting of a ubiquitin mutein of the invention binding to EGFR for use in diagnostics or medicine, preferably for use in the diagnosis or treatment of cancer, or a nucleic acid molecule encoding said EGFR binding protein comprising or consisting of a ubiquitin mutein of the invention, or to a vector comprising said EGFR binding protein comprising or consisting of a ubiquitin mutein of the invention, or to a host cell comprising said EGFR binding protein comprising or consisting of a ubiquitin mutein of the invention, or to a non-human host comprising said EGFR binding protein comprising or consisting of a ubiquitin mutein of the invention.

Another aspect relates to a composition comprising the EGFR binding protein of the invention, the nucleic acid molecule of the invention, the vector of the invention, or the host cell of the invention, preferably for use in the diagnosis or treatment of cancer.

Another aspect of the present invention relates to a method for the production of an EGFR binding protein comprising or consisting of a ubiquitin mutein (Affilin) of any of the preceding aspects of the invention comprising culturing of host cells under suitable conditions and optionally isolation of the EGFR binding ubiquitin mutein produced. This summary of the invention does not necessarily describe all features of the present invention. Other embodiments will become apparent from a review of the ensuing detailed description.

BRIEF DESCRIPTION OF THE FIGURES

The Figures show:

FIG. 1 shows anti-EGFR Affilin molecules and biochemical characterization of EGFR binding Affilin molecules. Binding affinity ($K_D$) or binding data for the Affilin molecules to EGFR have been obtained from SPR (Biacore) and are shown in the fifth column. Temperature stability is shown (DSF) in the sixth column. Exchanges at positions 62, 63, 64, 65, and 66 of unmodified ubiquitin are shown in the last column. All assays are further described in the Examples section.

Affilin with one ubiquitin moiety: Six amino acids inserted in the N-terminal loop region of ubiquitin are shown in brackets in the third column of the table. Substitutions in positions 62-66 of ubiquitin are shown after the bracket in the third column of the table and are additionally shown in the last column of the table. Further substitutions relevant for EGFR-binding are listed for some variants (fourth column). All variants have a characteristic amino acid residue motif of three amino acids ("PDI motif") in positions 64, 65, and 66 of ubiquitin. SEQ ID NOs: 8-52 are Affilin molecules binding to EGFR and having a PDI motif at position 64, 65, and 66 of wildtype ubiquitin.

Affilin comprising two ubiquitin moieties: Affilin molecules with SEQ ID NOs: 53-73 correspond to Affilin molecules comprising two different Affilin moieties with substitutions in amino acid residues 6 and 8, and in residues 62, 63, 64, 65, 66 in each moiety (as shown in the third column of the table). A PDI motif is located in the first moiety of the ubiquitin mutein. Two proteins without PDI motif (Affilin 139989 and Affilin 138840) do not bind to extracellular EGFR.

FIG. 2 shows a functional characterization of EGFR-Affilin molecules. The figure shows binding to exogenously EGFR expressing CHO-K1 cells as determined by FACS analysis. These cells are used as model system for testing EGFR binding capability. Affilin molecules show binding on CHO-K1-EGFR cells and no activity on control cells. EGFR binding Affilin molecules with PDI motif (or Cetuximab) are shown in black, whereas the PBS control is shown in grey. Cellular EGFR binding was confirmed for all binding molecules (FIG. 2B Affilin 139756 (SEQ ID NO: 50), FIG. 2C Affilin 139791 (SEQ ID NO: 49), FIG. 2D Affilin 139819 (SEQ ID NO: 39), and FIG. 2H Affilin 142265 (SEQ ID NO: 75)). No or weak binding was observed for an Affilin without PDI motif (Affilin 139989, SEQ ID NO: 76, FIG. 2E). Cetuximab served as positive control for EGFR expression (FIG. 2A). FIG. 2F shows non-binding to negative control cells for 139819 (SEQ ID NO: 39) and FIG. 2G for Cetuximab.

FIG. 3 shows a FACS analysis of Affilin 139819 (SEQ ID NO: 39) with decreasing Affilin concentrations. 500 nM (FIG. 3a), 50 nM (FIG. 3B), 5 nM (FIG. 3c), and 0.5 nM (FIG. 3D) Affilin 139819 was assayed for binding to CHO-K1-EGFR cells. Even for the lowest used concentration, binding of Affilin 139819 to cellular EGFR was detectable.

FIG. 4 shows the epitope specificity of EGFR binding molecules with or without PDI motif. Binding analysis (SPR) shows that the binding epitope of both Affilin molecules with PDI motif (Affilin 139791 and Affilin 139819) is identical or at least overlapping whereas the binding epitope of Affilin 139989 without PDI motif is different.

Figure 2A:
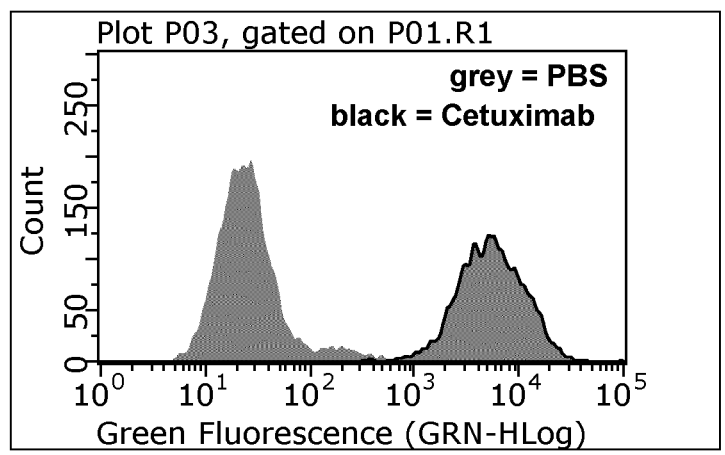
Figure 2B:
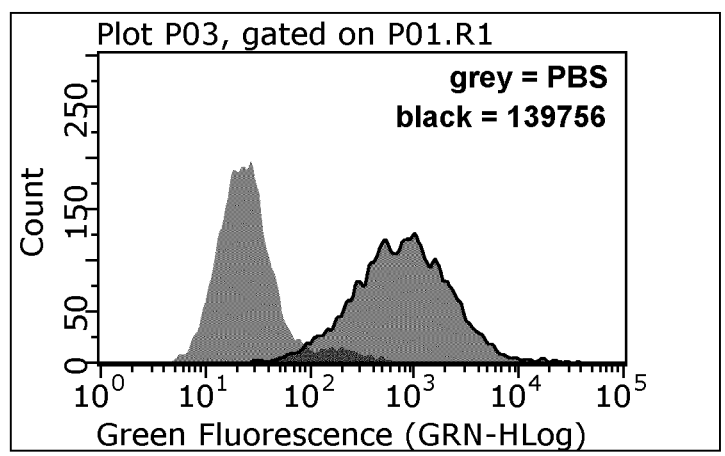
Figure 2C:
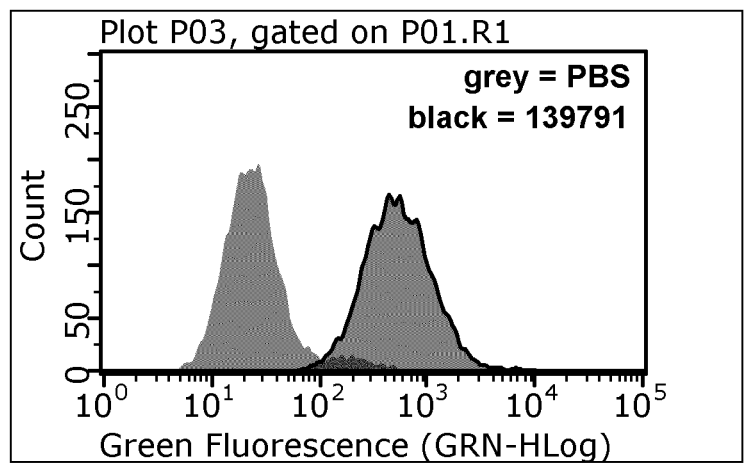
Figure 2D:
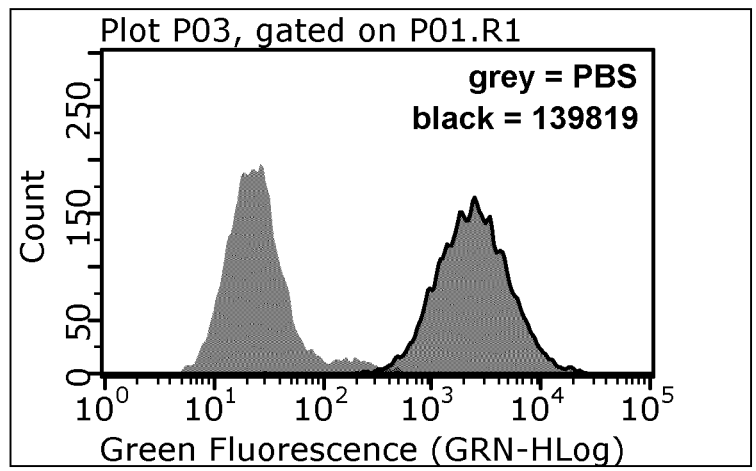
Figure 2E:
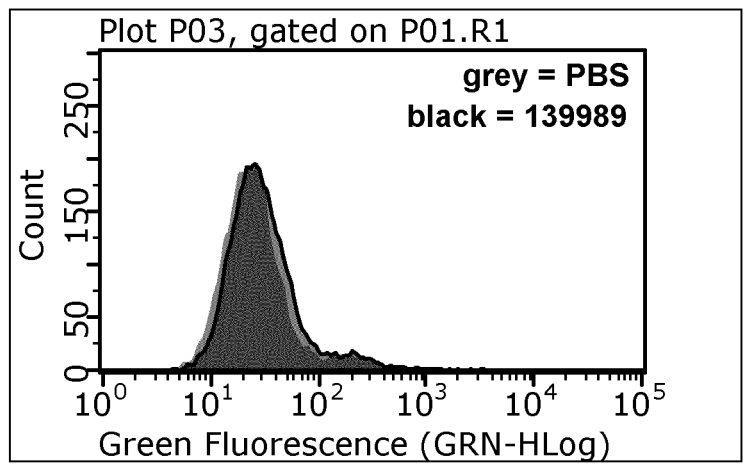
Figure 2F:
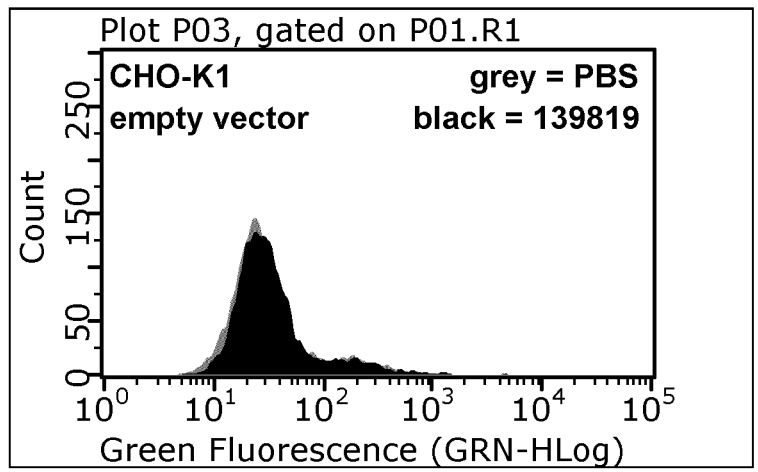
Figure 2G:
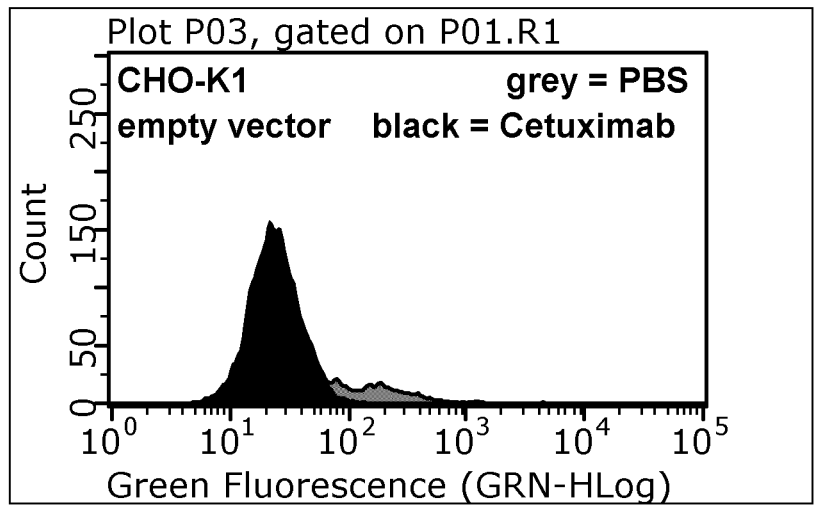
Figure 2H:
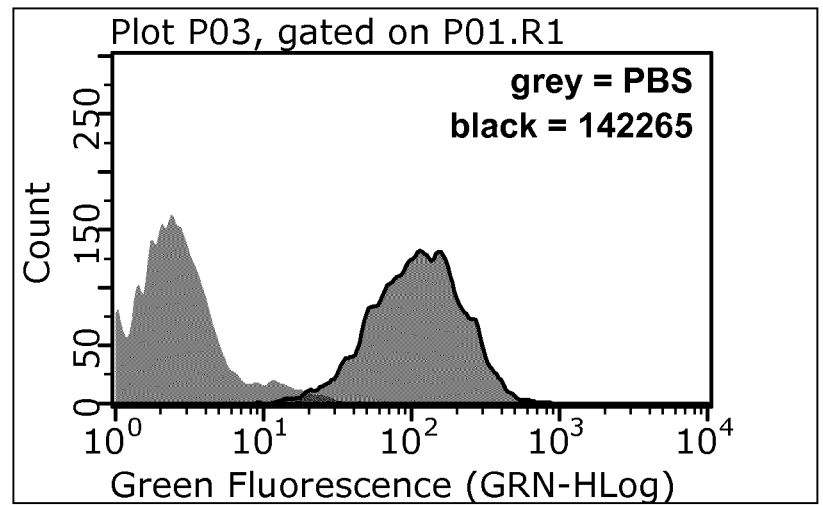
Figure 3A:
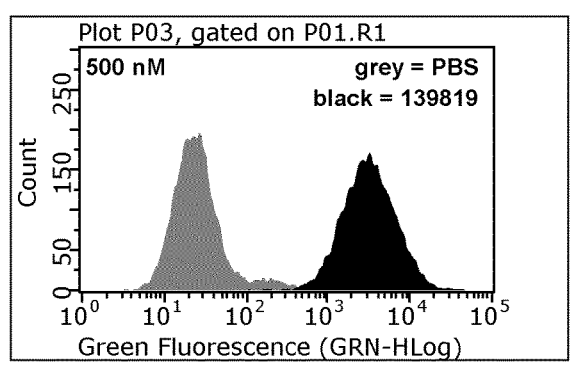
Figure 3B:
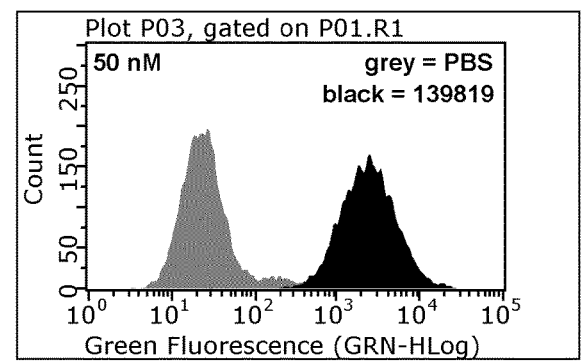
Figure 3C:
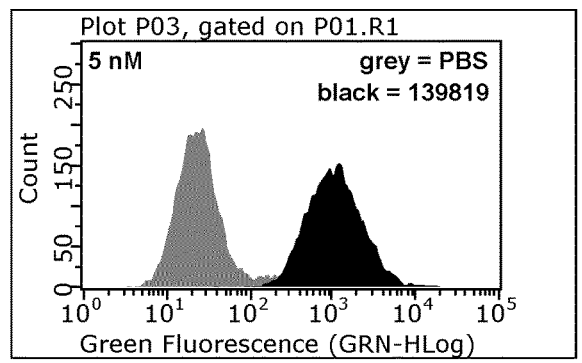
Figure 3D:
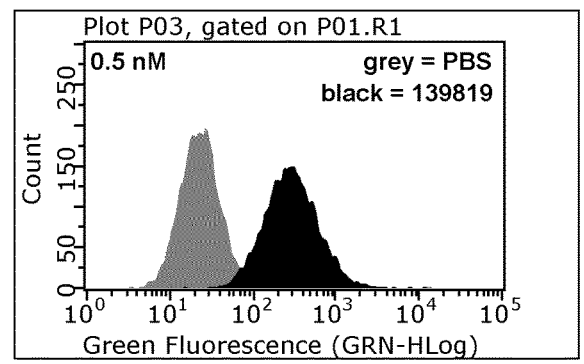
Figure 4A:
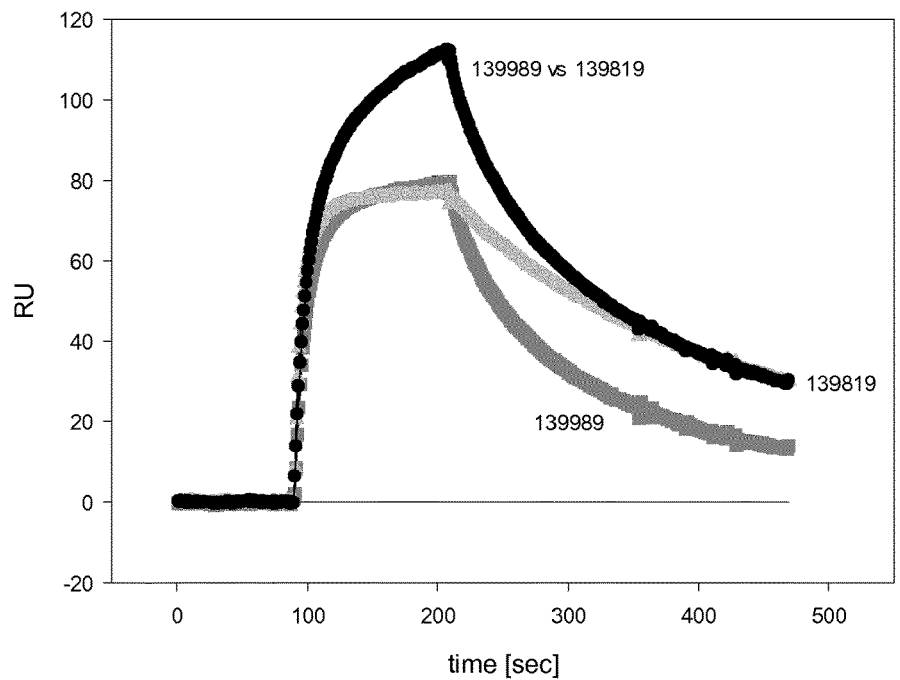

FIG. 4A. SPR analysis of Affilin 139819 (PDI motif) versus Affilin 139989

Figure 4B:
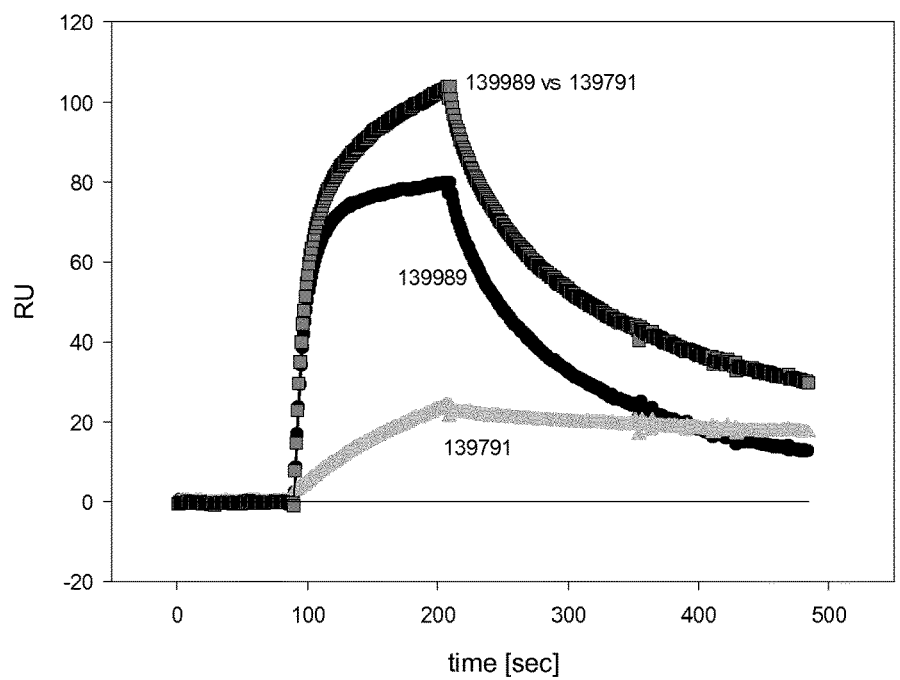

FIG. 4B. SPR analysis of Affilin 139791 (PDI motif) versus Affilin 139989

Figure 4C:
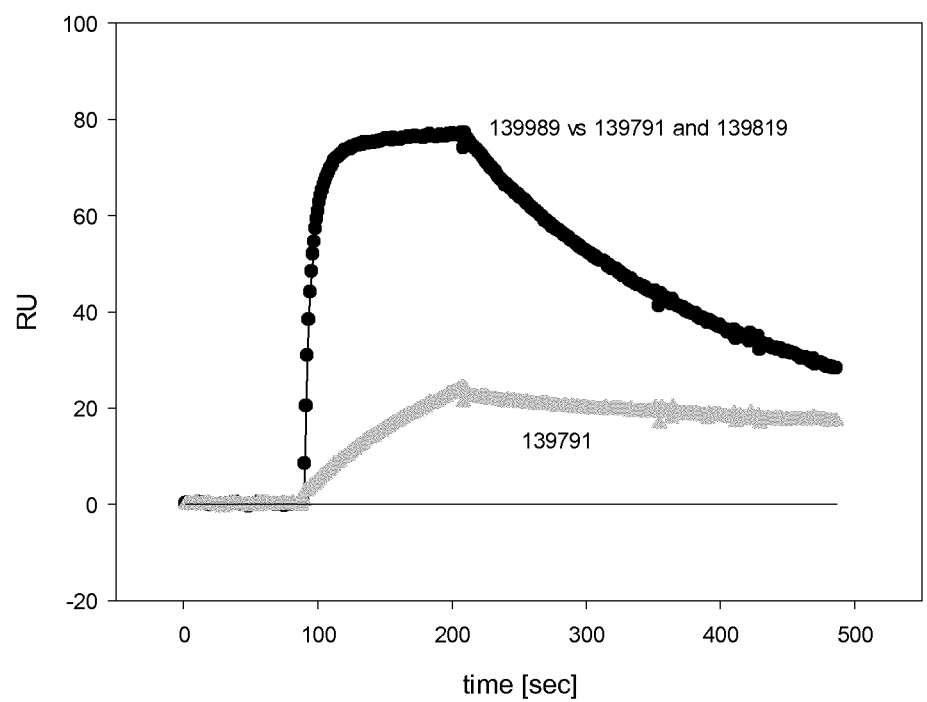

FIG. 4C. SPR analysis of Affilin 139989 (no PDI) versus Affilin 139819 (PDI motif) and Affilin 139791 (PDI motif)

Figure 5:
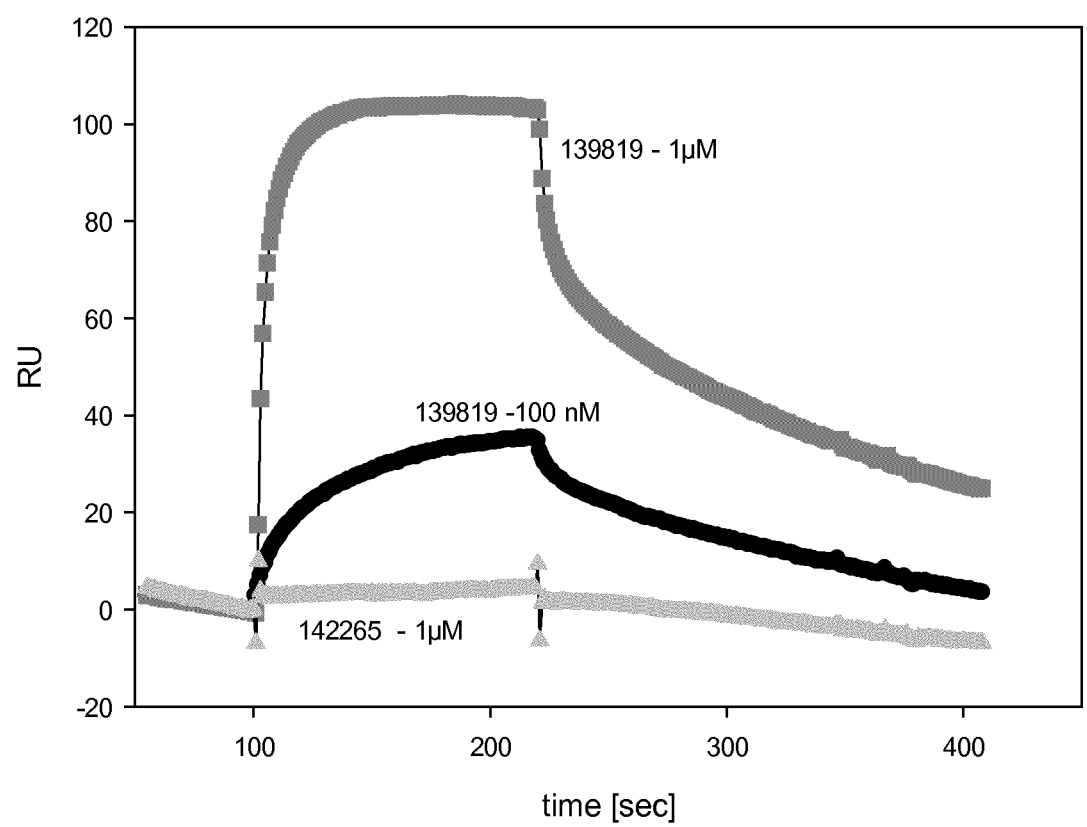

FIG. 5 shows a SPR competition analysis of Affilin 139819 and Affilin 142265 with Cetuximab. Affilin 139819 (SEQ ID NO: 39; 100 nM) is shown as black line in the middle of the diagram and 10 µM is shown as medium grey line on top, 1 µM Affilin 142265 (SEQ ID NO: 75) is shown as light grey line at the bottom of the figure. The analysis is described in further detail in Example 7. The Figure shows that Affilin 139819 does not compete with Cetuximab and that Affilin 139819 uses a different or non-overlapping epitope whereas Affilin 142265 (no PDI motif) competes with Cetuximab. The result surprisingly shows that the Affilin binding molecules with PDI motif bind to a different or non-overlapping EGFR epitope than Cetuximab whereas the Affilin binding molecules without PDI motif bind to the same or overlapping EGFR epitope.

Figure 6:
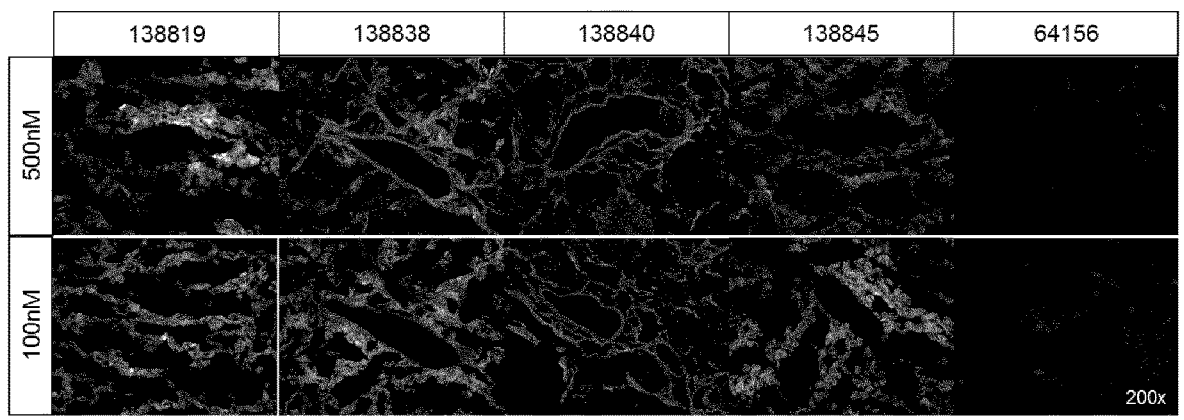

FIG. 6 confirms that anti-EGFR-Affilin proteins having a PDI motif bind to tumor tissue. Shown is an immunohistological analysis on EGFR expressing human xenograft tumor tissue (MDA-MB-231; ATTC HTB-26), derived from metastatic site of mammary gland/breast adenocarcinoma, epithelial cells. Different concentrations (100 nM and 500 nM) were tested of Affilin proteins with PDI motif 138819 (SEQ ID NO: 71), Affilin 138838 (SEQ ID NO: 69), Affilin 138845 (SEQ ID NO: 73), and Affilin without PDI motif 138840 (SEQ ID NO: 77). Positive control: Cetuximab (not shown in this figure), negative control: unmodified ubiquitin (SEQ ID NO: 7, clone 64156). No unspecific staining was detected with unmodified ubiquitin. The results clearly show the high specific targeting function of EGFR binding proteins of the invention. All Affilin binding proteins with PDI motif show strong binding to EGFR on xenografts derived from human tumor tissue whereas the Affilin binding molecule without PDI motif shows only weak binding to EGFR.

Figure 7:
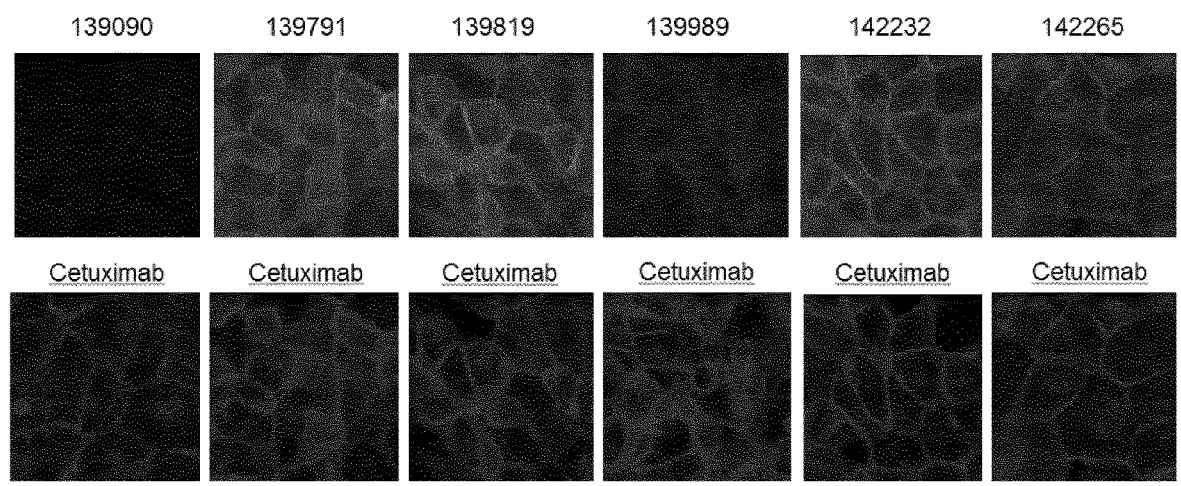

FIG. 7 confirms that EGFR-Affilin proteins bind to extracellular EGFR expressed on tumor cells. Shown are immunofluorescence images of EGFR expressing A431 tumor cells. The staining of A431 tumor cells expressing EGFR confirms binding of Affilin 139791 (SEQ ID NO: 49), Affilin139819 (SEQ ID NO: 39), Affilin 142232 (SEQ ID NO: 29) and Affilin 142265 (SEQ ID NO: 75). For Affilin 139989 (no PDI motif; SEQ ID NO: 76), no binding to extracellular EGFR on A431 tumor cells was detectable. The unmodified ubiquitin is referred to as 139090 (SEQ ID NO: 4) in this Figure.

FIG. 8 shows fusion proteins of EGFR binding proteins with Cetuximab. Shown are the sensorgrams of EGFR-monoclonal antibody Cetuximab (SEQ ID NOs: 5 and 6), control fusion of Cetuximab with unmodified ubiquitin, and fusion protein of Cetuximab and EGFR-Affilin 139819. The curves show different concentrations of 15 nM (highest) to 0.0586 nM (lowest) in a 1:2 dilution. A RU results from the calculation of the subtraction of the signals for both flow cells (hEGFR-Fc 1578 RU; hIgG-Fc 331 RU). The analysis confirms that fusion proteins of an anti-EGFR-Affilin to a monoclonal antibody binds to EGFR with high affinity.

Figure 8A:
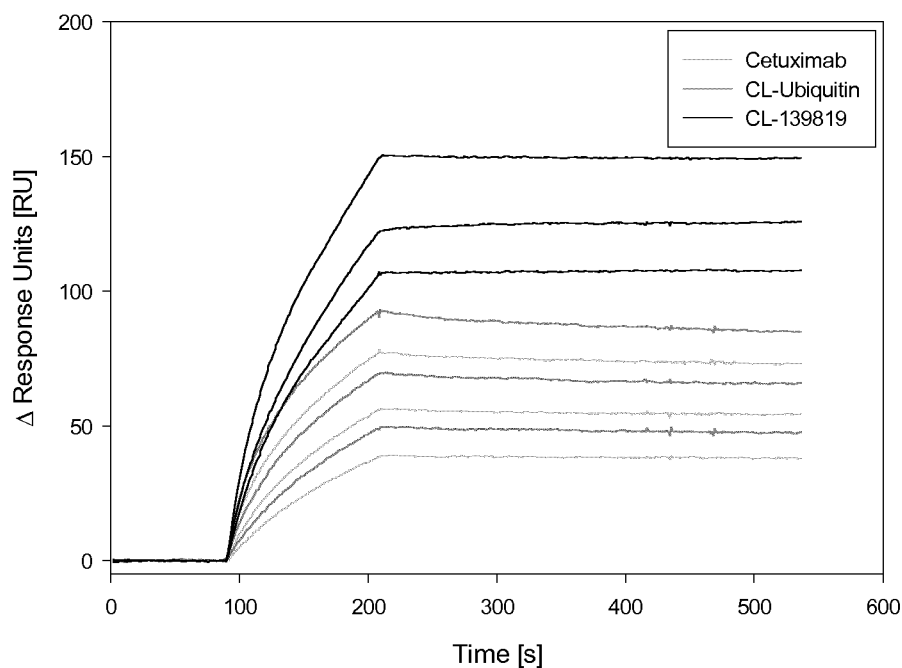

FIG. 8A shows the SPR analysis of the binding of an anti-EGFR-Affilin-Cetuximab fusion protein to the extracellular domain of EGFR. Shown are sensorgrams of Cetuximab, CL-ubiquitin, and CL-139819. Anti-EGFR-Affilin fused to the C-terminus of the light chain of Cetuximab shows higher signal intensity to EGFR than Cetuximab.

Figure 8B:
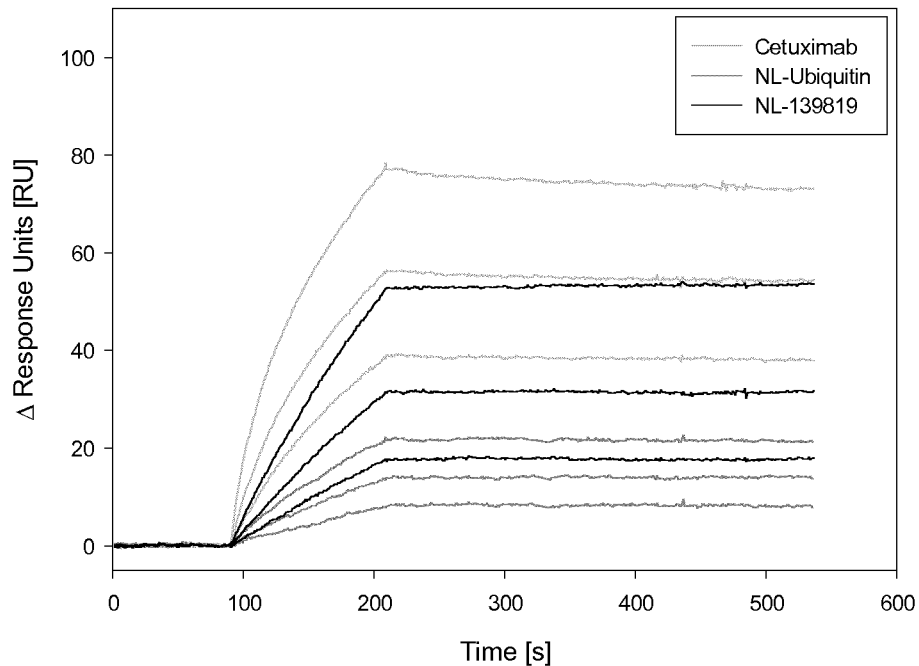

FIG. 8B shows the SPR analysis of the binding of an anti-EGFR-Affilin-Cetuximab fusion protein. Shown are sensorgrams of Cetuximab, NL-ubiquitin (SEQ ID NO: 89), and NL-139819 (SEQ ID NO: 86).

FIG. 9 shows the expression and purification of a homo-dimer of two identical Affilin 139819 proteins. The final product yield of the homo-dimer was 5.9 mg per liter expression.

Figure 9A:
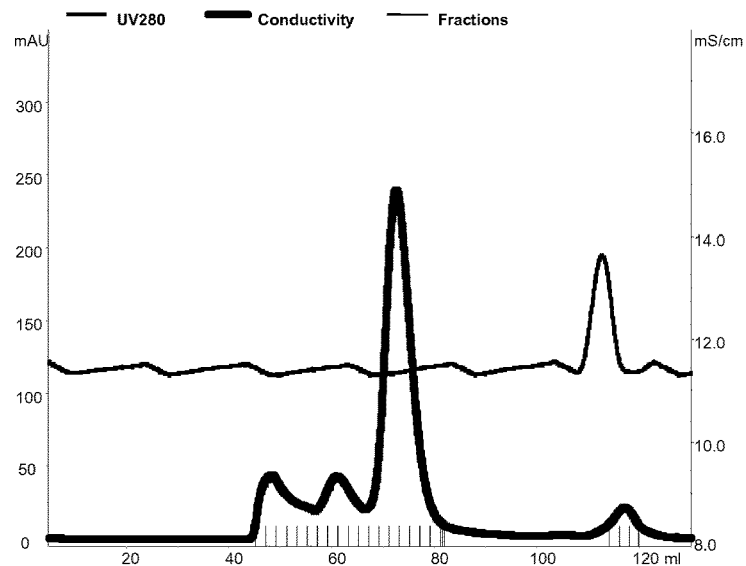

FIG. 9A shows the polishing step after StrepTactin purification via gelfiltration on Superdex 75 16/60, the primary axis plots the absorption signal [mAU] against buffer volume [ml] and the secondary axis plots the conductivity [mS/cm] versus the buffer volume [ml].

Figure 9B:
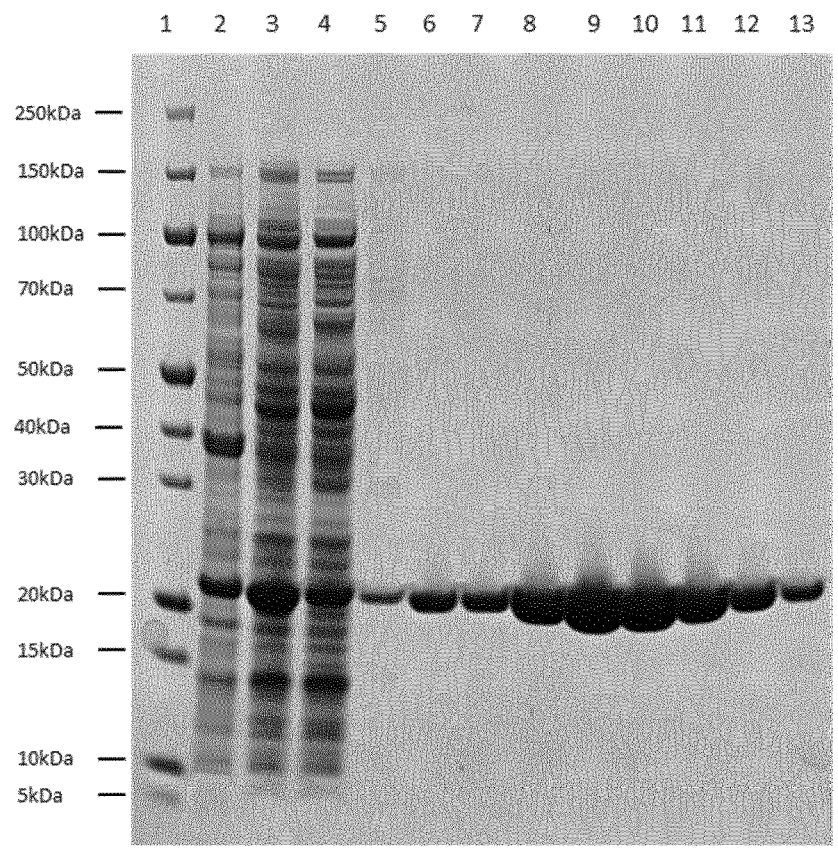

FIG. 9B shows SDS-PAGE analysis of the gelfiltration. Lane 1, protein marker, lane 2, pellet, lane 3 supernatant, lane 4 flow through (StrepTactin), lane 5 fraction A3, lane 6 fraction A9, lane 7 fraction B12, lane 8 fraction B11, lane 9 fraction B10, lane 10 fraction B9, lane 11 fraction B8, lane 12 fraction B7, lane 13 fraction B6. The product purity is higher than 95% according to SDS-PAGE.

Figure 10:
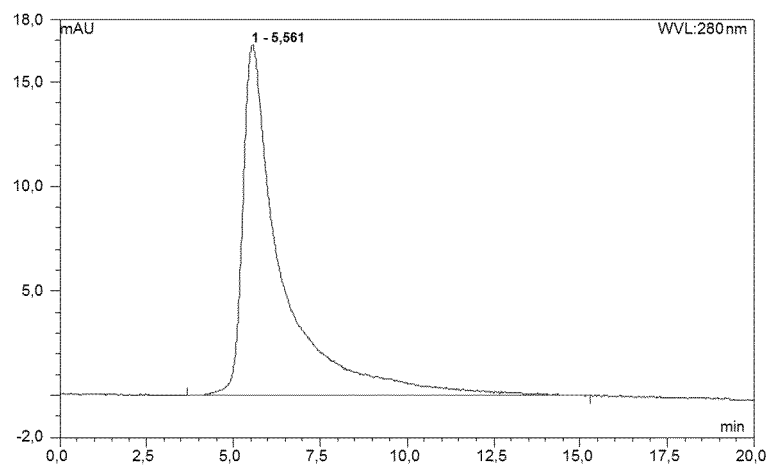

FIG. 10 shows the analysis of purity and homogeneity via SEHPLC of a homo-dimer of two identical Affilin 139819 proteins. During the analysis only one peak could be detected. The observed tailing is likely a result of the peptide linker connecting both ubiquitin moieties. The primary axis plots the absorption signal [mAU] against buffer volume [ml] and the secondary axis plots the conductivity [mS/cm] versus the buffer volume [ml].

Figure 11:
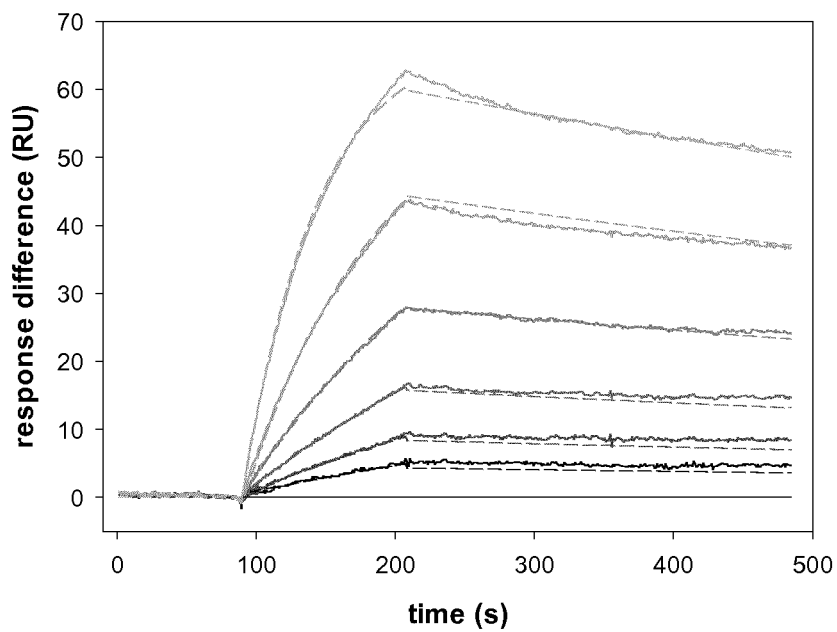

FIG. 11 shows surface plasmon resonance spectroscopy (Biacore) of a homo-dimer of two Affilin 139819 molecules to determine the dissociation constants of binding proteins-target complexes. Solid lines represent experimental data, dashed lines represent fitted curve data. The Affilin proteins demonstrate a quick association as well as a prompt dissociation, eliciting rather high $k_{off}$ rates. Highest affinities to EGFR-Fc have an KD of 0.6 nM. The affinity of the homo-dimer (139819-139819) to extracellular EGFR is about 30 fold higher than for the monomer Affilin 139819.

FIG. 12 shows functional characterization of the binding of a homo-dimeric EGFR Affilin.

FIG. 12A and FIG. 12B show binding to EGFR expressing CHO-K1 cells, for example of the homo-dimer of two Affilin 139819 proteins (referred to as 140547 in the Figure; dissociation constant 1.7 nM, FIG. 12A) and of Affilin 139819 (dissociation constants 8.7 nM, FIG. 12B).

FIG. 12C and FIG. 12D shows binding to EGFR expressing A549 cells, for example of the homo-dimer of two Affilin molecules 139819 (dissociation constant 1.7 nM, FIG. 12C) and of Affilin 139819 (dissociation constants 10.9 nM, FIG. 12D). The affinity of the homo-dimer of two Affilin molecules 139819 to extracellular EGFR is about 10 fold higher than for the monomer Affilin 139819.

DETAILED DESCRIPTION OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Throughout this specification and the claims which follow, unless the context requires otherwise, the word "comprise", and variants such as "comprises" and "comprising", will be understood to imply the inclusion of a stated integer or step or group of integers or steps but not the exclusion of any other integer or step or group of integers or steps. Several documents (for example: patents, patent applications, scientific publications, manufacturer's specifications, instructions, GenBank Accession Number sequence submissions etc.) are cited throughout the text of this application. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence. All sequences referred to herein are disclosed in the attached sequence listing that, with its whole content and disclosure, is a part of this specification.

General Definitions of Important Terms Used in the Application

The terms "protein" and "polypeptide" refer to any chain of two or more amino acids linked by peptide bonds, and does not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well known in the art. Thus, binding proteins comprising two or more protein moieties also fall under the definition of the term "protein" or "polypeptides".

The term "ubiquitin" or "unmodified ubiquitin" refers to ubiquitin in accordance with SEQ ID NO: 1 (wild type ubiquitin) or to proteins with at least 95% amino acids identity to SEQ ID NO: 1 (for example, with point mutations in positions W45F, G75A, G76A which do not influence binding to a target, see SEQ ID NO: 2) and according to the following definition. Particularly preferred are ubiquitin molecules from mammals, e.g. humans, primates, pigs, and rodents. On the other hand, the ubiquitin origin is not relevant since according to the art all eukaryotic ubiquitins are highly conserved and the mammalian ubiquitins examined up to now are even identical with respect to their amino acid sequence. In addition, ubiquitin from any other eukaryotic source can be used. For instance ubiquitin of yeast differs only in three amino acids from the wild-type human ubiquitin (SEQ ID NO: 1).

The term "di-ubiquitin" refers to a linear protein wherein two ubiquitin moieties are directly fused to each other in head to tail orientation. The term "di-ubiquitin" refers to two directly linked ubiquitin moieties of SEQ ID NO: 1 or to proteins with at least 95% amino acids identity to SEQ ID NO: 4 (for example, with point mutations in positions W45F, G75A, G76A, G151A, G152A).

The term "Affilin®" (registered trademark of Scil Proteins GmbH) refers to non-immunoglobulin derived binding proteins based on ubiquitin muteins. The terms "modified ubiquitin" and "ubiquitin mutein" and "Affilin" are all used synonymously and can be exchanged. The term "modified ubiquitin" or "ubiquitin mutein" or "Affilin" as used herein refers to derivatives of ubiquitin (for example, derived from SEQ ID NO: 1 or SEQ ID NO: 3) or di-ubiquitin (for example, SEQ ID NO: 4) which differ from said unmodified ubiquitin by amino acid exchanges, insertions, deletions or any combination thereof, provided that the modified ubiquitin or ubiquitin mutein has a specific binding affinity to a target epitope or antigen which is at least 10 fold lower or absent in unmodified ubiquitin. This functional property of an ubiquitin mutein (Affilin; modified ubiquitin) is a de novo created function.

An Affilin is not a natural ubiquitin existing in or isolated from nature. The scope of the invention preferably excludes unmodified ubiquitin for example, as shown in SEQ ID NO: 1. An Affilin molecule according to this invention comprises or consists of either one modified ubiquitin moiety or comprises two differently modified ubiquitin moieties linked together in a head-to-tail fusion. A "head-to-tail fusion" is to be understood as fusing two proteins together by connecting them in the direction (head) N—C—N—C— (tail) (tandem molecule), as described for example in EP2379581B1 which is incorporated herein by reference. The head part is designated as the first moiety and the tail part as the second moiety. In this head-to-tail fusion, the ubiquitin moieties may be connected directly without any linker. Alternatively, the fusion of ubiquitin moieties can be performed via linkers, for example, a polypeptide linker, as described herein.

As used herein, "substitutions" are defined as exchanges of an amino acid by another amino acid. Given the known genetic code, and recombinant and synthetic DNA techniques, the skilled scientist can readily construct DNAs encoding the amino acid variants. The term "deletion" means that one or more amino acids are taken out of the original sequence and the amino acids originally N-terminal and C-terminal of the deleted amino acid are now directly connected and for a continuous amino acid sequence.

The term "insertions" comprises the addition of amino acids to the original amino acid sequence of ubiquitin wherein the ubiquitin remains stable without significant structural change. Naturally, loop regions connect regular secondary structure elements. The structure of human unmodified ubiquitin reveals six loops at amino acid regions 8-11, 17-22, 35-40, 45-47 and 50-63 which connect secondary structure elements such as beta sheets and alpha helix. Preferred are ubiquitin muteins comprising a combination of insertions and substitutions, as described in EP2721152. Preferred ubiquitin muteins have insertions of 2-10 amino acids, preferably in the most N-terminal loop within amino acids 8-11 or in the most C-terminal loop within amino acids 50-63. However, other locations for insertions are possible. Specifically, the number of amino acids to be inserted is 2, 3, 4, 5, 6, 7, 8, 9, 10, preferably 2-8 amino acids, most preferred 4-8 amino acids.

The term "EGFR binding protein" refers to a protein which either consists of or comprises at least one ubiquitin mutein (Affilin), and optionally comprising other molecules or modifications.

In the present specification, the terms "target antigen", "target", "ligand" "antigen" and "binding partner" are all used synonymously and can be exchanged. Preferably the target is one of the targets defined herein below. The term "antigen", as used herein, is to be interpreted in a broad sense and includes any target moiety that is bound by the the binding proteins. The term "antigen" is not particularly limited in its structure, as long as it comprises epitopes to which antigen-binding domains present in the binding protein bind.

The terms "protein capable of binding" or "binding protein" or "binding EGFR" or "binding affinity for" according to this invention refer to a protein comprising a binding capability to a defined target antigen.

An "antigen binding site" refers to the site, i.e. one or more amino acid residues, of an antigen binding molecule which provide interaction with the antigen. For example, the antigen binding site of an antibody comprises amino acid residues from the complementarity determining regions. A native immunoglobulin molecule typically has two antigen binding sites, a Fab molecule typically has a single antigen binding site.

The term "antibody" as used in accordance with the present invention comprises monoclonal antibodies having two heavy chains and two light chains (immunoglobulin or IgG antibodies). Furthermore, also fragments or derivatives thereof, which still retain the binding specificity, are comprised in the term "antibody". The term "antibody" also includes embodiments such as chimeric (human constant domain, non-human variable domain), single chain and humanized (human antibody with the exception of non-human CDRs) antibodies. Full-length IgG antibodies consisting of two heavy chains and two light chains are most preferred in this invention. Heavy and light chains are connected via non-covalent interactions and disulfide bonds. A "Fab molecule" refers to a protein consisting of the VH and CH domain of the heavy chain and the VL and CL domain of the light chain of an immunoglobulin.

The term "epitope" includes any molecular determinant capable of being bound by an EGFR binding protein. An epitope may include specific amino acids that directly contact the EGFR binding protein. In a conformational epitope, amino acid residues are separated in the primary sequence, but are located near each other on the surface of the molecule when the polypeptide folds into the native three-dimensional structure. A linear epitope is characterized by two or more amino acid residues which are located adjacent in a single linear segment of a protein chain. The epitope may include determinants from posttranslational modifications of the target protein such as glycosylation, phosphorylation, sulfation, acetylation, fatty acids or others.

The term "fused" means that the components (e.g. an Affilin molecule and a monoclonal antibody or a Fab fragment) are linked by peptide bonds, either directly or via peptide linkers.

The term "fusion protein" relates to a protein comprising at least a first protein joined genetically to at least a second protein. A fusion protein is created through joining of two or more genes that originally coded for separate proteins. Thus, a fusion protein may comprise a multimer of different or identical binding proteins which are expressed as a single, linear polypeptide. It may comprise one, two, three or even more first and/or second binding proteins. A fusion protein as used herein comprises at least a first binding protein (e.g. Affilin) which is fused with at least a second binding protein, e.g. a monoclonal antibody or a fragment thereof. Such fusion proteins may further comprise additional domains that are not involved in binding of the target, such as but not limited to, for example, multimerization moieties, polypeptide tags, polypeptide linkers.

The term "conjugate" as used herein relates to a protein comprising or essentially consisting of at least a first protein attached chemically to other substances such as to a second protein or a non-proteinaceous moiety. The conjugation can be performed by means of organic synthesis or by use of enzymes including natural processes of enzymatic post-translational modifications. Examples for protein conjugates are glycoproteins (conjugated protein with carbohydrate component) or lipoproteins (conjugated protein with lipid component). The molecule can be attached e.g. at one or several sites through any form of a linker. Chemical coupling can be performed by chemistry well known to someone skilled in the art, including substitution (e.g. N-succinimidyl chemistry), addition or cycloaddition (e.g. maleimide chemistry or click chemistry) or oxidation chemistry (e.g. disulfide formation). Some examples of non-proteinaceous polymer molecules which are chemically attached to protein of the invention are hydroxyethyl starch, polyethylene glycol, polypropylene glycol, dendritic polymers, or polyoxyalkylene and others.

A fusion protein or protein conjugate may further comprise one or more reactive groups or peptidic or non-peptidic moieties such as ligands or therapeutically or diagnostically relevant molecules such as radionuclides or toxins. It may also comprise small organic or non-amino acid based compounds, e.g. a sugar, oligo- or polysaccharide, fatty acid, etc. Methods for attaching a protein of interest to such non-proteinaceous components are well known in the art, and are thus not described in further detail here.

The terms "bispecific binding molecule", "trispecific binding molecule", "multispecific binding molecule" mean that the antigen binding molecule is able to specifically bind two, three or multiple different epitopes, respectively. Typically, a bispecific antigen binding molecule comprises two antigen binding sites, each of which is specific for a different epitope. In certain embodiments the bispecific antigen binding molecule is capable of simultaneously binding two epitopes, particularly two epitopes expressed on two distinct cells. The term "bispecific binding molecule" or "bispecific binding protein" means that binding proteins of the present invention are capable of specifically binding to two different epitopes. Moreover, the bispecific binding molecule of the present invention is capable of binding to two different epitopes at the same time. This means that a bispecific construct is capable of simultaneously binding to at least one epitope "A" and at least one epitope "B", wherein A and B are not the same. The two epitopes may be located on the same or different target antigens which means that the fusion molecules of the present invention can bind one target at two different epitopes or two target antigens each with its own epitope. Similarly, "trispecific binding molecules" and "multispecific binding molecules" are capable of binding three or multiple epitopes at the same time, respectively, wherein the epitopes may be located on the same or different antigens.

The term "multivalent binding molecule" means that the fusion protein of the present invention comprises at least two, three, or more binding proteins, e.g. protein "α", "β", "γ", "δ" etc. Said binding proteins may bind specifically to the same or overlapping epitopes on a target antigen (monospecific), e.g. the composition of the fusion protein may be described by $(\alpha)_2$, $(\alpha)_3$, $(\alpha)_4$ or $(\beta)_2$, $(\beta)_3$, $(\beta)_4$ etc. In this case, the fusion molecules are monospecific but bivalent, trivalent, tetravalent or multivalent for the epitope A or epitope B, respectively.

Alternatively, said binding proteins may bind to different epitopes on the same or different target molecules and are thus classified as bispecific, trispecific, multispecific, etc., for example αβ, βγ, αδ, αβγ, αβγδ binding to epitopes AB, BC, AD, ABC or ABCD, respectively.

The term "multimeric binding molecules" refers to fusion proteins that are multivalent and/or multispecific, comprising two or more moieties (i.e. bivalent or multivalent) of binding protein α, β and/or γ etc., e.g. αα, βββ, ααβ, ααββ, αγγ, ββγ, αβγδ, etc. For example, ααβγ is trispecific and bivalent with respect to epitope A. For example, the fusion proteins of anti-EGFR-Affilin and monoclonal antibodies as described herein are at least "bivalent" because they comprise at least two binding proteins (Affilin and antibody).

Said binding proteins may bind specifically to the same or overlapping epitopes on a target antigen (monospecific), e.g. the composition of the binding protein may be described by $(\alpha)_2$, $(\alpha)_3$, $(\alpha)_4$ or $(\beta)_2$ $(\beta)_3$, $(\beta)_4$ etc. In this case, the fusion molecules are monospecific but bivalent, trivalent, tetravalent, or multivalent for the epitope A or epitope B, respectively.

Alternatively, said binding proteins may bind to different, non-overlapping epitopes on the same or different target molecules and are thus classified as bispecific, trispecific, multispecific, etc., for example αβ, βγ, αδ, αβγ, αβγδ binding to epitopes AB, BC, AD, ABC or ABCD, respectively. For example, the binding proteins of the invention comprising a Fab-fragment are bispecific.

The term "multimeric binding molecules" refers to binding proteins that are multivalent and/or multispecific, comprising two or more moieties of binding protein α, β and/or γ etc., e.g. αα, βββ, ααβ, ααββ, αγγ, ββγ, αβγδ, etc. For example, ααβγ is trispecific and bivalent with respect to epitope A.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity.

To determine the sequence identity, the sequence of a query protein is aligned to the sequence of a reference protein, for example, to unmodified ubiquitins as shown in SEQ ID NO: 1, SEQ ID NO: 2, SEQ ID NO: 3, or SEQ ID NO: 4. Methods for alignment are well known in the art. For example, for determining the extent of an amino acid sequence identity of an arbitrary polypeptide relative to the amino acid sequence of SEQ ID NO: 1, SEQ ID NO: 2, SEQ ID NO: 3, or SEQ ID NO: 4, the SIM Local similarity program is preferably employed (Xiaoquin Huang and Webb Miller (1991), Advances in Applied Mathematics, vol. 12: 337-357), that is freely available (see the website of the ExPASy—SIB Bioinformatics Portal). For multiple alignment analysis ClustalW is preferably used (Thompson et al. (1994) Nucleic Acids Res., 22(22): 4673-4680).

Each amino acid of the query sequence that differs from the reference amino acid sequence at a given position is counted as one difference. An insertion or deletion in the query sequence is also counted as one difference. For example, an insertion of a linker between two ubiquitin moieties is counted as one difference compared to the reference sequence. The sum of differences is then related to the length of the reference sequence to yield a percentage of non-identity. The quantitative percentage of identity is calculated as 100 minus the percentage of non-identity. In specific cases of determining the identity of ubiquitin muteins aligned against unmodified ubiquitin, differences in positions 45, 75 and/or 76 are not counted, in particular, because they are not relevant for the novel binding capability of the ubiquitin mutein to EGFR. The ubiquitin moiety can be modified in amino acid residues 45, 75 and/or 76 without affecting its binding capability; said modifications might, however, be relevant for achieving modifications in the biochemical properties of the mutein. Generally, a ubiquitin used as starting material for the modifications has an amino acid identity of % % at least 94%, at least 95%, of at least 96%, of at least 97%, of at least 98%, or of at least an amino acid sequence identity of 99% to SEQ ID NO: 1, or SEQ ID NO: 2, SEQ ID NO: 3, or to SEQ ID NO: 4. Thus, a polypeptide which is, for example, 95% "identical" to a reference sequence may comprise, for example, five point mutations or four point mutations and one insertion etc, per 100 amino acids, compared to the reference sequence.

The EGFR protein of the invention consists of or comprises a ubiquitin mutein. The ubiquitin mutein of the invention has an amino acid identity of at least 80% of SEQ ID NO: 1. An ubiquitin mutein of the invention exhibits 80% to 93% identity to ubiquitin (SEQ ID NO: 1) or 80% to 93% identity to the di-ubiquitin (SEQ ID NO: 4), most preferred 87-92% identity to SEQ ID NO: 1 or SEQ ID NO: 4. Further preferred amino acid identities are at least 83%, at least 84%, at least 85%, at least 86%, at least 87%, at least 88%, or at least 89%, at least 90%, at least 91%, at least 92%, at least 93%, to SEQ ID NO: 1 or SEQ ID NO: 2. In SEQ ID NO: 3, the amino acid residues 62-66 corresponding to amino acids QKEST of SEQ ID NO: 1 are substituted by placeholders $X_{62}$ to $X_{66}$, which may be exchanged by 1, 2, 3, 4, or 5 arbitrarily chosen amino acids. In preferred embodiments, these amino acids are selected from those specified in the following paragraphs, wherein the "PDI motif" is one particularly preferred combination of amino acids. An ubiquitin mutein of the invention is at least 90%, at least 91%, at least 92%, at least 93%, at least 94%, at least 95%, at least 96%, at least 97%, at least 98% identical to SEQ ID NO: 3 wherein amino acids $X_{62}$ to $X_{66}$ are excluded from the determination of amino acid identity. An ubiquitin mutein of the invention exhibits 90% to 98% identity to ubiquitin of SEQ ID NO: 3. In other words, considering an identity of, for example, 97% to SEQ ID NO: 3, two further amino acids are modified in addition to $X_{62}$ to $X_{66}$, Considering an identity of, for example, 96% to SEQ ID NO: 3, three further amino acids are modified in addition to $X_{62}$ to $X_{66}$, Considering an identity of, for example, 94% to SEQ ID NO: 3, four further amino acids are modified in addition to $X_{62}$ to $X_{66}$, Considering an identity of, for example, 93% to SEQ ID NO: 3, five further amino acids are modified in addition to $X_{62}$ to $X_{66}$, The term "PDI motif" comprises an amino acid residue motif. It refers herein to a specific sequence of amino acid residues. Preferably, the amino acid residue motif consists of three substitutions selected from E64P, E64V, E64A, S65D, S65E, T66I, T66A, T66V, T66M, T66F, T66Y, T66W, or T66L. Preferably, the amino acid motif consists of three substitutions in positions E64P, S65D, and T66I corresponding to unmodified ubiquitin; or E64V, S65D, and T66I; or E64A, S65D, and T66I; or E64V, S65D, and T66V; or E64P, S65D, and T66V; most preferably E64P, S65D, and T66I. Accordingly, the term "PDI motif" comprises or consists of the three amino acid residues PDI, VDI, ADI, PDV, or VDV.

The term "dissociation constant" or "$K_D$" defines the specific binding affinity. A high affinity corresponds to a low value of $K_D$. Thus, the expression "a $K_D$ of at least e.g. $10^{-7}$ M" means a value of $10^{-7}$ M or lower (binding more tightly). $1 \times 10^{-7}$ M corresponds to 100 nM. A value of $10^{-5}$ M and below down to $10^{-12}$ M can be considered as a quantifiable binding affinity. Depending on the application a value of $10^{-7}$ to $10^{-12}$ M is preferred for e.g. chromatographic applications or for e.g. diagnostic or therapeutic applications. In accordance with the invention the affinity of the binding protein for the target binding should be in the range of less than $7 \times 10^{-7}$ M (700 nM). The methods for determining the binding affinities are known per se and can be selected for instance from the following methods known in the art: Surface Plasmon Resonance (SPR) based technology, Biolayer interferometry (BLI), enzyme-linked immunosorbent assay (ELISA), flow cytometry, fluorescence spectroscopy techniques, isothermal titration calorimetry (ITC), analytical ultracentrifugation, radioimmunoassay (RIA or IRMA) and enhanced chemiluminescence (ECL). Some of the methods are described in the Examples below.

EGFR binding protein based on Ubiquitin Mutein (Affilin). The EGFR binding protein according to this invention is comprising a ubiquitin mutein with binding affinity ($K_D$) of less than 700 nM for epidermal growth factor receptor (EGFR) wherein the ubiquitin mutein exhibits 80% to 93% identity to ubiquitin (SEQ ID NO: 1) or 80% to 93% identity to the ubiquitin-dimer of SEQ ID NO: 4 and wherein the amino acid in position 64 is selected from P, V, and A, wherein the amino acid in position 65 is selected from D and E, and wherein the amino acid in position 66 is selected from I, V, A, M, F, Y, W, and L. Preferably, the amino acid sequence in positions 64, 65, and 66 is selected from amino acids P, D, and I, or amino acids V, D, and I, or amino acids A, D, and I, or amino acids V, D, and V, or amino acids P, D, and V. The EGFR binding protein according to this invention comprising a ubiquitin mutein with binding affinity ($K_D$) of less than 700 nM for epidermal growth factor receptor (EGFR) wherein the ubiquitin mutein comprises an amino acid sequence wherein three amino acids selected from amino acids 62-66 corresponding to $X_{62}$, $X_{63}$, $X_{64}$, $X_{65}$, and $X_{66}$ of SEQ ID NO: 3 are substituted compared to the wild-type amino acid sequence QKEST and wherein the ubiquitin mutein has at least 90% sequence identity to SEQ ID NO: 3.

The degree of modification of a ubiquitin mutein according to the invention accounts for minimally 7% and up to a total of about 20% of amino acids compared to unmodified ubiquitin (determination of identity excludes amino acids 45, 75, 76, as explained above). In other words, this corresponds to 5-15 amino acid residues in a ubiquitin moiety which are modified in order to generate a new binding property to a target antigen (if two ubiquitin moieties are linked, 10-30 amino acids in total are modified to generate a new binding property). Most preferred are substitutions of less than 15% of all amino acids of ubiquitin to generate a novel protein with newly created measurable binding properties to a target antigen. In other words, this corresponds to a modification of 6 to 11 amino acid residues to generate a novel protein with newly created measurable binding properties to a target antigen. Considering this, there is a sequence identity to unmodified ubiquitin of SEQ ID NO: 1 or di-ubiquitin of SEQ ID NO: 4 of at least 80%, at least 85%, at least 86%, at least 87%, at least 88%, at least 89%, at least 90%, at least 91%, at least 92%, at least 93%, in particular if substitutions and insertions are generating the novel binding property.

The derivatization of ubiquitin to generate a ubiquitin mutein that specifically binds a particular target antigen has been described in the art. For example, a library of different ubiquitin muteins can be created in which the sequence as shown in SEQ ID NO: 1 or SEQ ID NO: 2 or SEQ ID NO: 3 or SEQ ID NO: 4 has been altered. Preferably, the alteration is carried out at amino acids corresponding to (i) region 2-11 of unmodified ubiquitin, or (ii) region 62-68 of unmodified ubiquitin or (iii) in both regions simultaneously. However, further positions not comprised by these regions might be altered as well. Preferably, the alteration is a substitution, insertion or deletion as described in the art. The substitution of amino acid residues for the generation of the novel binding proteins derived from ubiquitin can be performed with any desired amino acid. This is described in detail in EP1626985B1, EP2379581B1, and EP2721152, which are incorporated herein by reference.

The step of modification of the selected amino acids is performed according to the invention preferably on the genetic level by random mutagenesis of the selected amino acids. Preferably, the modification of ubiquitin is carried out by means of methods of genetic engineering for the alteration of a DNA belonging to the respective protein. One preferred method of modification of the selected amino acids is by random mutagenesis of the multiple, selected amino acids at the genetic level. Methods to introduce such random mutagenesis are well known in the art. Assuming a random distribution of the 20 natural amino acids at e.g. 8 positions generates a pool of 20 to the power of 8 ($20^8$=2.56×$10^{10}$) theoretical ubiquitin muteins, each with a different amino acid composition and potentially different binding properties. This large pool of genes constitutes a library of different Affilin molecules.

Subsequently, the library can be cloned into a phagemid vector (e.g. pCD87SA (Paschke, M. and W. Hohne (2005). "Gene 350(1): 79-88)). The library may be displayed on phage and subjected to repeated rounds of panning against the respective target antigen. Ubiquitin muteins from enriched phage pools are cloned into expression vectors for individual protein expression. Preferably, expression of the ubiquitin mutein is then carried out in prokaryotic or eukaryotic organism to enable screening for specific binding proteins by established techniques, such as ELISA on automated high-throughput screening platforms. Identified clones with desired binding properties are then sequenced to reveal the amino acid sequences of target-binding Affilin molecules. In case of an Affilin with one ubiquitin mutein moiety, the amino acid positions of the Affilin have to be aligned with the sequence given for ubiquitin (for example, SEQ ID NO: 1 or SEQ ID NO: 2 or SEQ ID NO: 3) in order to identify the amino acid changes. In case of an Affilin molecule consisting of two ubiquitin moieties, the amino acid positions of the Affilin have to be aligned with the sequence given for ubiquitin (SEQ ID NO: 4) in order to identify the amino acid changes.

The identified binding protein may be subjected to further maturation steps, e.g. by generating additional libraries based on alterations of the identified sequences and repeated phage display, ribosomal display, panning and screening steps as described above.

The substitution of amino acids for the generation of the novel binding proteins derived from ubiquitin (ubiquitin mutein or Affilin molecules) can be performed with any desired amino acid. This is described in detail for example in EP1626985B1 and EP2379581B1, which are incorporated herein by reference. The identified binding protein may be subjected to further maturation steps, e.g. by generating additional libraries based on alterations of the identified sequences and repeated phage display, ribosomal display, panning and screening steps as described above.

Linker comprised in fusions or conjugates of the EGFR binding proteins of the invention. As described above the binding molecules of the invention can comprise one or two modified ubiquitin subunits and/or can be genetically fused to other functional protein moieties. In the context of such fusion proteins of the invention the term "linker" refers to a single amino acid or a polypeptide that joins at least two other protein molecules covalently.

The linker is genetically fused to the first and second binding proteins or protein moieties to generate a single, linear polypeptide chain. The length and composition of a linker may vary between at least one and up to about 20 amino acids. Preferably, the linker length is between one and 20 amino acids. More preferably, the peptide linker has a length of between 1 and 15 amino acids; e.g. 1, 2, 3, 4, 5, 6, 7, 8, 9, 10, 11, 12, 13, 14, 15 amino acids.

It is preferred that the amino acid sequence of the peptide linker is not immunogenic to human beings, stable against proteases and does not form a secondary structure. An example is a linker comprised of small amino acids such as glycine, serine or alanine. The linkers can be glycine-rich (e.g., more than 50% of the residues in the linker can be glycine residues). Preferred are glycine-serine-linker of variable length consisting of glycine and serine residues only. In general, linkers of the structure $(SGGG)_n$ or permutations of SGGG, e.g. $(GGGS)_n$, can be used wherein n can be any number between 1 and 6, preferably 1 or 2 or 3. Other linkers for the genetic fusion of proteins are known in the art and can be used. In one embodiment of the invention, the first binding protein (e.g. ubiquitin mutein) and the second binding protein (e.g. monoclonal antibody or fragment thereof) are linked via a $(G_3S)_4$ linker. Examples for linkers are shown in SEQ ID NOs: 78-85. Moreover, a non-peptide linker such as polyethylene glycol or an alternative polymer could be used.

In case of chemical conjugates of the binding proteins of the invention, the term "linker" refers to any chemical moiety which connects the EGFR binding protein with other proteinaceous or non-proteinaceous moieties either covalently or non-covalently, e.g., through hydrogen bonds, ionic or van der Waals interactions, such as two complementary nucleic acid molecules attached to two different moieties that hybridize to each other. Such linkers may comprise reactive groups which enable chemical attachment to the protein through amino acid side chains, the N-terminal α-amino or C-terminal carboxy-group of the protein. Such linkers and reactive groups are well-known to those skilled in the art and not described further.

Target antigen: EGFR. The epidermal growth factor receptor (EGFR; synonym names are HER1 or ErbB1) is the cell-surface receptor for members of the epidermal growth factor family (EGF-family) (NCBI reference: NP_005219). EGFR is known for its role in lung cancer, head and neck cancer and colorectal cancer. The term "epidermal growth factor receptor" or "EGFR" comprises all polypeptides which show a sequence identity of at least 70%, 80%, 85%, 90%, 95%, 96% or 97% or more, or 100% to NP_005219 and have the functionality of EGFR. The term "EGFR" comprises related polypeptides, including allelic variants, splice variants, derivative variants, substitution variants, deletion variants, and/or insertion variants including the addition of an N-terminal methionine, fusion polypeptides, and interspecies homologs. For isoforms, see for example, Albitar et al. Molecular Cancer 2010, 9: 166 which is incorporated herein by reference. In particular, the term "EGFR" comprises the class III variant of EGFR (EGFRvIII) (deletion of exons 2-7, deletion of amino acids 5-274, see Wikstrand et al., J NeuroViro 1998, 4: 148-158). The term "EGFR" as understood herein also comprises EGFR class I, class II, class IV, class V, class VI and class VII mutants and variants thereof (see Wikstrand et al., supra). An EGFR polypeptide can include terminal residues, such as tag residues, signal peptide sequence residues, targeting residues, amino terminal methionine residues, lysine residues. Reference to EGFR includes variants, isoforms and species homologs of human EGFR. The term EGFR also comprises naturally occurring mutant forms (see for example Humphrey et al. *PNAS (USA)* 87:4207-4211 (1990)). "EGFR" may be a native sequence EGFR or an amino acid sequence variant thereof. The extracellular part of the mature EGFR consists of 621 amino acids and four receptor domains: Domain I encompasses residues 1-165, domain II residues 166-312, domain III residues 313-481 and domain IV 482-621 (see for example Cochran et al. (2004) *J. Immunol. Methods*, 287, 147-158).

The involvement in many cancers validates EGFR as a useful therapeutic target and supports the search for improved understanding of receptor biology and the development of improved therapies. Potential causes of the modest efficacy of current EGFR antagonists include the inability to effectively compete with ligand, especially in the presence of autocrine signaling; insufficient down-regulation of receptor; lack of inhibition of constitutively active EGFRvIII; and mutational escape. Thus, novel binders capable of downregulation and/or inhibition via different modes of action would be beneficial and multivalent and/or multispecific binders against EGFR hold the potential to be more effective in this respect.

Description of the EGFR Binding proteins of the invention. Many examples of EGFR binding proteins with specific 3-amino-acid sequence motif at positions 64, 65, and 66 are provided in this invention (see, for example, SEQ ID NOs: 8-73 and 113-114). The EGFR binding Affilin molecules of the invention bind to the isolated extracellular domain of EGFR with measurable binding affinity of less than 700 nM, compared to non-modified ubiquitin that does not naturally bind to EGFR with any measurable binding affinity. Preferred EGFR binding molecules include ubiquitin mutein with 80% to 93% identity to ubiquitin (SEQ ID NO: 1) or 80% to 93% identity to the ubiquitin-dimer of SEQ ID NO: 4 and wherein the amino acid in position 64 is selected from P, V, and A, wherein the amino acid in position 65 is selected from D and E, and wherein the amino acid in position 66 is selected from I, V, A, M, F, Y, W, and L. Ubiquitin muteins with substitutions of at least 5 amino acids at the C-terminal part of the moiety within region 62-68 wherein 3 amino acids of these amino acids preferably show a specific "PDI motif". Preferably, the amino acid sequence in positions 64, 65, and 66 is selected from PDI, VDI, ADI, PDV, or VDV (e.g. see FIG. 1). Specific examples for EGFR binding proteins Affilin 139820 (binding cartridge (PWYGYD)TTVDI and one further exchange I23T; SEQ ID NO: 113) with amino acid residues V, D, and I, Affilin 139754 with amino acid residues A, D, and I, Affilin 139791 with amino acid residues V, D, and V, and Affilin 144747 (binding cartridge (DDKGYD)QNPDV and one further exchange K6N; SEQ ID NO: 114) with amino acid residues P, D, and V. The EGFR binding protein comprises an ubiquitin mutein with further amino acid modifications comprising further substitutions and optionally an insertion of 2-10 amino acids. In one embodiment of the invention, in order to generate a measurable binding affinity to EGFR, a ubiquitin is at least substituted in 5 amino acids corresponding to positions 62, 63, 64, 65, 66 of SEQ ID NO: 1 in combination with an insertion of 2-10 amino acids in the loop region corresponding to positions 8-11 of SEQ ID NO: 1. In some embodiments, the ubiquitin mutein comprises an insertion of amino acids within a natural loop region, preferably within the first loop of the N-terminal part, in addition to the substitutions in positions 64, 65, 66 and possible further modifications. A preferred EGFR binding protein based on ubiquitin has substitutions in amino acid region 62-66 of SEQ ID NO: 1 or SEQ ID NO: 2 combined with an insertion of 2-10 amino acids, preferably 4-8 amino acids, even more preferred 6 amino acids, in a natural loop region of said ubiquitin muteins, preferably in region 8-11, more between position 9 and 10 corresponding to SEQ ID NO: 1. The insertion of 2-10 amino acids length is preferably between positions 9-10 of SEQ ID NO: 1. Examples are given in SEQ ID NOs: 8-52. These sequences show 80% to 93% identity to ubiquitin (SEQ ID NO: 1), preferably between 89-92% identity to SEQ ID NO: 1. In particular, SEQ ID NOs 9-24, 26-28, 30-32, 35-50, and 52 show 92% identity to SEQ ID NO: 1, SEQ ID Nos 25, 29, 34, 51, and 53 exhibit 91% identity to SEQ ID NO: 1, and SEQ ID NO. 33 exhibits 89% identity to SEQ ID NO: 1 (note that the insertion is counted as 1 difference and that modifications in positions 45, 75, 76 are not considered according to the definitions above).

In another embodiment of the invention, two ubiquitin moieties are a least substituted in 5 amino acids selected from and corresponding to regions 2-11 and 62-66, in particular positions 62, 63, 64, 65, 66 of SEQ ID NO: 1 and in positions 6 and 8, and the two ubiquitin moieties are connected directly or via a peptide linker. Examples are given in SEQ ID NOs: 53-73. These sequences show 80% to 93% identity to the ubiquitin-dimer of SEQ ID NO: 4, preferably between 87% and 91% identity to SEQ ID NO: 4. Each ubiquitin moiety of the binding protein shows 80% to 93% identity to SEQ ID NO: 1.

Amino acid residue motif "PDI". The invention provides an EGFR binding protein comprising a ubiquitin mutein with binding affinity ($K_D$) of less than 700 nM for the extracellular domain of the epidermal growth factor receptor (EGFR) wherein the ubiquitin mutein comprises an amino acid sequence wherein three amino acids selected from amino acids 62 to 66 of ubiquitin (corresponding to $X_{62}$, $X_{63}$, $X_{64}$, $X_{65}$, and $X_{66}$ of SEQ ID NO: 3) are substituted compared to the amino acid sequence QKEST and wherein the ubiquitin mutein has 80% to 93% sequence identity to ubiquitin (SEQ ID NO: 1) or to di-ubiquitin (SEQ ID NO: 4) or at least 90% sequence identity to SEQ ID NO: 3. Herein, positions 62 and 63 of ubiquitin ($X_{62}$ and $X_{63}$) may be substituted by any amino acid, position 64 of ubiquitin ($X_{64}$) is substituted by an amino acid selected from P, V, and A, position 65 of ubiquitin ($X_{65}$) is substituted by an amino acid selected from D and E, and position 66 of ubiquitin ($X_{66}$) is substituted by an amino acid selected from I, V, A, M, F, Y, W, and L. Preferably, the amino acids in positions 64, 65, and 66 of ubiquitin ($X_{64}$, $X_{65}$, and $X_{66}$) are substituted by amino acids selected from amino acids P, D, and I, or V, D, and I, or A, D, and I, or V, D, and V, or P, D, and V.

Thus, the EGFR binding ubiquitin mutein (Affilin) of the invention comprises a characteristic motif, comprising an amino acid sequence selected from positions 62-66 of SEQ ID NO: 1, i.e. from positions $X_{62}$, $X_{63}$, $X_{64}$, $X_{65}$, and $X_{66}$ of SEQ ID NO: 3, which are substituted compared to the wild type sequence QKEST.

In particular, the invention provides a polypeptide binding to EGFR with a characteristic amino acid residue motif in amino acid positions $X_{64}$, $X_{65}$, and $X_{66}$ of SEQ ID NO: 3 (corresponding to positions 64, 65, 66 of SEQ ID NO: 1, unmodified ubiquitin) wherein the amino acid motif is either proline, aspartic acid, and isoleucine (PDI), or valine, aspartic acid, and valine (VDV), or valine, aspartic acid, and isoleucine (VDI), or proline, aspartic acid, and valine (PDV), or valine, aspartic acid, and isoleucine (ADI) (all are referred to herein as "PDI motif"). The characteristic PDI motif is found in EGFR binding proteins of the invention. In binding proteins comprising two ubiquitin moieties, the motif is found preferably in the first moiety.

Some embodiments of the invention provide substitutions in position 62 of ubiquitin ($X_{62}$ and $X_{63}$) selected from R, Q, H, K, G, S, T, N, V, I, and W; in position 63 of ubiquitin ($X_{63}$) selected from N, H, A, S, R, E, T, Q, and K; in position 64 of ubiquitin ($X_{64}$) a small, unpolar amino acid selected from P, V, and A; in position 65 of ubiquitin ($X_{65}$) an acidic amino acid selected from D and E; and in position 66 of ubiquitin ($X_{66}$) is selected from I, V, A, M, F, Y, W, and L. Preferred embodiments of the invention provide substitutions in position 62 of ubiquitin ($X_{62}$) selected from R, Q, G, S, and T; in position 63 of ubiquitin ($X_{63}$) selected from N, H, and A; in position 64 of ubiquitin ($X_{64}$) selected from P, V, and A; in position 65 of ubiquitin ($X_{65}$) selected from D; $X_{66}$ is selected from I and V.

In one embodiment of the invention, the EGFR binding protein comprises an amino acid residue motif consisting of three amino acids substitutions selected from E64P, E64V, E64A, S65D, S65E, T66I, T66A, T66V, T66M, T66F, T66Y, T66W, or T66L.

Some embodiments of the invention provide a five-amino acid motif in positions 62-66 of ubiquitin ($X_{62}$, $X_{63}$, $X_{64}$, $X_{65}$, and $X_{66}$) consisting of amino acid residues RNPDI, QNPDI, RHPDI, QHPDI, QAPDI, QQPDI, GEPDI, GHPDI, IHADI, HHPDI, RRVDV, SAPDI, SHPDI, THPDI, TSPDI, VNPDI, QSPDI, as shown in SEQ ID NO: 90-106 and in SEQ ID NO: 111-112 and in FIG. 1, particularly preferred are $RX_{63}$PDI or $QX_{63}$PDI, most preferably RNPDI, RHPDI, QNPDI, and QHPDI.

In one embodiment of the invention, the EGFR binding protein comprises a ubiquitin mutein with binding affinity ($K_D$) of less than 700 nM for the extracellular domain of the epidermal growth factor receptor (EGFR) wherein the ubiquitin mutein comprises an amino acid residue motif at positions 64, 65, and 66 corresponding to SEQ ID NO: 1, and wherein the ubiquitin mutein has at least 80% to 94% sequence identity to SEQ ID NO: 1. In one embodiment of the invention, the EGFR binding protein comprises a ubiquitin mutein with binding affinity for EGFR with an $K_D$ value of at most 700 nM wherein the amino acids corresponding to positions 62 and 63 of SEQ ID NO: 1 may be any amino acid sequence; the amino acid corresponding to position 64 of SEQ ID NO: 1 is selected from proline, valine, and alanine (P, V, and A), most preferably proline (β); the amino acid corresponding to position 65 of SEQ ID NO: 1 is selected from an acidic amino acid, preferably aspartic acid and glutamic acid (D and E), most preferably aspartic acid (D); and the amino acid corresponding to position 66 of SEQ ID NO: 1 is selected from isoleucine, valine, alanine, methionine, phenylalanine, tyrosine, tryptophan, and leucine (I, V, A, M, F, Y, W, and L), most preferably isoleucine (I). In particular, the invention provides a ubiquitin mutein binding to EGFR wherein the amino acid residue motif is either proline, aspartic acid, and isoleucine (PDI), or proline, aspartic acid, and valine (PDV), or alanine, aspartic acid, and isoleucine (ADI), or valine, aspartic acid, and valine (VDV), or valine, aspartic acid, and isoleucine (VDI). In another preferred embodiment of the invention, the EGFR binding protein comprises a ubiquitin mutein wherein the amino acids substitutions comprising an amino acid residue motif are consisting of E64P, S65D, and T66I; or E64P, S65D, and T66V; or E64A, S65D, and T66I; or E64V, S65D, and T66V; or E64V, S65D, and T66I; most preferably E64P, S65D, and T66I.

Preferred substitutions of the amino acid residue motif in the EGFR binding ubiquitin mutein are:

position 64 substituted to an amino acid selected from P, A, V, position 65 substituted to an acidic amino acid selected from D or E, and position 66 substituted to an amino acid selected from I, M, F, Y, W, A, V, L.

FIG. 1 shows a number of modifications of ubiquitin derived EGFR binding proteins. The column "cartridge" denotes the amino acid substitutions. In FIG. 1, in particular in SEQ ID NOs: 8-52, the cartridge of modifications refers to an insertion of 6 amino acids in the first N-terminal loop region of SEQ ID NO: 1 (insertion of amino acids between positions 9-10), shown for example as "(YNPMRY)". The following 5 amino acids in the cartridge refer to substitutions in amino acid positions $X_{62}$, $X_{63}$, $X_{64}$, $X_{65}$, and $X_{66}$ corresponding to SEQ ID NO: 3 or to substitutions in amino acid positions 62-66 of SEQ ID NO: 1 or SEQ ID NO: 4. For example, for Affilin 139819 (SEQ ID NO: 39) the cartridge is (YNPMRY)RNPDI, meaning that naturally occurring N-terminal loop region is extended by an insertion of 6 amino acids (YNPMRY) and further that there are substitutions of 5 amino acids RNPDI at positions 62, 63, 64, 65, 66 of ubiquitin (SEQ ID NO: 1. Affilin 139819 has a characteristic PDI motif at positions 64, 65, and 66. Affilin 139819 binds to the extracellular domain of EGFR with about 20 nM ($2\times10^{-8}$ M) affinity. For Affilin 139791 (SEQ ID NO: 49), the cartridge is (PWRGYD)RRVDV, meaning that there is an insertion of 6 amino acids in the N-terminal loop region and substitutions of 5 amino acids at positions 62, 63, 64, 65, 66 of ubiquitin.

Further modifications in the Affilin are possible, see column "additional exchanges" in FIG. 1. One, two, three, four or more further substitutions can be found in the ubiquitin muteins, in addition to the N-terminal insertion of 6 amino acids and modifications in positions 62, 63, 64, 65, 66 or in addition to the substitution of amino acids 6, 8, and 62, 63, 64, 65, 66 of the first moiety in an Affilin.

For example, Affilin 142232 (SEQ ID NO: 29) has one further substitutions in position 38, Affilin 139817 (SEQ ID NO: 25) has one further substitutions in position 38, Affilin 139829 (SEQ ID NO: 34) has one further substitutions in positions 12, Affilin 139826 (SEQ ID NO: 51) has one further substitution in position 74, Affilin 139808 (SEQ ID NO: 33) has two further substitutions in positions 5 and 12, Affilin 139923 (SEQ ID NO: 70) has four further substitutions in the first moiety in positions 4, 5, 13, and 17, and one further substitution in the second moiety in position 70. Thus, further modifications are preferably found at least in positions 4, 5, 12, 13, 17, 38, 70, and 74 of ubiquitin. Examples are provided in FIG. 1.

In another embodiment of the invention, the cartridge of modifications refers to a ubiquitin mutein molecule with modifications in a first ubiquitin moiety at amino acid positions 6, 8, and 62, 63, 64, 65, 66 of ubiquitin (SEQ ID NO: 1) ($X_{62}$, $X_{63}$, $X_{64}$, $X_{65}$, and $X_{66}$ corresponding to SEQ ID NO: 3) and modifications in a second ubiquitin moiety at positions 6, 8 and 62, 63, 64, 65, 66 of ubiquitin (SEQ ID NO: 1) ($X_{62}$, $X_{63}$, $X_{64}$, $X_{65}$, and $X_{66}$ corresponding to SEQ ID NO: 3), wherein the moieties are linked directly or by a peptide linker of preferably 3-15 amino acids. Alternatively, as starting sequence, SEQ ID NO: 4 could be used for modifications. SEQ ID NO: 4 is a molecule with two unmodified ubiquitin moieties, shown in SEQ ID NO: 4 without linker. However, in some embodiments, a peptide linker of preferably 3-15 amino acids between the two ubiquitin moieties might be inserted between amino acid 76 of the first moiety and amino acid 1 of the second moiety to connect the two ubiquitin moieties. In FIG. 1, in particular in SEQ ID NOs: 53-73 and SEQ ID NOs: 76 and 77, the cartridge refers to modifications in amino acids 6, 8, 62-66 in the first and in the second ubiquitin moiety of the molecule. For example, for clone 139864 (SEQ ID NO: 58) the cartridge reads HPRNPDI-HMGAG™, meaning that there are substitutions in the first ubiquitin moiety as follows: 6H, 8P, 62R, 63N, 64P, 65D, 661, and in the second ubiquitin moiety as follows: 6H, 8M, 62G, 63A, 64G, 65T, and 66M (see FIG. 1). The EGFR specific binding motif PDI is located in the N-terminal ubiquitin moiety of the linear molecule.

Thus, the EGFR binding ubiquitin muteins of the invention comprise amino acid sequences selected from the group consisting of SEQ ID NOs: 8-73 and 113-114 or an amino acid sequence that exhibits at least 80% sequence identity to one or more of the amino acid sequences of SEQ ID NO: 8-73 and 113-114, and as shown in FIG. 1. In particular, EGFR binding ubiquitin muteins comprise proteins with SEQ ID NO: 89-106 and 111-112, and ubiquitin muteins with 80% sequence identity to amino acids in positions 62, 63, 64, 65, 66 of SEQ ID NO: 89-106 and 111-112.

In one embodiment of the invention, a ubiquitin moiety is at least substituted at 5 amino acids selected from and corresponding to amino acids in positions 62, 63, 64, 65, 66 wherein the substitutions in positions 64, 65, 66 comprise the PDI motif. It is preferred that additionally to these substitutions, the ubiquitin molecule have optionally an insertion of 2-10 amino acids, preferably 4-8 amino acids, even more preferred 6 amino acids, in a region corresponding to positions 8-11 of SEQ ID NO: 1. Examples are given in SEQ ID NO: 8-52, as shown in FIG. 1. Thus, in some embodiments, the ubiquitin moiety comprises an insertion of amino acids within the first loop at the N-terminal part in addition to the PDI motif in amino acid positions 64, 65, and 66 and possible further modifications. In some embodiments, the EGFR binding Affilin comprises two differently modified ubiquitin moieties derived from SEQ ID NO: 1 or SEQ ID NO: 2 or SEQ ID NO: 3 directly connected or linked to each other and together represent the binding entity that jointly bind one epitope. A di-ubiquitin is shown in SEQ ID NO: 4.

In an embodiment of the invention, two ubiquitin moieties are a least substituted at 5 amino acids selected from and corresponding to regions 2-11 and positions 6, 8, 62, 63, 64, 65, 66 of SEQ ID NO: 1, provided that the N-terminal moiety comprises the PDI motif in positions 64, 65, and 66. The two ubiquitin muteins are connected directly or via a linker, preferably a peptide linker. Both ubiquitin muteins of this embodiment bind to the same or an overlapping epitope of EGFR. Examples are shown in SEQ ID NO: 53-73.

Biochemical characterization. The further characterization of EGFR binding ubiquitin muteins can be performed in the form of soluble proteins. The appropriate methods are known to those skilled in the art or described in the literature. The affinity and specificity of the variants isolated can be detected by means of biochemical standard methods as known to those skilled in the art and as discussed above and in the Examples. For stability analysis, for example spectroscopic or fluorescence-based methods in connection with chemical or physical unfolding are known to those skilled in the art. Exemplary methods for characterization of EGFR binding proteins are discussed above and outlined in the Examples section of this invention.

For example, the biochemical target binding analysis is summarized in FIG. 1. Binding affinity was confirmed by different methods known to those skilled in the art, for example by SPR analysis (Biacore). In addition, temperature stability was determined by differential scanning fluorimetry (DSF), as described in further detail in the Examples and as shown in FIG. 1. In addition to results shown in FIG. 1, solubility (no aggregation) was confirmed for all EGFR binding molecules by size exclusion chromatography. Further functional characterization was performed using cell EGFR binding analysis (flow cytometry) with EGFR overexpressing cells. Different concentrations of the Affilin molecules were tested (e.g. 500, 50, and 5 nM). EGFR cell target binding was confirmed, as shown in FIG. 2 and FIG. 3. Competitive binding experiments comparing Affilin molecules show that the epitope that is bound by different Affilin EGFR binding proteins with PDI motif is identical or at least overlapping (see FIG. 4). FIG. 5 surprisingly shows that an EGFR binding Affilin molecule with PDI motif does not compete with Cetuximab and thus covers a non-overlapping epitope. Thus, Affilin binding molecules with PDI motif bind to a different epitope on EGFR than Cetuximab. Furthermore, Affilin binding proteins with PDI motif surprisingly show binding to EGFR on xenograft tumor tissue from human cancer cells. Further, cellular binding of different Affilin molecules with PDI motif was confirmed on tumor cells of human origin (see FIG. 7). In particular and surprisingly, Affilin molecules with PDI motif show strong binding to EGFR.

Homo-dimers and Hetero-dimers. In further embodiments, the EGFR binding protein of the invention comprises at least two ubiquitin muteins (Affilin proteins) of the same or a different target specificity and/or binding to the same or a different epitope of EGFR. Examples are shown in FIGS. 9-12.

In one embodiment of the invention, EGFR binding proteins comprising two identical ubiquitin muteins of the same target specificity (homo-dimer) and binding to the same epitope of EGFR show superior binding properties. Constructs of dimeric EGFR Affilin molecules can be obtained by gene synthesis or lab scale cloning, as known to those skilled in the art. For example, two identical anti-EGFR-Affilin molecules, i.e. Affilin 139819 (SEQ ID NO: 39), were subjected to homo-dimerization, preferably with a peptide linker. The binding affinity of the homo-dimer to EGFR was about 0.6 nM (Biacore, FIG. 11) and about 1.5 nM to cells (FACS/CHO-K1-EGFR cells and A549 cells, FIG. 12) which is a significant higher affinity than the binding affinity of Affilin 139819 (FIG. 9). Further, the target binding of Affilin 139819 and homo-dimeric EGFR Affilin (139819-139819) was compared. Neither Affilin competes with EGF for EGFR binding. Accordingly, the PDI motif containing Affilin molecules use different or non-overlapping epitopes on the EGF receptor than the natural target EGF.

In another embodiment of the invention, EGFR binding proteins are comprising two different ubiquitin muteins of the same target specificity. It is preferred that two different anti-EGFR Affilin proteins are linked directly or via linkers, preferably peptide linkers. The biochemical characterization for the hetero-dimeric Affilin comprising Affilin 139791 and Affilin 139819 is summarized in Table 2 (see Examples).

Bispecific and/or bivalent binding proteins comprising EGFR-Affilin and monoclonal antibodies. The binding protein of the invention may also comprise a second binding protein which comprises or consists of a monoclonal antibody or fragment thereof or a second Affilin molecule. In one embodiment, the second binding protein is an antibody with specificity for EGFR.

The function of EGFR can be inhibited by specific monoclonal EGFR antibodies that block the binding of ligands to the extracellular part of the receptor. For example, the monoclonal EGFR antibody Cetuximab (heavy chain: SEQ ID NO: 5, light chain: SEQ ID NO: 6; Tradename Erbitux®) is known from the prior art to inhibit the function of EGFR. Cetuximab is used for the treatment of metastatic colorectal cancer, head, and neck cancer. The antibody is frequently combined with chemotherapeutics and/or radionuclide approaches to increase the therapeutic efficacy. Another EGFR specific human monoclonal antibody is for example Panitumumab (tradename Vectibix®). Panitumumab binds with high affinity to EGFR and is used particularly for the treatment of metastatic colorectal cancer.

It was surprisingly found that a bispecific binding molecule having a novel format consisting of an anti-EGFR monoclonal antibody and an anti-EGFR-specific Affilin with PDI motif is able to bind with high specificities to EGFR.

This is exemplified in the Figures and Examples. In addition, such constructs can be easily expressed in conventional expression systems.

One embodiment of the invention shows that fusion proteins of anti-EGFR Affilin molecules with Cetuximab show stronger binding to EGFR than Cetuximab alone, for example, if the anti-EGFR Affilin is fused to the C-terminus of the light chain of Cetuximab (see FIG. 8A), for example SEQ ID NO: 87 (CL139819). It was found that a bispecific binding molecule having a novel format consisting of an anti-EGFR monoclonal antibody and an anti-EGFR-specific Affilin is able to bind with high specificity to EGFR.

Binding affinity was tested via Biacore, as described in further detail in the Examples and in FIG. 8, which shows the characterization of fusion proteins with anti-EGFR-Affilin fused to light chains of Cetuximab. FIG. 8A demonstrates significantly higher binding level of the fusion protein with anti-EGFR-Affilin (CL-Affilin-139819) compared to Cetuximab. The EGFR binding of the control fusion protein with unmodified ubiquitin fused to the C-terminus of Cetuximab (CL-ubiquitin) is comparable to Cetuximab. Comparable results were obtained with fusion proteins having C-terminal fusion to heavy chains. Thus, fusion of anti-EGFR Affilin to Cetuximab enhance the binding level of the fusion protein to EGFR compared to Cetuximab.

FIG. 8B demonstrates higher binding level of NL-Affilin-139819 compared to NL-ubiquitin. Comparable results were obtained with fusion proteins having N-terminal fusion to heavy chains.

Fusion proteins of the invention may further comprise complex fusion proteins of EGFR binding Affilin proteins and Cetuximab, for example NH139791-NL139864; CH139864-NL139864; NH139864-CH139864; CH139864-CL139864. The complex fusion protein with anti-EGFR-Affilin proteins fused Cetuximab enhance the binding level of the fusion protein to EGFR compared to Cetuximab, in particular Affilin fusions to the C-terminus of the light chain and to the N-terminus of the heavy chain of the monoclonal antibody.

Binding proteins and conjugates of the invention comprising further functional moieties. One embodiment of the invention covers an EGFR binding protein of the invention comprising the ubiquitin mutein and further at least one additional protein or molecule. The additional protein can be a ubiquitin mutein (Affilin) with identical or different specificity for an antigen as the first binding protein. In a further embodiment, the binding protein of the invention comprises a third binding protein wherein the third binding protein is a ubiquitin mutein with specific binding affinity of less than 700 nM to the same or a different epitope than the first protein and wherein the ubiquitin muteins have a sequence identity of at least 80% to the amino acid sequence defined by SEQ ID NO: 1, and wherein the third binding protein is linked to different termini of the second binding protein (monoclonal antibody) than the first binding protein or to the N- or C-terminus of the first binding protein.

One embodiment of the invention covers a fusion protein or a conjugate comprising an Affilin-antibody fusion protein or conjugate further fused with or conjugated to a moiety preferably selected from at least one member of the groups (i), (ii) and (iii) consisting of (i) a pharmacokinetic moiety modulating serum half-life selected from a polyethylene glycol, a human serum albumin, anti-human serum albumin, albumin-binding peptides, a polymer sequence forming a random coil, an immunoglobulin or immunoglobulin fragments, or a polysaccharide, and, (ii) a therapeutically active component, optionally selected from a monoclonal antibody or a fragment thereof with the binding specificity of said monoclonal antibody, cytokine, a chemokine, a cytotoxic compound, an enzyme, or derivatives thereof, or a radionuclide, and (iii) a diagnostic component, optionally selected from a fluorescent compound, a photosensitizer, or a radionuclide.

The conjugate molecule can be attached e.g. at one or several sites through a peptide linker sequence or a carrier molecule. For example, a fusion protein of the invention could be coupled to a carrier suitable for further multitoxophore conjugation. The carrier can be selected from polyethylene glycol (PEG) or hydroxyethyl starch (HES) or other suitable carriers.

Further conjugation with proteinaceous or non-proteinaceous moieties to generate proteins conjugates according to the invention can be performed applying chemical methods well-known in the art. In particular, coupling chemistry specific for derivatization of cysteine or lysine residues is applicable. In case of introduction of non-natural amino acids further routes of chemical synthesis are possible, e.g. "click chemistry" or aldehyde specific chemistry and others.

Conjugates thus obtained can be selected from one or more of the following examples: conjugation of the protein via lysine residues; conjugation of the protein via cysteine residues via maleimide chemistry; in particular, cysteine residues can be specifically introduced and can be located at any position suitable for conjugation of further moieties peptidic or proteinogenic conjugations—genetic fusions (preferred C- or N-terminal) "Tag" fusions—a protein or a peptide located either at the C- or N-terminus of the protein. Fusion "tags" are, e.g., poly-histidine, HA-tag, FLAG-tag, Strep-tag, and others. These and other methods for covalently and non-covalently attaching a protein of interest to other functional components are well known in the art, and are thus not described in further detail here. A further embodiment relates to binding proteins according to the invention, further comprising a pharmacokinetic moiety modulating serum half-life or biodistribution, preferably selected from polyethylene glycol (PEG), a human serum albumin, anti-human serum albumin, albumin-binding peptides, a polymer sequence forming a random coil, or an immunoglobulin or immunoglobulin fragments, for example an Fc fragment. Several techniques for producing proteins with extended half-life are known in the art.

The invention therefore covers fusion proteins comprising an EGFR binding protein wherein the EGFR binding protein is genetically fused with another protein and optionally further to non-proteinaceous moieties, or a conjugate wherein the EGFR binding protein is chemically linked to another protein and optionally further to non-proteinaceous moieties.

Methods of identification of Affilin molecules (mutagenesis). By way of example, starting point for the mutagenesis can be for example the cDNA or genomic DNA of ubiquitin according to SEQ ID NOs: 1-4. Furthermore, the gene coding for the ubiquitin protein can also be prepared synthetically. The DNA of ubiquitin according to SEQ ID NOs: 1-4, can be prepared, altered, and amplified by methods known to those skilled in the art. Different procedures known perse are available for mutagenesis, such as methods for site-specific mutagenesis, methods for random mutagenesis, mutagenesis using PCR or similar methods. All methods are known to those skilled in the art. In a preferred embodiment of the invention the amino acid positions to be mutagenized are predetermined. In each case, a library of different mutants is generally established which is screened using methods known per se. Generally, a pre-selection of the amino acids to be modified can be performed based on structural information available for the ubiquitin protein to be modified. The selection of different sets of amino acids to be randomized leads to different libraries.

Selection of Affilin molecules. The gene pool libraries obtained as described above can be combined with appropriate functional genetic elements which enable expression of proteins for selection methods such as display methods. The expressed proteins are contacted according to the invention with a target molecule to enable binding of the partners to each other if a binding affinity does exist. This process enables identification of those ubiquitin muteins which have a binding activity to the target molecule. See, for example, WO 2011/073214, WO 2011/073208, and WO 2011/073209 for more details of the selection method. The contents of WO 2011/073214, WO 2011/073208, and WO 2011/073209 are herewith incorporated by reference.

Contacting according to the invention is preferably performed by means of a suitable presentation and selection method such as the phage display, ribosomal display, mRNA display or cell surface display, yeast surface display or bacterial surface display methods, preferably by means of the phage display method. For complete disclosure, reference is made also to the following references: Hoess, Curr. Opin. Struct. Biol. 3 (1993), 572-579; Wells and Lowmann, Curr. Opin. Struct. Biol. 2 (1992), 597-604; Kay et al., Phage Display of Peptides and Proteins-A Laboratory Manual (1996), Academic Press. The methods mentioned above are known to those skilled in the art and can be used according to the invention including modifications thereof.

The determination whether the modified protein has a quantifiable binding affinity with respect to a predetermined binding partner can be performed according to the invention preferably by one or more of the following methods: ELISA, plasmon surface resonance spectroscopy, fluorescence spectroscopic methods, flow cytometry, isothermal titration calorimetry, analytical ultracentrifugation, or others.

Methods of production. EGFR binding molecules of the invention may be prepared by any of the many conventional and well known techniques such as plain organic synthetic strategies, solid phase-assisted synthesis techniques or by commercially available automated synthesizers. On the other hand, they may also be prepared by conventional recombinant techniques alone or in combination with conventional synthetic techniques. Conjugates according to the present invention may be obtained by combining compounds by chemical methods, e.g. lysine or cysteine-based chemistry, as described herein above.

According to another aspect of the invention, an isolated polynucleotide encoding a binding protein of the invention is provided. The invention also encompasses polypeptides encoded by the polynucleotides of the invention. The invention further provides an expression vector comprising the isolated polynucleotide of the invention, and a host cell comprising the isolated polynucleotide or the expression vector of the invention.

For example, one or more polynucleotides which encode for an EGFR binding protein of the invention may be expressed in a suitable host and the produced binding protein can be isolated. Vectors comprising said polynucleotides are covered by the invention. In a further embodiment the invention relates to a vector comprising the nucleic acid molecule of the invention. A vector means any molecule or entity (e.g., nucleic acid, plasmid, bacteriophage or virus) that can be used to transfer protein coding information into a host cell.

The present invention furthermore relates to an isolated cell comprising the nucleic acid molecule of the invention or the vector of the invention. Suitable host cells include prokaryotes or eukaryotes. Various mammalian or insect cell culture systems can also be employed to express recombinant proteins.

The invention also relates in an embodiment to a host cell or a non-human host carrying the vector of the invention. A host cell is a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present. In accordance with the present invention, the host may be a transgenic non-human animal transfected with and/or expressing the proteins of the present invention. In a preferred embodiment, the transgenic animal is a non-human mammal.

In another aspect is provided a method of producing an EGFR binding protein of the invention, comprising the steps of a) culturing the host cell of the invention under conditions suitable for the expression of the binding protein and b) isolating the produced binding protein. The invention also encompasses a binding protein produced by the method of the invention. Suitable conditions for culturing a prokaryotic or eukaryotic host are well known to the person skilled in the art.

One embodiment of the present invention is directed to a method for the preparation of an EGFR binding protein according to the invention as detailed above, said method comprising the following steps:preparing a nucleic acid encoding a fusion protein as defined above; introducing said nucleic acid into an expression vector; introducing said expression vector into a host cell; cultivating the host cell; subjecting the host cell to culturing conditions under which a fusion protein is expressed, thereby producing a fusion protein as described above; optionally isolating the protein produced in step (e); optionally conjugating the protein with further functional moieties as described above. Cultivation of cells and protein expression for the purpose of protein production can be performed at any scale, starting from small volume shaker flasks to large fermenters, applying technologies well-known to any skilled in the art.

Following the expression of the ubiquitin protein modified according to the invention, it can be further purified and enriched by methods known perse. The selected methods depend on several factors known perse to those skilled in the art, for example the expression vector used, the host organism, the intended field of use, the size of the protein and other factors.

In general, isolation of purified protein from the cultivation mixture can be performed applying conventional methods and technologies well known in the art, such as centrifugation, precipitation, flocculation, different embodiments of chromatography, filtration, dialysis, concentration and combinations thereof, and others.

For simplified purification the protein modified according to the invention can be fused to other peptide sequences having an increased affinity to separation materials. Preferably, such fusions are selected that do not have a detrimental effect on the functionality of the ubiquitin mutein or can be separated after the purification due to the introduction of specific protease cleavage sites. Such methods are also known to those skilled in the art.

Methods of isolation of the polypeptide produced are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation. see, for example, in Sambrook J, Russell D W, (2001), Molecular Cloning: A laboratory manual. 3rd ed, Cold Spring Harbor Laboratory Press, New York Methods for characterization of the binding proteins. The further characterization of binding proteins of the invention can be performed in the form of the isolated, soluble proteins. The appropriate methods are known to those skilled in the art or described in the literature. Such methods include the determination of physical, biophysical and functional characteristics of the proteins. The affinity and specificity of the variants isolated can be detected by means of biochemical standard methods such as SPR analysis or ELISA as known to those skilled in the art and as discussed above and in the Examples. For stability analysis, for example spectroscopic or fluorescence-based methods in connection with chemical or physical unfolding are known to those skilled in the art, including e.g. differential scanning fluorimetry (DSF). Functional characterization can be performed in appropriate cell-based assays or in vivo experiments. Exemplary methods for characterization of binding proteins are discussed above and outlined in the Examples section of this invention.

Uses of the EGFR binding proteins of the invention. In a further aspect of the invention, an EGFR binding ubiquitin mutein or fusion protein or conjugate is used in medicine, in particular in a method of medical treatment or diagnosis, preferably in cancer.

The membrane protein EGFR is known to be upregulated in tumor cells, resulting in uncontrolled growth of tumor cells and in the formation of metastases. New therapies for cancer patients include an inhibition of EGFR by targeted therapeutics such as for example the monoclonal antibodies Cetuximab or Panitumumab.

The pharmaceutical composition comprising the EGFR binding ubiquitin mutein of the invention, can be used for treatment of cancer in which EGFR is relevant for the development of the disease including but not limited to colorectal, breast, lung, head and neck, ovarian, cervical, prostate, pancreatic cancer.

The compositions are adapted to contain a therapeutically or diagnostically effective dose of the EGFR binding ubiquitin mutein of the invention. The amount of protein to be administered depends on the organism to be treated, the type of disease, the age and weight of the patient and further factors known per se.

The invention covers a pharmaceutical composition containing the EGFR binding ubiquitin mutein or conjugate or a combination or the nucleic acid molecule of the invention, the vector of the invention, and/or the host cell or non-human host thereof and a pharmaceutically acceptable carrier. The invention further covers a diagnostic agent comprising the EGFR binding ubiquitin mutein or conjugate or the nucleic acid molecule of the invention, the vector of the invention, and/or the host cell or non-human host with a diagnostically acceptable carrier. The compositions contain a pharmaceutically or diagnostically acceptable carrier and optionally can contain further auxiliary agents and excipients known per se. These include for example but are not limited to stabilizing agents, surface-active agents, salts, buffers, coloring agents etc.

The pharmaceutical composition comprising the EGFR binding ubiquitin mutein can be in the form of a liquid preparation, a lyophilisate, a cream, a lotion for topical application, an aerosol, in the form of powders, granules, tablets, suppositories, or capsules, in the form of an emulsion or a liposomal preparation. The compositions are preferably sterile, non-pyrogenic and isotonic and contain the pharmaceutically conventional and acceptable additives known per se. Additionally, reference is made to the regulations of the U.S. Pharmacopoeia or Remington's Pharmaceutical Sciences, Mac Publishing Company (1990).

In the field of human and veterinary medical therapy and prophylaxis pharmaceutically effective medicaments containing at least one EGFR binding ubiquitin mutein in accordance with the invention can be prepared by methods known per se. Depending on the galenic preparation these compositions can be administered parentally by injection or infusion, systemically, rectally, intraperitoneally, intramuscularly, subcutaneously, transdermally or by other conventionally employed methods of application. The type of pharmaceutical preparation depends on the type of disease to be treated, the route of administration, the severity of the disease, the patient to be treated and other factors known to those skilled in the art of medicine.

A pharmaceutical composition according to the invention may be present in the form of a composition, wherein the different active ingredients and diluents and/or carriers are admixed with each other, or may take the form of a combined preparation, where the active ingredients are present in partially or totally distinct form. A suitable carrier or excipient may be a liquid material which can serve as a vehicle or medium for the active ingredient. An example for such a combination or combined preparation is a kit-of-parts.

In a still further aspect the invention discloses diagnostic compositions comprising EGFR binding ubiquitin mutein according to the invention specifically binding specific targets/antigens or its isoforms together with diagnostically acceptable carriers.

Since enhanced EGFR expression is correlated with tumor malignancy, it is desirable to develop diagnostics for non-invasive imaging in order to gain information about EGFR expression status in patients. Furthermore, EGFR imaging could be useful for the assessment of the response of a patient to a therapeutic treatment. For example, using a protein of the invention labelled with a suitable radioisotope or fluorophore can be used for non-invasive imaging to determine the location of tumors and metastasis. (for review see for example Milenic et al. 2008 Cancer Biotherapy & Radiopharmaceuticals 23: 619-631; Hoeben et al. 2011, Int. Journal Cancer 129: 870-878). Due to their pharmacokinetic characteristics, intact antibodies are not suitable for routine imaging. Due to their small size and high affinity, radiolabelled or fluorescently labelled fusion proteins of the invention are expected to be much better suited for use as diagnostics for imaging.

It is expected that a protein of the invention can be advantageously applied in therapy. In particular, the molecules are expected to show superior tumor targeting effect and desired biodistribution and thus, reduced side effects. Pharmaceutical compositions of the invention may be manufactured in any conventional manner.

EXAMPLES

The following Examples are provided for further illustration of the invention. The invention is particularly exemplified by particular modifications of ubiquitin resulting in binding to EGFR. The invention, however, is not limited thereto, and the following Examples merely show the practicability of the invention on the basis of the above descrip-

Example 1

Expression and Purification of EGFR-binding Ubiquitin Muteins (Affilin)

Target: Recombinant human EGFR-Fc Chimera was purchased from R&D Systems (catalog no. 344-ER-050). A DNA sequence encoding the extracellular domain (Met 1-Ser 645) of human EGFR (NP_005219) was fused with the Fc region of human IgG1 at the C-terminus.

Expression/Purification: Affilin molecules were subcloned to an expression vector using standard methods known to a skilled person, purified and analyzed as described below.

Analysis Expression/Purification: Further analysis included SDS-PAGE, SE-HPLC and RP-HPLC. Protein concentrations were determined by absorbance measurement at 280 nm. After purification size exclusion chromatography (SE HPLC or SEC) has been performed using a Dionex HPLC system and a Superdex™ 200 HiLoad 16/600 column (GE Healthcare). The column has a volume of 120 ml and was equilibrated with 2 CV. The samples were applied with a flow rate of 1 ml/min purification buffer B. Fraction collection starts as the signal intensity reaches 10 mAU. Following SDS-PAGE analysis positive fractions were pooled and their protein concentrations were measured. RP chromatography (RP HPLC) has been performed using a Dionex HPLC system and a Vydac 214MS54 C4 (4.6×250 mm, 5 µm, 300 Å) column (GE Healthcare). All Affilin proteins were expressed and highly purified by affinity chromatography and gel filtration.

Example 2

Solubility Analysis of EGFR-binding Affilin Proteins

Proteins were recovered from the pellets by addition of 8 M urea. Supernatants and resuspended pellets were analyzed by NuPage Novex 4-12% Bis-Tris SDS gels and stained with Coomassie. All Affilin proteins were soluble. For example, Affilin 139819 displayed a high solubility (100% soluble expression).

Example 3

Anti-EGFR Affilin Proteins are Stable at High Temperatures (Analysis by Differential Scanning Fluorimetry, DSF)

Thermal stability of the binding proteins of the invention was determined by Differential Scanning Fluorimetry. Each probe was transferred at concentrations of 0.1 µg/µL to a MicroAmp® Optical 384-well plate well plate, and SYPRO Orange dye was added at suitable dilution. A temperature ramp from 25 to 95° C. was programmed with a heating rate of 1° C. per minute (ViiA-7 Applied Biosystems). Fluorescence was constantly measured at an excitation wavelength of 520 nm and the emission wavelength at 623 nm (ViiA-7, Applied Biosystems). The midpoints of transition for the thermal unfolding (Tm, melting points) are shown for selected variants in FIG. 1. Anti-EGFR Affilin proteins of the invention have calculated thermal transition points for the unfolding of the proteins (thermal stabilities) in the temperature range of about 60° C. and 80° C. Fusion proteins comprising anti-EGFR Affilin and monoclonal antibodies show similar melting points (between 65-69° C.). Similar melting points correlate to related protein structures. All anti-EGFR Affilin proteins have similar melting temperatures. The stability of all binding proteins is comparable to the stability of the control proteins.

Example 4

Analysis of EGFR Binding of Affilin Proteins (Surface Plasmon Resonance, SPR)

A CM5 sensor chip (GE Healthcare) was equilibrated with SPR running buffer. Surface-exposed carboxylic groups were activated by passing a mixture of EDC and NHS to yield reactive ester groups. 700-1500 RU EGFR-Fc (on-ligand) were immobilized on a flow cell, IgG-Fc (off-ligand) was immobilized on another flow cell at a ratio of 1:3 (hIgG-Fc:Target) to the target. Injection of ethanolamine after ligand immobilization removes non-covalently bound ligand. Upon ligand binding, protein analyte was accumulated on the surface increasing the refractive index. This change in the refractive index was measured in real time and plotted as response or resonance units (RU) versus time. The analytes were applied to the chip in serial dilutions with a flow rate of 30 µl/min. The association was performed for 30 seconds and the dissociation for 60 seconds. After each run, the chip surface was regenerated with 30 µl regeneration buffer and equilibrated with running buffer. A dilution series of Cetuximab served as positive control, whereas a dilution series of unmodified ubiquitin represents the negative control. The control samples were applied to the matrix with a flow rate of 30 µl/min, while they associate for 60 seconds and dissociate for 120 seconds. Regeneration and re-equilibration were performed as previously mentioned. Binding studies were carried out by the use of the Biacore® 3000 (GE Healthcare); data evaluation was operated via the BIAevaluation 3.0 software, provided by the manufacturer, by the use of the Langmuir 1:1 model (RI=0). Results of binding to EGFR are shown in FIG. 1. Evaluated dissociation constants ($K_D$) were standardized against off-target and indicated. All anti-EGFR Affilin proteins tested bind with high affinity to EGFR. Clone 138840 without PDI motif (SEQ ID NO: 77) does not show any binding affinity to EGFR.

Example 5

Binding to Cell Surface Expressed EGFR (FACS Analysis)

Flow cytometry was used to analyze the interaction of anti-EGFR Affilin proteins with surface-exposed EGFR. EGFR overexpressing CHO-K1 cells and empty vector control CHO-K1 cells were used. The anti-EGFR monoclonal antibody Cetuximab was used as positive control. Results are summarized in FIG. 2.

Cells were detached from the culture flask bottom and diluted in pre-cooled FACS blocking buffer and a cell suspension dilution was prepared for cell staining. As the cell number was determined, the cells were adjusted to $1 \times 10^6$ cells/ml. Then, the diluted cell suspension was transferred into a 96 well plate (Greiner) in triplicate for each cell line.

Different concentrations of Affilin proteins (e.g. 500, 50, 5, or 0.5 nM) or control (SEQ ID NO: 2 or 4) were added to the cells and incubated. The supernatants were removed and 100 μl/well rabbit anti-Strep antibody 1:300 diluted in FACS blocking buffer was added. After removal of the primary antibody goat anti-human IgG Alexa Fluor 488 antibody 1:1000 diluted was applied. Flow cytometry measurement was conducted on the Guava easy-Cyte HT device from Merck-Millipore at excitation wavelength 499 nm and emission wavelength 520 nm. Results are shown in FIG. 3.

In the demonstrated FACS analysis, binding of proteins on cells exogenously expressing human EGFR was confirmed. No non-specific binding was observed on cell lines that do not express EGFR. Further EGFR binding proteins of the invention showed binding to cells exogenously expressing human EGFR, for example, Affilin 139754, Affilin 139791, and Affilin 139780.

Example 6

Competition Analysis that EGFR Binding Affilin Proteins Bind to Other Epitope than Anti-EGFR Antibody Cetuximab Epitopes to which anti-EGFR antibodies bind have been described, see for example Freeman et al. 2008, Journal of Clinical Oncol., 26:14536. The conformational epitope recognized by Cetuximab covers a large surface on domain III of the EGFR (see for example Li et al, 2005, Cancer Cell. 7:301-311 and Chao et al., 2004, J Mol Biol. 342:539-550). Affilin molecules that bind to different EGFR epitopes than Cetuximab can be useful in certain medical embodiments. To investigate whether the isolated anti-EGFR Affilin variants can compete with the approved anti-EGFR antibody Cetuximab, the following assay was performed: EGFR (i.e., the extracellular domain of EGFR with His-tag; Acrobiosystems) was immobilized on a CM5 Biacore chip using NHS/EDC chemistry resulting in 1000 response units (RU). In a first experiment, all Affilin molecules (139819 and 142205) were injected at one defined concentration (2.5 μM) at a flow rate of 30 μl/min PBST 0.005% Tween 20 (FIG. 5, solid line). In the second experiment, the same flow channel was first pre-loaded with Cetuximab (200 nM) until the chip surface was saturated. After loading Cetuximab, the variants were identically applied as in experiment 1 (2.5 μM, FIG. 5, dashed line). For better clarification both sensorgram traces were aligned at the last injected Affilin.

It was demonstrated that the EGFR binding of Affilin 139819 was not influenced by the presence of Cetuximab. Thus, no competition was observed, meaning that Cetuximab and anti-EGFR Affilin proteins of the invention bind to different epitopes of EGFR. It is concluded that Affilin proteins with PDI motif bind to different surface exposed amino acids of EGFR than Cetuximab. EGFR-specific Affilin proteins with PDI motif bind to an epitope not partially or completely overlapping with the Cetuximab epitope.

Anti-EGFR Affilin proteins without PDI motif bind to an epitope in close proximity to the Cetuximab epitope or even partially or completely overlap with the Cetuximab epitope.

Example 7

EGFR Binding Affilin Proteins Bind to Xenograft Tumor Tissue

Different concentrations of binding proteins of the invention were compared with respect to EGFR-binding on MDA-MB231 tumor tissue slices. Slices of a thickness of 6 μm were fixed with ice cold absolute Acetone. After blocking with 5% horse serum, slices were incubated with 500 nM or 100 nM of Affilin 138819 (SEQ ID NO: 71), Affilin 138838 (SEQ ID NO: 69), Affilin 138840 (SEQ ID NO: 77, no PDI motif), and Affilin 138845 (SEQ ID NO: 73), and as control unmodified ubiquitin (SEQ ID NO: 7) respectively. Binding proteins were detected with a rabbit anti-StrepTag-antibody and an anti-rabbit-IgG-Alexa488. All Affilin proteins bind to EGFR expressed on human tumor tissue, as shown in FIG. 6, in particular Affilin proteins with PDI motif show strong binding to EGFR.

Example 8

EGFR Binding Affilin Proteins Bind to Extracellular EGFR Expressed on Tumor Cells (Immunocytochemistry)

A431 cells are derived from epidermoid carcinoma and are known for the high expression levels of EGFR. A431 cells were seeded in Lab-Tek® Chamber Slides (Sigma-Aldrich) and incubated for 2 days at 37° C., 5% CO$_2$. Cells were fixed with 3% paraformaldehyde for 10 minutes at RT, washed with PBS and subsequently blocked with blocking solution (BS, 3% BSA+0.1% Triton-X100) for 30 min at 4° C. Cells were then incubated with 500 nM binding protein (Affilin proteins 139791, 139819, 139989, 142232, 142265) or 10 nM Cetuximab as control for 1h at 4° C. Unmodified ubiquitin (referred to as 139090 in FIG. 7, SEQ ID NO: 4) served as negative control. After washing with PBS cells were incubated with rabbit anti-Strep-antibody (1:500) for 1 h at 4° C. Cells were then incubated with donkey anti-Rabbit Alexa488 (1:1000) or goat anti-Human Alexa 594 (1:1000) secondary antibodies followed by visualization of cell nuclei with DAPI. Chamber slides were dissembled and the glass slide was covered with Mowiol and a cover glass. Cells were imaged at a Zeiss Axio Scope.A1 microscope and images were processed using standard software packages.

The staining of A431 tumor cells expressing EGFR confirms binding of Affilin 139791 (SEQ ID NO: 49), Affilin 139819 (SEQ ID NO: 39), Affilin 142232 (SEQ ID NO: 29) and Affilin 142265 (SEQ ID NO: 75, no PDI motif) to extracellular EGFR. Of all Affilin molecules tested, Affilin 142232 showed the strongest staining on A431 tumor cells. Affilin 142265 shows a significant weaker signal in comparison to Affilin 142232, Affilin 139791, and Affilin 139819 (see FIG. 7). For Affilin 139989, no binding to extracellular EGFR on A431 tumor cells was detectable, confirming the results obtained by FACS analysis (see FIG. 2). Further Affilin proteins were tested for positive staining of A431 tumor cells (for example, Affilin 139820).

Example 9

Binding Analysis of Fusion Proteins of Affilin and Cetuximab

EGFR-Affilin 139819 (SEQ ID NO: 39) (or unmodified di-ubiquitin, SEQ ID NO: 4) was linked to the C- or N-terminus of the light chain or heavy chain of the anti EGFR antibody Cetuximab. The first up to 20 amino acids of SEQ ID NO: 86-89 and 107-110 refer to a signal sequence. The cDNA encoding Cetuximab or the fusion proteins were transiently transfected into FreeStyle™ 293-F cells and expressed in serum-free/animal component-free media. Expression was confirmed by Western Blot analysis.

Fusion proteins were purified from the supernatants by Protein A affinity chromatography (GE-Healthcare cat no 17-0402-01) with an AKTAxpress® (GE Healthcare). Further purification of the fusion proteins was achieved by gel filtration. Further analysis included SDS-PAGE, SE-HPLC and RP-HPLC. Binding studies were carried out by the use of the Biacore® 3000 (GE Healthcare) as described above and as shown in FIG. 8. Further, FACS analysis of binding of the fusion proteins to human EGFR expressed in CHO-K1 cells is shown in Table 1.

TABLE 1

Affinity data for EGFR-ubiquitin-mutein-cetuximab fusion proteins of the invention for EGFR (FACS)

| Fusion protein or Cetuximab | $K_D$ [nM] |
|---|---|
| Cetuximab (control) | 1.2 |
| CH-Ubiquitin (SEQ ID NO: 107) | 0.7 |
| CH-139819 (SEQ ID NO: 108) | 0.6 |
| CL-Ubiquitin (SEQ ID NO: 88) | 0.6 |
| CL-139819 (SEQ ID NO: 87) | 0.9 |
| NH-Ubiquitin (SEQ ID NO: 109) | 0.6 |
| NH-139819 (SEQ ID NO: 110) | 0.8 |
| NL-Ubiquitin (SEQ ID NO: 89) | 0.8 |
| NL-139819 (SEQ ID NO: 86) | 0.5 |

Example 10

Binding Analysis of Homo-Dimeric Affilin Proteins

A homo-dimer of EGFR-Affilin 139819 (SEQ ID NO: 39) was expressed as described in Example 1; expression was confirmed by Western Blot analysis. The homo-dimer was purified by Protein A affinity chromatography (GE-Healthcare cat no 17-0402-01) with an AKTAxpress (GE Healthcare). Further purification of the fusion proteins was achieved by gel filtration (Superdex 75 16/600). Further analysis included SDS-PAGE, SE-HPLC and RP-HPLC, as described above. Binding studies were carried out by the use of the Biacore3000 (GE Healthcare) as described above and as shown in FIG. 11. Further, FACS analysis of binding of homo-dimers to human extracellular EGFR expressed in CHO-K1 cells or in A549 cells is described above and shown in FIG. 12A-D. The affinity of the homo-dimer is about 10 fold better than the Affilin 139819.

Similar results were obtained upon homo-dimerization of Affilin 142265. The affinity to EGFR is 445 nM for Affilin 142265, as measured by Biacore. However, upon homo-dimerization (Affilin 142265×Affilin 142265), the affinity is improved about 10 fold (48 nM). Thermal stability was not influenced by the homo-dimerization of Affilin 142265.

Example 11

Binding Analysis of Hetero-Dimeric Affilin Fusion Proteins

A hetero-dimeric fusion proteins of EGFR-Affilin 139791 (SEQ ID NO: 49) and EGFR-Affilin 139819 (SEQ ID NO: 39) was expressed as described in Example 1; expression was confirmed by Western Blot analysis. The homo-dimer was purified by Protein A affinity chromatography and by gel filtration as described above. Further analysis included SDS-PAGE, SE-HPLC and RP-HPLC, as described above. Binding studies were carried out by the use of the Biacore® 3000 (GE Healthcare) as described above and as shown in Table 2.

TABLE 2

Biochemical characterization for hetero-dimeric EGFR-binding Affilin constructs.

| Affilin | Purity SDS (%) | SE-HPLC (%) | RP-HPLC (%) | $K_D$ (nM) | $k_{on}$ (1/Ms) | $k_{off}$ (1/s) |
|---|---|---|---|---|---|---|
| 139819 | >99 | >99 | 97 | 16.9 | $6.5 \times 10^4$ | $1.1 \times 10^{-3}$ |
| 139791 |  | >99 | >99 | 256 | $3.98 \times 10^3$ | $1.02 \times 10^{-3}$ |
| 139791 fused to 139819 | >99 | >99 | >99 | 16.3 | $5.61 \times 10^4$ | $9.12 \times 10^{-4}$ |

The invention claimed is:

1. An epidermal group factor receptor (EGFR) binding protein comprising at least one ubiquitin mutein, wherein the ubiquitin mutein:
   (i) has a proline (P), a valine (V), or an alanine (A) at an amino acid position that corresponds to amino acid number 64 of SEQ ID NO: 1 or SEQ ID NO: 4;
   (ii) has an aspartic acid (D) or a glutamic acid (E) at a position that corresponds to amino acid number 65 of SEQ ID NO: 1 or SEQ ID NO: 4;
   (iii) has an isoleucine (I), valine (V), alanine (A), methionine (M), phenylalanine (F), tyrosine (Y), tryptophan (W), or leucine (L) at a position that corresponds to amino acid number 66 of SEQ ID NO: 1 or SEQ ID NO: 4;
   (iv) has an arginine (R), glutamine (Q), histidine (H), lysine (K), glycine (G), serine (S), threonine (T), asparagine (N), valine (V), isoleucine (I), or tryptophan (W) at a position that corresponds to amino acid 62 of SEQ ID NO: 1 or SEQ ID NO: 4;
   (v) has an asparagine (N), histidine (H), alanine (A), serine (S), arginine (R), glutamic acid (E), threonine (T), glutamine (Q), or lysine (K) at a position that corresponds to amino acid 63 of SEQ ID NO: 1 or SEQ ID NO: 4;
   (vi) has at least 86% amino acid sequence identity to the ubiquitin of SEQ ID NO: 1 or the di-ubiquitin of SEQ ID NO: 4; and
   (vii) has a binding affinity ($K_D$) of less than 700 nM for the extracellular domain of human EGFR.

2. The EGFR binding protein of claim 1 wherein the EGFR binding protein comprises an amino acid sequence that comprises a tripeptide sequence at positions that correspond to amino acid numbers 64-66 of SEQ ID NO: 1 or SEQ ID NO: 4 that is selected from the group consisting of ADI, PDI, VDI, PDV, and VDV.

3. The EGFR binding protein of claim 1, wherein the EGFR binding protein binds to a different EGFR epitope than does the anti-EGFR monoclonal antibody Cetuximab.

4. The EGFR binding protein of claim 1, wherein the EGFR binding protein comprises a fusion protein of two identical or two different ubiquitin muteins connected via a peptide linker.

5. The EGFR binding protein of claim 1, wherein the ubiquitin mutein comprises an amino acid sequence selected from the group consisting of SEQ ID NOs: 8-73, 113, and 114.

6. The EGFR binding protein of claim 1, further comprising at least one additional molecule wherein the at least one additional molecule is selected from the group consisting of:
   (i) a pharmacokinetic moiety that modulates the serum half-life of the EGFR binding protein, optionally selected from the group consisting of a polyethylene glycol, a human serum albumin, an anti-human serum albumin, an albumin-binding peptide, a polymer sequence that forms a random coil, an immunoglobulin or a fragment thereof, and a polysaccharide;
   (ii) a therapeutically active component, optionally selected from the group consisting of a monoclonal antibody or a fragment thereof with the binding specificity of said monoclonal antibody, a cytokine, a chemokine, a cytotoxic compound, an enzyme or a derivative thereof, and a radionuclide; and
   (iii) a diagnostic component, optionally selected from the group consisting of a fluorescent compound, a photosensitizer, and a radionuclide.

7. A composition comprising the EGFR binding protein of claim 1.

8. The EGFR binding protein of claim 1, wherein the ubiquitin mutein has an amino acid sequence motif at positions corresponding to positions 62-66 of SEQ ID NO: 1 or SEQ ID NO: 4 that is selected from the group consisting of RNPDI, QNPDI, RHPDI, QHPDI, QAPDI, QQPDI, GEPDI, GHPDI, IHADI, HHPDI, RRVDV, SAPDI, SHPDI, THPDI, TSPDI, VNPDI, and QSPDI.

9. The EGFR binding protein of claim 1, wherein the ubiquitin mutein further comprises an insertion of 2-10 amino acids after the position corresponding to amino acid 9 of SEQ ID NO: 1 or SEQ ID NO: 4, or a substitution of the amino acids at the positions corresponding to positions 6 and 8 of SEQ ID NO: 1 or SEQ ID NO: 4.

10. The EGFR binding protein of claim 1, wherein the ubiquitin mutein comprises an amino acid sequence that is at least 90% identical to one of SEQ ID NOs: 8-73, 113, and 114.

* * * * *